US012433535B2

(12) United States Patent
Wood et al.

(10) Patent No.: US 12,433,535 B2
(45) **Date of Patent: *Oct. 7, 2025**

(54) METHOD AND SYSTEM FOR OPTIMIZING A PROJECTED VEIN IMAGE AND IDENTIFYING VEIN LOCATIONS USING VEIN SCANNER

(71) Applicant: AccuVein Inc., Medford, NY (US)

(72) Inventors: Fred Wood, Medford, NY (US); Vincent Luciano, Shoreham, NY (US); Ron Goldman, Cold Springs Harbor, NY (US)

(73) Assignee: AccuVein, Inc., Medford, NY (US)

( * ) Notice: Subject to any disclaimer, the term of this patent is extended or adjusted under 35 U.S.C. 154(b) by 28 days.

This patent is subject to a terminal disclaimer.

(21) Appl. No.: 18/480,563

(22) Filed: Oct. 4, 2023

(65) Prior Publication Data

US 2024/0090832 A1 Mar. 21, 2024

Related U.S. Application Data

(63) Continuation of application No. 16/595,750, filed on Oct. 8, 2019, now Pat. No. 11,826,166, which is a (Continued)

(51) Int. Cl.

*A61B 5/00* (2006.01)
*A61M 5/42* (2006.01)

(Continued)

(52) U.S. Cl.

CPC ............ *A61B 5/489* (2013.01); *A61B 5/0062* (2013.01); *A61B 5/7225* (2013.01); *A61M 5/427* (2013.01);

(Continued)

(58) Field of Classification Search

CPC ..... A61B 5/489; A61B 5/0062; A61B 5/7225; A61B 2090/366; A61B 2560/0204;

(Continued)

(56) References Cited

U.S. PATENT DOCUMENTS

| | | |
|---|---|---|
| 3,136,310 A | 6/1964 | Meltzer |
| 3,349,762 A | 10/1967 | Kapany |

(Continued)

FOREIGN PATENT DOCUMENTS

| | | |
|---|---|---|
| FR | 2289149 | 5/1976 |
| GB | 1298707 | 12/1972 |

(Continued)

OTHER PUBLICATIONS

Wiklof, Chris, "Display Technology Spawns Laser Camera," LaserFocusWorld, Dec. 1, 2004, vol. 40, Issue 12, PennWell Corp., USA.

(Continued)

*Primary Examiner* — Christopher Koharski
*Assistant Examiner* — James F McDonald, III
(74) *Attorney, Agent, or Firm* — Thomas A. O'Rourke; James Bongiorno; O'Rourke IP Law, PLLC

(57) ABSTRACT

A portable vein viewer apparatus may be battery powered and hand-held to reveal patient vasculature information to aid in venipuncture processes. The apparatus comprises a first laser diode emitting infrared light, and a second laser diode emitting only visible wavelengths, wherein vasculature absorbs a portion of the infrared light causing reflection of a contrasted infrared image. A pair of silicon PIN photodiodes, responsive to the contrasted infrared image, causes transmission of a corresponding signal. The signal is processed through circuitry to amplify, sum, and filter the outputted signals, and with the use of an image processing algorithm, the contrasted image is projected onto the (Continued)

(Centering of Display Light Above Vein Centerline for Display Accuracy)

patient's skin surface using the second laser diode. Revealed information may comprise vein location, depth, diameter, and degree of certainty of vein locations. Projection of vein images may be a positive or a negative image. Venipuncture needles may be coated to provide visibility in projected images.

19 Claims, 107 Drawing Sheets

Related U.S. Application Data continuation of application No. 15/678,355, filed on Aug. 16, 2017, now Pat. No. 10,518,046, which is a continuation of application No. 14/718,422, filed on May 21, 2015, now Pat. No. 9,789,267, which is a continuation of application No. 13/778,426, filed on Feb. 27, 2013, now Pat. No. 9,061,109, which is a continuation of application No. 12/804,506, filed on Jul. 22, 2010, now Pat. No. 8,463,364.

(60) Provisional application No. 61/271,587, filed on Jul. 22, 2009.

(51) Int. Cl.
*H02J 7/00* (2006.01)
*A61B 90/00* (2016.01)

(52) U.S. Cl.
CPC ....... *H02J 7/0044* (2013.01); *A61B 2090/366* (2016.02); *A61B 2560/0204* (2013.01); *A61B 2560/0431* (2013.01); *A61B 2560/0456* (2013.01); *A61M 2205/18* (2013.01); *A61M 2205/3306* (2013.01); *A61M 2205/3606* (2013.01); *A61M 2205/502* (2013.01); *A61M 2210/12* (2013.01)

(58) Field of Classification Search
CPC ... A61B 2560/0431; A61B 2560/0456; A61M 5/427; A61M 2205/18; A61M 2205/3306; A61M 2205/3606; A61M 2205/502; A61M 2210/12; H02J 7/0044; H02J 2310/23
See application file for complete search history.

(56) References Cited

U.S. PATENT DOCUMENTS 3,511,227 A 5/1970 Johnson
3,527,932 A 9/1970 Thomas
3,818,129 A 6/1974 Yamamoto
3,984,629 A 10/1976 Gorog
4,030,209 A 6/1977 Dreiding
4,057,784 A 11/1977 Tafoya
4,109,647 A 8/1978 Stern et al.
4,162,405 A 7/1979 Chance et al.
4,182,322 A 1/1980 Miller
4,185,808 A 1/1980 Donohoe et al.
4,213,678 A 7/1980 Pomerantzeff et al.
4,265,227 A 5/1981 Ruge
4,312,357 A 1/1982 Andersson et al.
4,315,318 A 2/1982 Kato et al.
4,321,930 A 3/1982 Jobsis et al.
4,393,366 A 7/1983 Hill
4,495,949 A 1/1985 Stoller
4,502,075 A 2/1985 DeForest et al.
4,510,938 A 4/1985 Jobsis et al.
4,536,790 A 8/1985 Kruger et al.
4,565,968 A 1/1986 Macovski
4,567,896 A 2/1986 Barnea et al.
4,576,175 A 3/1986 Epstein
4,586,190 A 4/1986 Tsuj
4,590,948 A 5/1986 Nilsson
4,596,254 A 6/1986 Adrian et al.
4,619,249 A 10/1986 Landry
4,669,467 A 6/1987 Willett et al.
4,697,147 A 9/1987 Moran et al.
4,699,149 A 10/1987 Rice
4,703,758 A 11/1987 Omura
4,766,299 A 8/1988 Tierney et al.
4,771,308 A 9/1988 Tejima et al.
4,780,919 A 11/1988 Harrison
4,799,103 A 1/1989 Muckerheide
4,817,622 A 4/1989 Pennypacker et al.
4,846,183 A 7/1989 Martin
4,861,973 A 8/1989 Hellekson et al.
4,862,894 A 9/1989 Fujii
4,899,756 A 2/1990 Sonek
4,901,019 A 2/1990 Wedeen
4,926,867 A 5/1990 Kanda et al.
RE33,234 E 6/1990 Landry
4,938,205 A 7/1990 Nudelman
5,074,642 A 12/1991 Hicks
5,088,493 A 2/1992 Giannini et al.
5,103,497 A 4/1992 Hicks
5,146,923 A 9/1992 Dhawan
5,174,298 A 12/1992 Dolfi et al.
5,184,188 A 2/1993 Bull et al.
5,214,458 A 5/1993 Kanai
5,222,495 A 6/1993 Clarke et al.
5,261,581 A 11/1993 Harden, Sr.
5,293,873 A 3/1994 Fang
5,339,817 A 8/1994 Nilsson
5,371,347 A 12/1994 Plesko
5,406,070 A 4/1995 Edgar et al.
5,418,546 A 5/1995 Nakagakiuchi et al.
5,423,091 A 6/1995 Lange
5,436,655 A 7/1995 Hiyama et al.
5,445,157 A 8/1995 Adachi et al.
D362,910 S 10/1995 Creaghan
5,487,740 A 1/1996 Sulek et al.
5,494,032 A 2/1996 Robinson et al.
5,497,769 A 3/1996 Gratton et al.
5,504,316 A 4/1996 Bridgelall et al.
5,519,208 A 5/1996 Esparza et al.
5,541,820 A 7/1996 McLaughlin
5,542,421 A 8/1996 Erdman
5,598,842 A 2/1997 Ishihara et al.
5,603,328 A 2/1997 Zucker et al.
5,608,210 A 3/1997 Esparza et al.
5,610,387 A 3/1997 Bard et al.
5,625,458 A 4/1997 Alfano et al.
5,631,976 A 5/1997 Bolle et al.
5,655,530 A 8/1997 Messerschmidt
5,678,555 A 10/1997 O'Connell
5,716,796 A 2/1998 Bull et al.
5,719,399 A 2/1998 Alfano et al.
5,740,801 A 4/1998 Branson
5,747,789 A 5/1998 Godik
5,756,981 A 5/1998 Roustaei et al.
5,758,650 A 6/1998 Miller et al.
5,772,593 A 6/1998 Hakamata
5,787,185 A 7/1998 Clayden
5,814,040 A 9/1998 Nelson et al.
5,836,877 A 11/1998 Zavislan
5,847,394 A 12/1998 Alfano et al.
5,860,967 A 1/1999 Zavislan et al.
5,929,443 A 7/1999 Alfano et al.
5,946,220 A 8/1999 Lemelson
5,947,906 A 9/1999 Dawson, Jr. et al.
5,966,204 A 10/1999 Abe
5,966,230 A 10/1999 Swartz et al.
5,969,754 A 10/1999 Zeman
5,982,553 A 11/1999 Bloom et al.
5,988,817 A 11/1999 Mizushima et al.
5,995,856 A 11/1999 Mannheimer et al.
5,995,866 A 11/1999 Lemelson
6,006,126 A 12/1999 Cosman
6,032,070 A 2/2000 Flock et al.
6,056,692 A 5/2000 Schwartz

(56) References Cited

U.S. PATENT DOCUMENTS

| | | | |
|---|---|---|---|
| 6,061,583 | A | 5/2000 | Ishihara et al. |
| 6,083,486 | A | 7/2000 | Weissleder et al. |
| 6,101,036 | A | 8/2000 | Bloom |
| 6,113,536 | A | 9/2000 | Aboul-Hosn et al. |
| 6,122,042 | A | 9/2000 | Wunderman et al. |
| 6,132,379 | A | 10/2000 | Patacsil et al. |
| 6,135,599 | A | 10/2000 | Fang |
| 6,141,985 | A | 11/2000 | Cluzeau et al. |
| 6,142,650 | A | 11/2000 | Brown et al. |
| 6,149,061 | A | 11/2000 | Massieu et al. |
| 6,149,644 | A | 11/2000 | Xie |
| 6,171,301 | B1 | 1/2001 | Nelson et al. |
| 6,178,340 | B1 | 1/2001 | Svetliza |
| 6,230,046 | B1 | 5/2001 | Crane et al. |
| 6,240,309 | B1 | 5/2001 | Yamashita et al. |
| 6,251,073 | B1 | 6/2001 | Imran et al. |
| 6,263,227 | B1 | 7/2001 | Boggett et al. |
| 6,272,376 | B1 | 8/2001 | Marcu et al. |
| 6,301,375 | B1 | 10/2001 | Choi |
| 6,305,804 | B1 | 10/2001 | Rice et al. |
| 6,314,311 | B1 | 11/2001 | Williams et al. |
| 6,334,850 | B1 | 1/2002 | Amano et al. |
| 6,353,753 | B1 | 3/2002 | Flock et al. |
| 6,424,858 | B1 | 7/2002 | Williams |
| 6,436,655 | B1 | 8/2002 | Bull et al. |
| 6,438,396 | B1 | 8/2002 | Cook et al. |
| 6,463,309 | B1 | 10/2002 | Ilia |
| 6,464,646 | B1 | 10/2002 | Shalom et al. |
| 6,523,955 | B1 | 2/2003 | Eberl et al. |
| 6,542,246 | B1 | 4/2003 | Toida |
| 6,556,854 | B1 | 4/2003 | Sato et al. |
| 6,556,858 | B1 | 4/2003 | Zeman |
| 6,599,247 | B1 | 7/2003 | Stetten |
| 6,631,286 | B2 | 10/2003 | Pfeiffer et al. |
| 6,648,227 | B2 | 11/2003 | Swartz et al. |
| 6,650,916 | B2 | 11/2003 | Cook et al. |
| 6,689,075 | B2 | 2/2004 | West |
| 6,690,964 | B2 | 2/2004 | Bieger et al. |
| 6,702,749 | B2 | 3/2004 | Paladini et al. |
| 6,719,257 | B1 | 4/2004 | Greene et al. |
| 6,755,789 | B2 | 6/2004 | Stringer et al. |
| 6,777,199 | B2 | 8/2004 | Bull et al. |
| 6,782,161 | B2 | 8/2004 | Barolet et al. |
| 6,845,190 | B1 | 1/2005 | Smithwick et al. |
| 6,882,875 | B1 | 4/2005 | Crowley |
| 6,889,075 | B2 | 5/2005 | Marchitto et al. |
| 6,913,202 | B2 | 7/2005 | Tsikos et al. |
| 6,923,762 | B1 | 8/2005 | Creaghan, Jr. |
| 6,980,852 | B2 | 12/2005 | Jersey-Willuhn et al. |
| 7,092,087 | B2 | 8/2006 | Kumar et al. |
| 7,113,817 | B1 | 9/2006 | Winchester, Jr. et al. |
| 7,158,660 | B2 | 1/2007 | Gee, Jr. et al. |
| 7,158,859 | B2 | 1/2007 | Wang et al. |
| 7,204,424 | B2 | 4/2007 | Yavid et al. |
| 7,225,005 | B2 | 5/2007 | Kaufman et al. |
| 7,227,611 | B2 | 6/2007 | Hull et al. |
| 7,239,909 | B2 | 7/2007 | Zeman |
| 7,247,832 | B2 | 7/2007 | Webb |
| 7,280,860 | B2 | 10/2007 | Ikeda et al. |
| 7,283,181 | B2 | 10/2007 | Allen et al. |
| 7,302,174 | B2 | 11/2007 | Tan et al. |
| 7,333,213 | B2 | 2/2008 | Kempe |
| D566,283 | S | 4/2008 | Brafford et al. |
| 7,359,531 | B2 | 4/2008 | Endoh et al. |
| 7,376,456 | B2 | 5/2008 | Marshik-Geurts et al. |
| 7,428,997 | B2 | 9/2008 | Wiklof et al. |
| 7,431,695 | B1 | 10/2008 | Creaghan |
| 7,448,995 | B2 | 11/2008 | Wiklof et al. |
| 7,532,746 | B2 | 5/2009 | Marcotte et al. |
| 7,545,837 | B2 | 6/2009 | Oka |
| 7,559,895 | B2 | 7/2009 | Stetten et al. |
| 7,579,592 | B2 | 8/2009 | Kaushal |
| 7,608,057 | B2 | 10/2009 | Woehr et al. |
| 7,699,776 | B2 | 4/2010 | Walker et al. |
| 7,708,695 | B2 | 5/2010 | Akkermans et al. |
| 7,792,334 | B2 | 9/2010 | Cohen et al. |
| 7,846,103 | B2 | 12/2010 | Cannon, Jr. et al. |
| 7,848,103 | B2 | 12/2010 | Zhan |
| 7,904,138 | B2 | 3/2011 | Goldman et al. |
| 7,904,139 | B2 | 3/2011 | Chance |
| 7,925,332 | B2 | 4/2011 | Crane et al. |
| 7,966,051 | B2 | 6/2011 | Xie et al. |
| 8,032,205 | B2 | 10/2011 | Mullani |
| 8,078,263 | B2 | 12/2011 | Zeman et al. |
| 8,187,189 | B2 | 5/2012 | Jung et al. |
| 8,199,189 | B2 | 6/2012 | Kagenow et al. |
| 8,320,998 | B2 | 11/2012 | Sato |
| 8,336,839 | B2 | 12/2012 | Boccoleri et al. |
| 8,364,246 | B2 | 1/2013 | Thierman |
| 8,467,855 | B2 | 6/2013 | Yasui |
| 8,480,662 | B2 | 7/2013 | Stolen et al. |
| 8,494,616 | B2 | 7/2013 | Zeman |
| 8,498,694 | B2 | 7/2013 | McGuire, Jr. et al. |
| 8,509,495 | B2 | 8/2013 | Xu et al. |
| 8,537,203 | B2 | 9/2013 | Seibel et al. |
| 8,548,572 | B2 | 10/2013 | Crane |
| 8,630,465 | B2 | 1/2014 | Wieringa et al. |
| 8,649,848 | B2 | 2/2014 | Crane et al. |
| 2001/0006426 | A1 | 7/2001 | Son et al. |
| 2001/0056237 | A1 | 12/2001 | Cane et al. |
| 2002/0016533 | A1 | 2/2002 | Marchitto et al. |
| 2002/0118338 | A1 | 8/2002 | Kohayakawa |
| 2002/0188203 | A1 | 12/2002 | Smith et al. |
| 2003/0018271 | A1 | 1/2003 | Kimble |
| 2003/0052105 | A1 | 3/2003 | Nagano et al. |
| 2003/0120154 | A1 | 6/2003 | Sauer et al. |
| 2003/0125629 | A1 | 7/2003 | Ustuner |
| 2003/0156260 | A1 | 8/2003 | Putilin et al. |
| 2004/0015062 | A1 | 1/2004 | Ntziachristos et al. |
| 2004/0015158 | A1 | 1/2004 | Chen et al. |
| 2004/0022421 | A1 | 2/2004 | Endoh et al. |
| 2004/0046031 | A1 | 3/2004 | Knowles et al. |
| 2004/0171923 | A1 | 9/2004 | Kalafut et al. |
| 2004/0222301 | A1 | 11/2004 | Willins et al. |
| 2004/0237051 | A1 | 11/2004 | Clauson |
| 2005/0017924 | A1 | 1/2005 | Utt et al. |
| 2005/0033145 | A1 | 2/2005 | Graham et al. |
| 2005/0043596 | A1 | 2/2005 | Chance |
| 2005/0047134 | A1 | 3/2005 | Mueller et al. |
| 2005/0085732 | A1 | 4/2005 | Sevick-Muraca et al. |
| 2005/0085802 | A1 | 4/2005 | Gruzdev et al. |
| 2005/0113650 | A1 | 5/2005 | Pacione et al. |
| 2005/0131291 | A1 | 6/2005 | Floyd et al. |
| 2005/0135102 | A1 | 6/2005 | Gardiner et al. |
| 2005/0141069 | A1 | 6/2005 | Wood et al. |
| 2005/0143662 | A1 | 6/2005 | Marchitto et al. |
| 2005/0146765 | A1 | 7/2005 | Turner et al. |
| 2005/0154303 | A1 | 7/2005 | Walker et al. |
| 2005/0157939 | A1 | 7/2005 | Arsenault et al. |
| 2005/0161051 | A1 | 7/2005 | Pankratov et al. |
| 2005/0168980 | A1 | 8/2005 | Dryden et al. |
| 2005/0174777 | A1 | 8/2005 | Cooper et al. |
| 2005/0175048 | A1 | 8/2005 | Stern et al. |
| 2005/0187477 | A1 | 8/2005 | Serov et al. |
| 2005/0215875 | A1 | 9/2005 | Khou |
| 2005/0265586 | A1 | 12/2005 | Rowe et al. |
| 2005/0281445 | A1 | 12/2005 | Marcotte et al. |
| 2006/0007134 | A1 | 1/2006 | Ting |
| 2006/0020212 | A1 | 1/2006 | Xu et al. |
| 2006/0025679 | A1 | 2/2006 | Viswanathan et al. |
| 2006/0052690 | A1 | 3/2006 | Sirohey et al. |
| 2006/0081252 | A1 | 4/2006 | Wood |
| 2006/0100523 | A1 | 5/2006 | Ogle et al. |
| 2006/0103811 | A1 | 5/2006 | May et al. |
| 2006/0122515 | A1 | 6/2006 | Zeman et al. |
| 2006/0129037 | A1 | 6/2006 | Kaufman et al. |
| 2006/0129038 | A1 | 6/2006 | Zelenchuk et al. |
| 2006/0151449 | A1 | 7/2006 | Warner, Jr. et al. |
| 2006/0173351 | A1 | 8/2006 | Marcotte et al. |
| 2006/0184040 | A1 | 8/2006 | Keller et al. |
| 2006/0206027 | A1 | 9/2006 | Malone |
| 2006/0232660 | A1 | 10/2006 | Nakajima et al. |
| 2006/0253010 | A1 | 11/2006 | Brady et al. |
| 2006/0271028 | A1 | 11/2006 | Altshuler et al. |

(56) References Cited

U.S. PATENT DOCUMENTS

| | | | |
|---|---|---|---|
| 2006/0276712 | A1 | 12/2006 | Stothers |
| 2007/0015980 | A1 | 1/2007 | Numada |
| 2007/0016079 | A1 | 1/2007 | Freeman et al. |
| 2007/0070302 | A1 | 3/2007 | Govorkov et al. |
| 2007/0115435 | A1 | 5/2007 | Rosendaal |
| 2007/0176851 | A1 | 8/2007 | Willey et al. |
| 2007/0238957 | A1 | 10/2007 | Yared |
| 2008/0045841 | A1 | 2/2008 | Wood et al. |
| 2008/0147147 | A1 | 6/2008 | Griffiths et al. |
| 2008/0194930 | A1 | 8/2008 | Harris et al. |
| 2009/0018414 | A1 | 1/2009 | Toofan |
| 2009/0171205 | A1 | 7/2009 | Kharin et al. |
| 2010/0051808 | A1 | 3/2010 | Zeman et al. |
| 2010/0061598 | A1 | 3/2010 | Seo |
| 2010/0087787 | A1 | 4/2010 | Woehr et al. |
| 2010/0177184 | A1 | 7/2010 | Berryhill et al. |
| 2010/0312120 | A1 | 12/2010 | Meier |
| 2011/0275932 | A1 | 11/2011 | Leblond et al. |
| 2013/0147916 | A1 | 6/2013 | Bennett et al. |
| 2014/0039309 | A1 | 2/2014 | Harris et al. |
| 2014/0046291 | A1 | 2/2014 | Harris et al. |

FOREIGN PATENT DOCUMENTS

| | | | |
|---|---|---|---|
| GB | 1507329 | | 4/1978 |
| JP | S60-108043 | A | 6/1985 |
| JP | 04-042944 | | 2/1992 |
| JP | 07-255847 | | 10/1995 |
| JP | 08-023501 | A | 1/1996 |
| JP | 08-164123 | | 6/1996 |
| JP | 2000-316866 | A | 11/2000 |
| JP | 2002-328428 | A | 11/2002 |
| JP | 2002-345953 | A | 12/2002 |
| JP | 2004-237051 | | 8/2004 |
| JP | 2004-329786 | A | 11/2004 |
| KR | 2003-0020152 | A | 3/2003 |
| WO | WO 1994 22370 | | 10/1994 |
| WO | WO 1996 39925 | | 12/1996 |
| WO | WO 1998 26583 | | 6/1998 |
| WO | WO 1999 48420 | | 9/1999 |
| WO | WO 2001-82786 | | 11/2001 |
| WO | WO 2003-009750 | | 2/2003 |
| WO | WO 2005-053773 | | 6/2005 |
| WO | WO 2007-078447 | | 7/2007 |

OTHER PUBLICATIONS

Nikbin, Darius, "IPMS Targets Colour Laser Projectors," Optics & Laser Europe, Mar. 1006, Isue 137, p. 11.

http://sciencegeekgirl.wordpress.com/category/science-myths/page/2/ Myth 7: Blood is Blue.

http://www.exploratorium.edu/sports/hnds_up/hands6.html "Hands Up! To Do & Notice: Getting the Feel of Your Hand".

http://www.wikihow.com/See-Blook-Veins-in-Your-Hand-With-a-Flashlight "How to See Blood Veins in Your Hand With a Flashlight".

(Initial/Perpendicular Positioning of Device to Vein Flow Direction, for Display Quality)

(Centering of Display Light Above Vein Centerline for Display Accuracy)

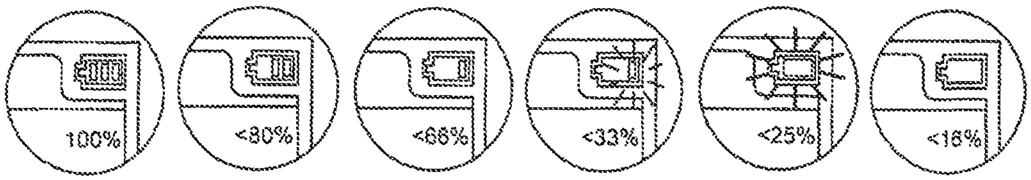
FIG. 14
(Battery Charge Indicators)
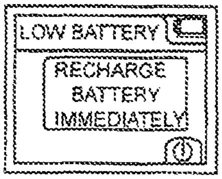
FIG. 14A
(Low Battery Message)
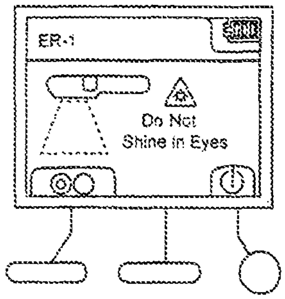
Left, Middle & Right
LCD Buttons
FIG. 15
(LCD Start Screen)
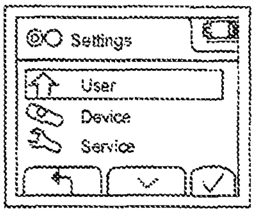
FIG. 15A
(First Menu Screen- "Settings")
| | |
|---|---|
| | Power device ON/OFF. |
| | Enter Menu mode. |
| | Scroll up/down through a menu change parameters. |
| | Move to a cofiguration setting. |
| | Select the current menu option setting.. |
| | Go back to the previous screen. |
FIG. 15B
(LCD Button Icons/Functions)

(Changing Default Vein Display Setting)

(Changing Vein Display Time-Out)

(LCD Backlight Setting Screen)

(Speaker Volume Setting Screen)

(Labeling/Naming of LCD Start Screen)

(Up/Down Arrows for Character Selection)

(Language Setting Screen)

(Returning Default Settings-
Press & Hold Middle Button and Press Left Button)

(Device-to-PC Coupling for Software Update)

(PC searches for Device)

(PC Detects/Communicates with Device)

(Device is not Detected Message)

(Successful Software Update Message)

(Message Sequence when Updating Device Software)

BATTERY COVER/ LABEL ORIENTATION
(INSIDE SURFACE)

Revision Notes

Rev 02 Add R182 10K res and C162 0.01uF cap

Make Scan switch NoPop

Rev A Change/Correct D17, R215 Agile PN

Add C4

METHOD AND SYSTEM FOR OPTIMIZING A PROJECTED VEIN IMAGE AND IDENTIFYING VEIN LOCATIONS USING VEIN SCANNER

CROSS REFERENCES TO RELATED APPLICATIONS

This is a continuation of U.S. application Ser. No. 16/595,750, filed Oct. 8, 2019, which is a continuation of U.S. application Ser. No. 15/678,355, filed Aug. 16, 2017, now issued as U.S. Pat. No. 10,518,046, which is a continuation of U.S. application Ser. No. 14/718,422, filed May 21, 2015, now issued as U.S. Pat. No. 9,789,267, which is a continuation of U.S. application Ser. No. 13/778,426, filed Feb. 27, 2013, now issued as U.S. Pat. No. 9,061,109, which is a continuation of U.S. application Ser. No. 12/804,506, filed Jul. 22, 2010, now issued as U.S. Pat. No. 8,463,364, which claims priority on U.S. Provisional Application Ser. No. 61/271,587, filed Jul. 22, 2009, all disclosures of which are incorporated herein by reference.

BACKGROUND OF THE INVENTION

Drawing blood and administering intravenous medication using medical devices including but not limited to catheters are common medical procedures, but conventional methods to perform these procedures have several limitations. First a vein must be found. Conventional methods of locating an appropriate vein or artery include restricting the blood supply to the location of the body so that the blood pressure in that area is greater, which results in the patient's veins becoming more visible. This is often accomplished by the use of a temporary tourniquet, which can result in extreme discomfort to the patient. Even after the temporary tourniquet is applied and certain veins are exposed, a medical professional may still not be able to find an appropriate vein. This problem can occur more readily in elderly patients and patients with low blood pressure. Thus, there is a need for a non-invasive method for locating veins.

SUMMARY OF THE INVENTION

The present invention is directed towards a portable hand-held medical apparatus that uses infrared light to detect veins beneath the skin, then illuminating the position of the veins on the skin surface directly above the veins using visible light. When the apparatus is held a distance above the outer surface of the skin, veins appear vastly different than the surrounding tissue, and veins that are otherwise undetectable because of their depth in the tissue are safely located and mapped on the patient's skin. Vein's will be accessed more readily and with greater confidence and as such, venipuctures will go more smoothly while vasculature shows up clearly on the skin's surface, making it easy to select the best vein to collect a blood sample from or administer medications to. Qualified medical personnel can observe the displayed vasculature to assist them in finding a vein of the right size and position for venipuncture.

BRIEF DESCRIPTION OF THE DRAWINGS

FIG. 14 is a series of images identifying different indications the LCD display will provide for different battery power levels.

FIG. 14A illustrates a Low Battery message displayed on the LCD of the device.

FIG. 15 is a screen shot of the LCD start screen.

FIG. 15A is a screen shot of the LCD when utilized for making configuration setting changes.

FIG. 15B shows all of the LCD button icons and their functionality.

DETAILED DESCRIPTION OF THE INVENTION

Figure 1:
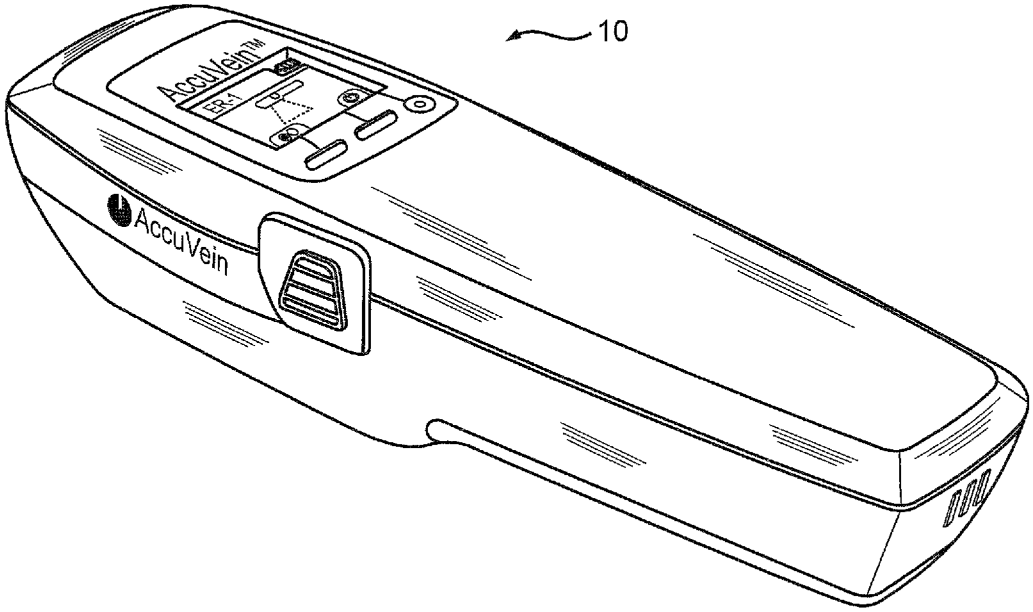
FIG. 1 is a perspective view of the apparatus of the present invention.
Figure 2:
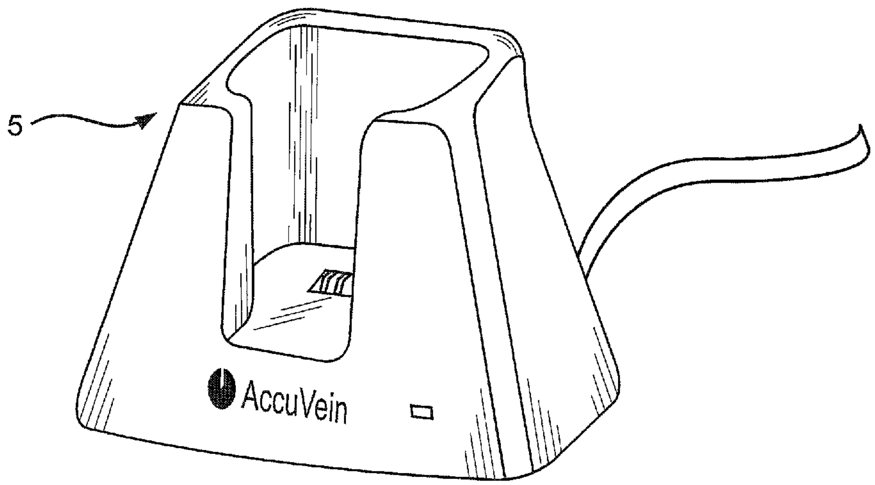
FIG. 2 is a perspective view of a charging cradle for the apparatus of FIG. 1.
Figure 3:
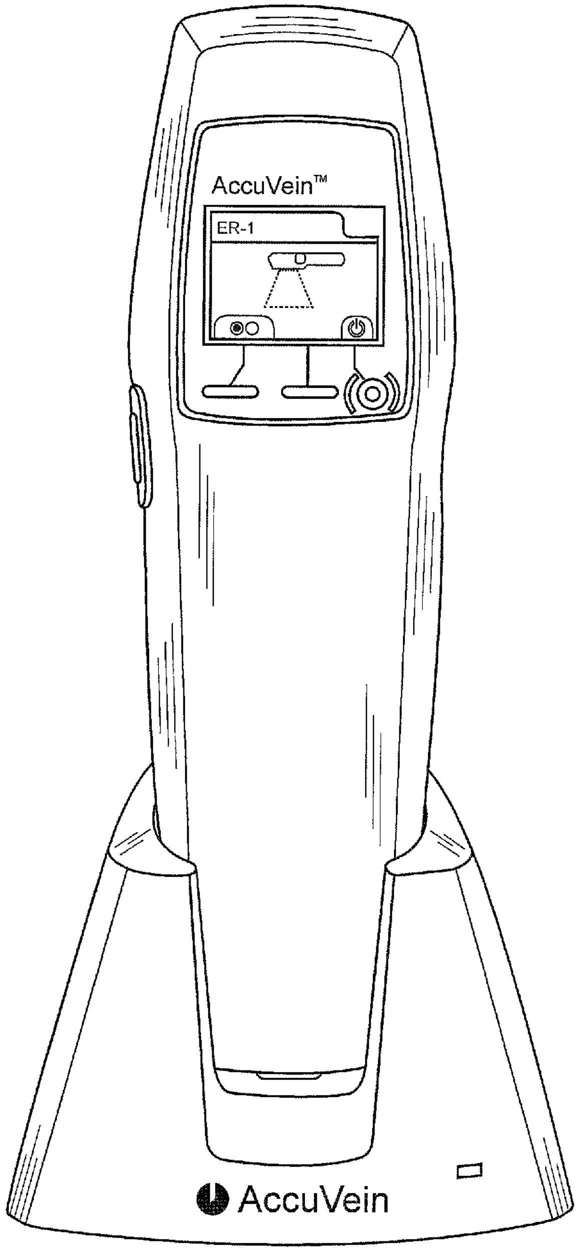
FIG. 3 is a front view of the apparatus of FIG. 1, while being charged in the cradle of FIG. 2.
Figure 4:
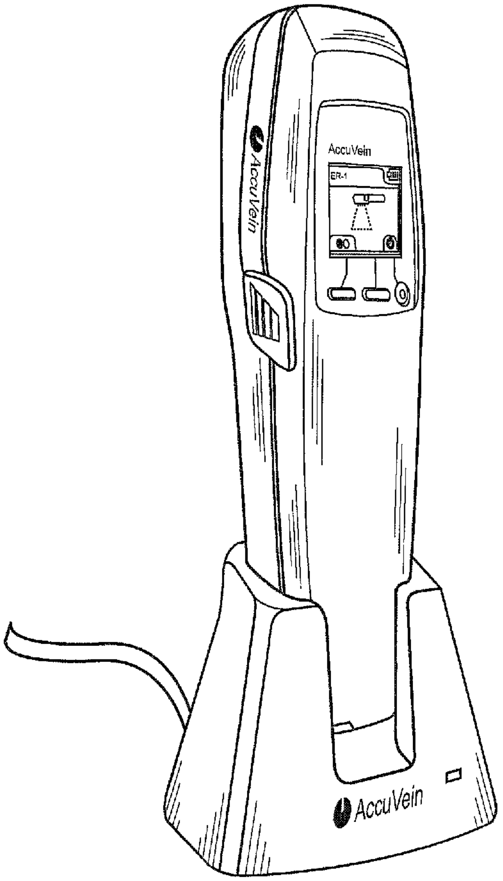
FIG. 4 is a perspective view of the apparatus of FIG. 1 being charged in the cradle of FIG. 2.

The present invention is directed to an apparatus 10 (FIG. 1) that is an opto-electronic device that assists medical practitioners by locating veins and then projecting an image of those veins directly on a patient's skin. The apparatus may be portable, hand held, and battery powered. However in an alternative embodiment an external power supply may be used to power the apparatus. The apparatus operates by using infrared light to detect veins beneath the skin, and then illuminates the position of the veins on the skin surface directly above the veins using visible light. The apparatus 10 may be battery powered, and rechargeable using a cradle 5 (FIG. 2), and may generally be stored therein (FIGS. 3-4).

Figure 30:
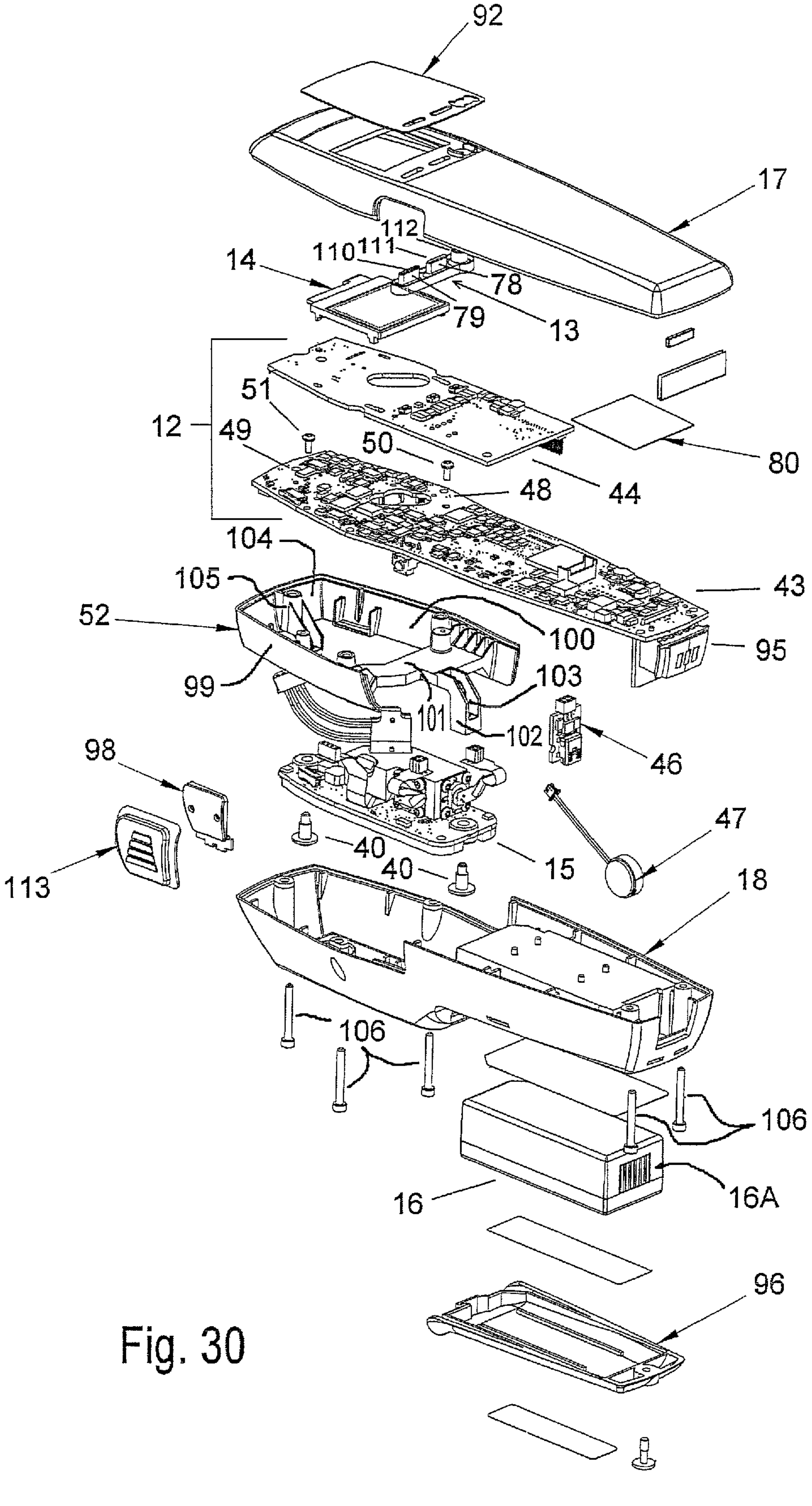
FIG. 30 is an exploded view of the apparatus of the present invention.

The apparatus 10 generally comprises a housing 11, internal circuitry 12, keypad 13, display 14, scanner assembly 15, and battery pack 16. The housing 11 may generally comprise a top section 17 and bottom section 18 as shown in FIG. 30. Although a specific shape for the housing and the top and bottom sections are shown it will be appreciated that this is merely a representative example and other configurations are intended to be included in the invention. The function of the housing 11 is to for example provide a location to mount the internal circuitry 12, keypad 13, display 14, scanner assembly 15, and battery 16. A general embodiment of the housing will be disclosed, but it will be generally understood that modifications to the housing to accommodate different internal circuitry, keypad, display, laser assembly, and battery are within the scope of this invention. In addition, if other features are desired the housing may be modified to include those features.

Figure 31:
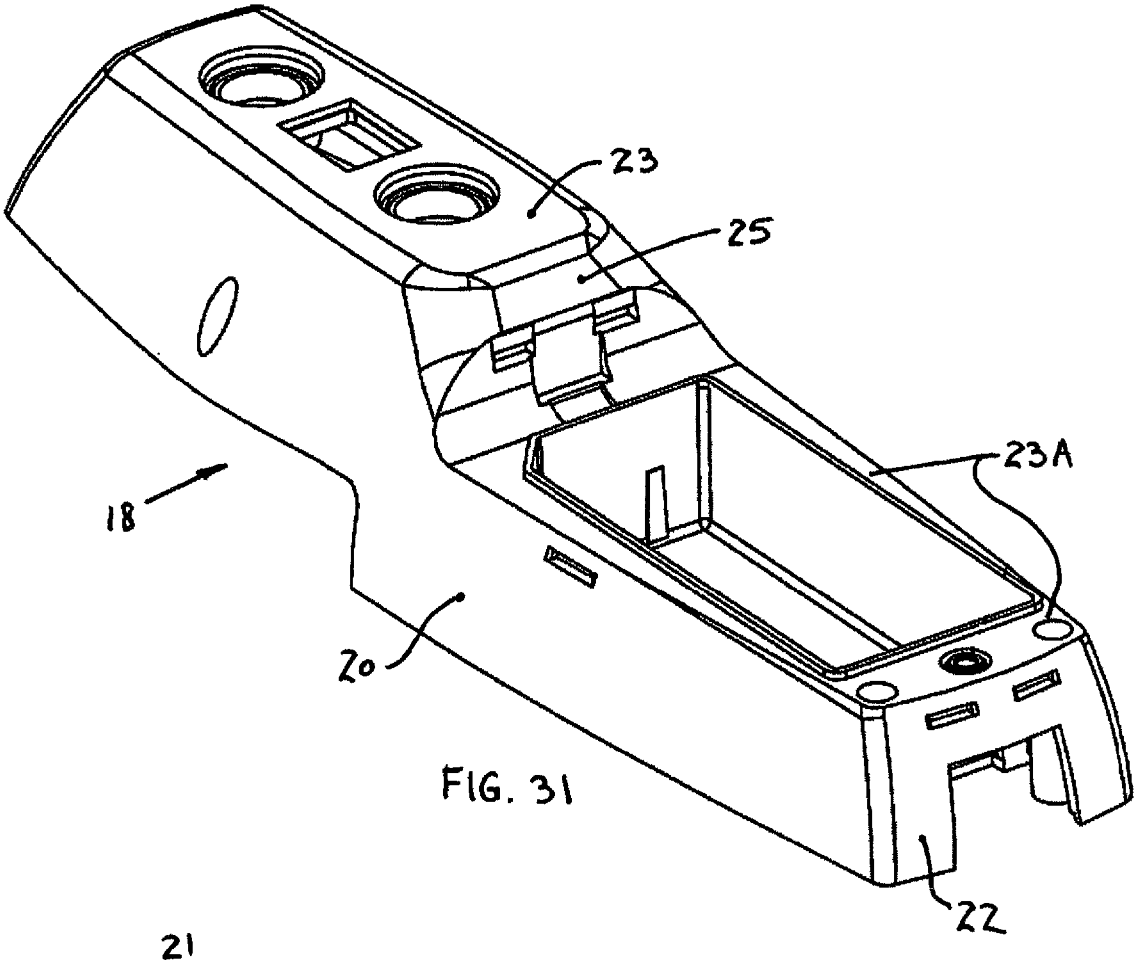
FIG. 31 shows a bottom perspective view of the bottom section of the housing.
Figure 32:
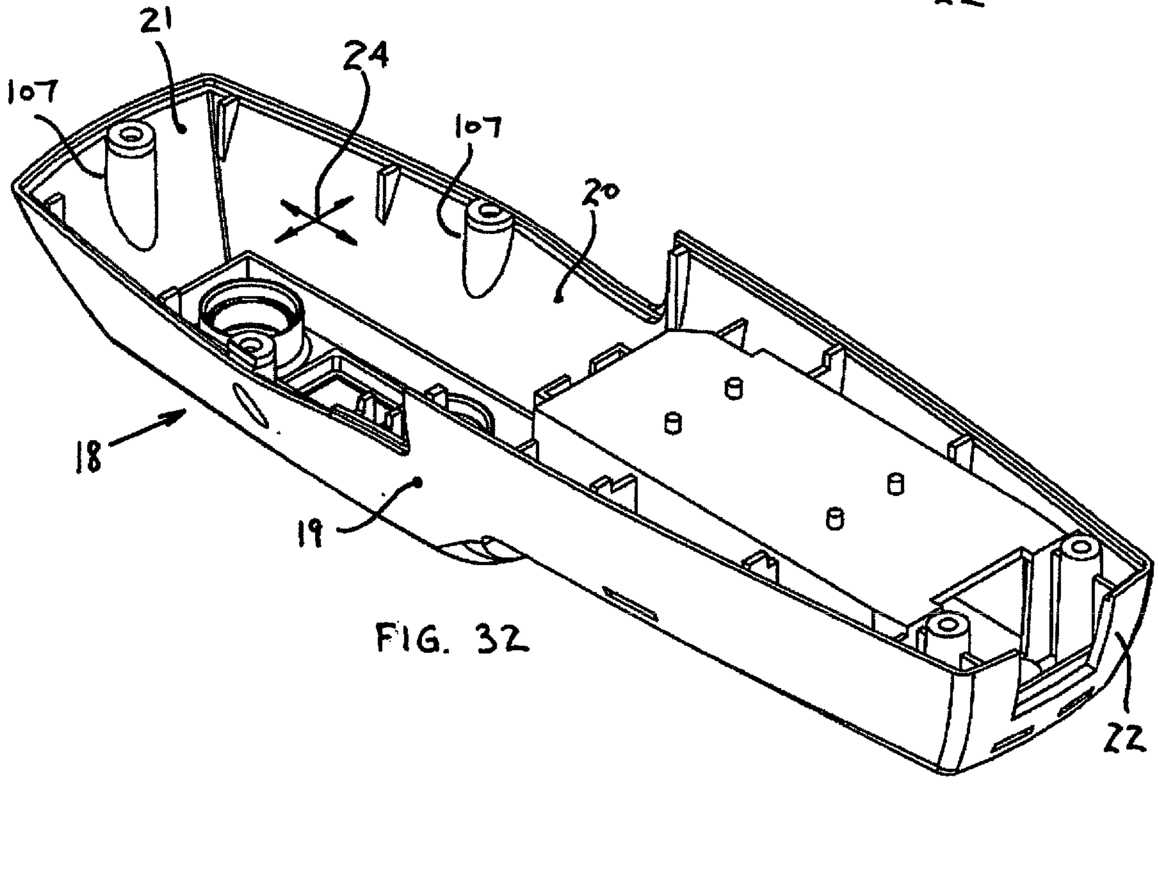
FIG. 32 shows a top perspective view of the bottom section of the housing.
Figures 33, 34, 35, 36:
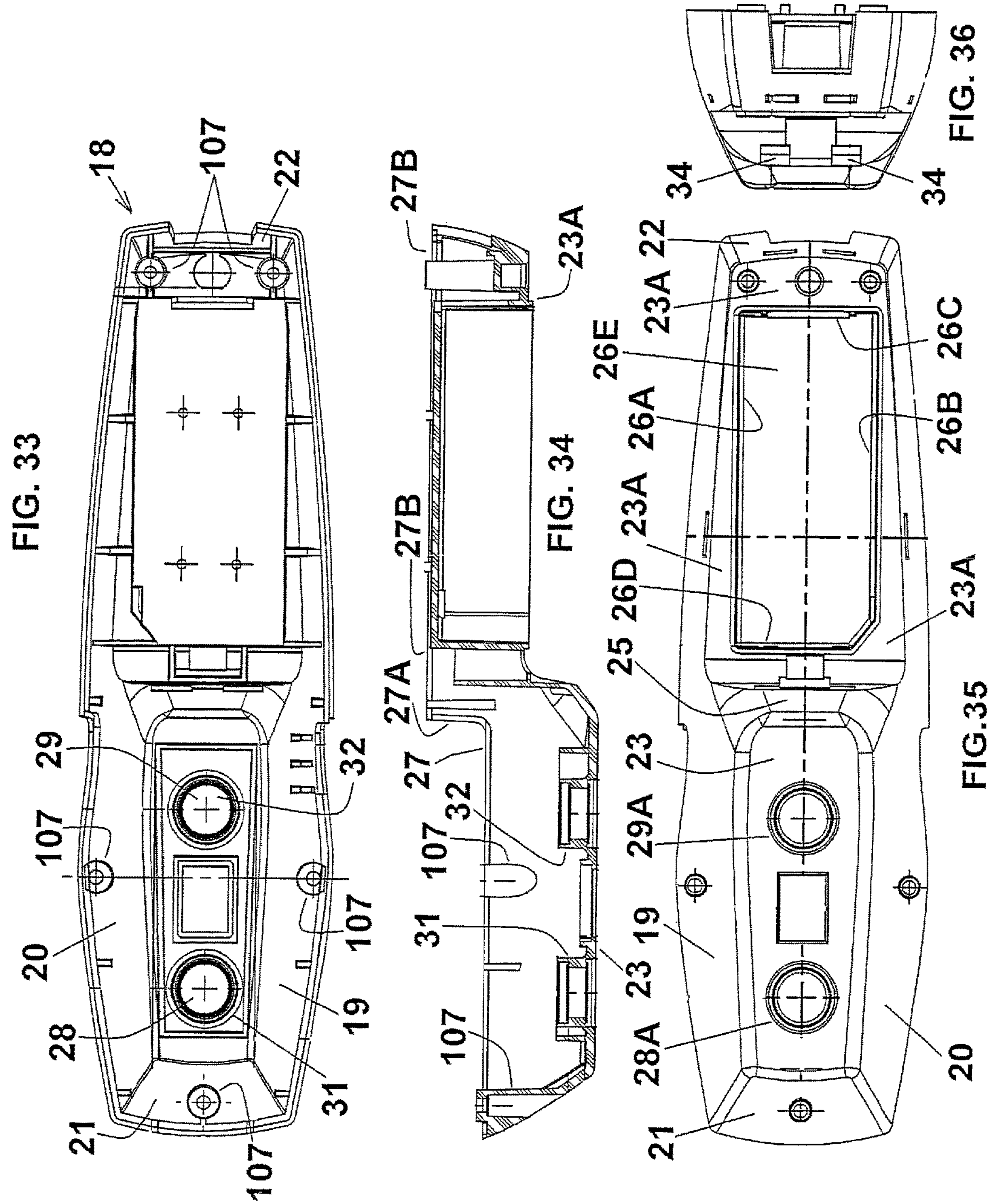
FIG. 33 is a top view of the bottom section of the housing.
FIG. 34 is a cross-sectional view of the bottom section of the housing.
FIG. 35 is a bottom view of the bottom section of the housing.
FIG. 36 is an end view of the bottom section of the housing.
Figure 40:
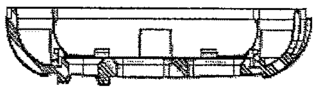
FIG. 40 is a first section cut through the top section of the housing.
Figure 39A:
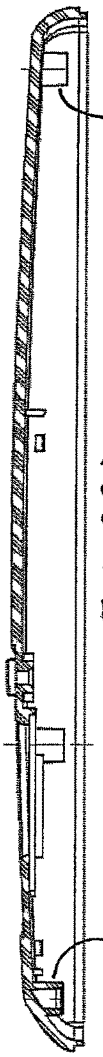
FIG. 39A is a cross sectional view through the apparatus of FIG. 39.

The housing 11 may be comprised generally of a top section 17 and a bottom section 18. FIGS. 31 and 32 show a representation of one embodiment of the bottom housing section 18 of the housing 11, in perspective views, and which are detailed in FIGS. 33-36. As seen in FIGS. 31 and 32, the bottom housing section 18 generally comprises a left sidewall 19 and a right sidewall 20, which are connected by a front wall 22 and rear wall 23. The exterior surfaces of those walls, which may be handled by the user, are seen in FIG. 35, while the interior surfaces of those walls, which may receive the electronic circuitry and other components, are visible in FIG. 33.

The walls 19-22 may each be angled, and may be so angled simply for aesthetic reasons, or for better handling by a user, or the angling (draft) may be the result of the manufacturing process used to create the housing bottom section 18, possibly being a casting process, a forging process, or a plastic injection molding process. However, the walls 19-22 need not be so angled, and the housing bottom section 18 may also be manufactured using any other suitable manufacturing process or processes, including, but not limited to, machining of the part. One end of the angled walls 19-22 may terminate in a generally flat bottom wall 23, to create an internal cavity 24. The generally flat bottom wall 23 may transition, using transition wall 25, into another generally flat wall 23A. Wall 23A may be interrupted by a series of internal walls (26A, 26B, 26C, and 26D) extending therefrom and an internal top wall 26E connecting those internal side walls, to form a compartment that may house the battery 16. The other end of the angled walls 19-22 may terminate in an edge 27. Edge 27, at front wall 21 and in the nearby regions of sidewalls 19 and 20, may be generally planar, but may transition into edge 27A, which serves as a transition to generally planar edge 27B that begins at rear wall 22. Each of the edges 27, 27A, and 27B of the housing bottom section 18 may have a step for receiving a corresponding protruding flange of the housing top section 17, when they are joined during assembly of the apparatus 10.

In one embodiment, the front wall 21 and sidewalls 19 and 20 of the housing bottom section 18 may have extending up towards the plane of the edge 27, one or more cylindrical members—a boss 107, which is adapted to receive mounting screws 106, and may include the use of threaded inserts for mounting of the housing top section 17 to the housing bottom section 18. It will be appreciated that other mounting means may be used, including, but not limited to, the use of a snap closure, or a post and recess combination with a friction fit therebetween.

Figure 6:
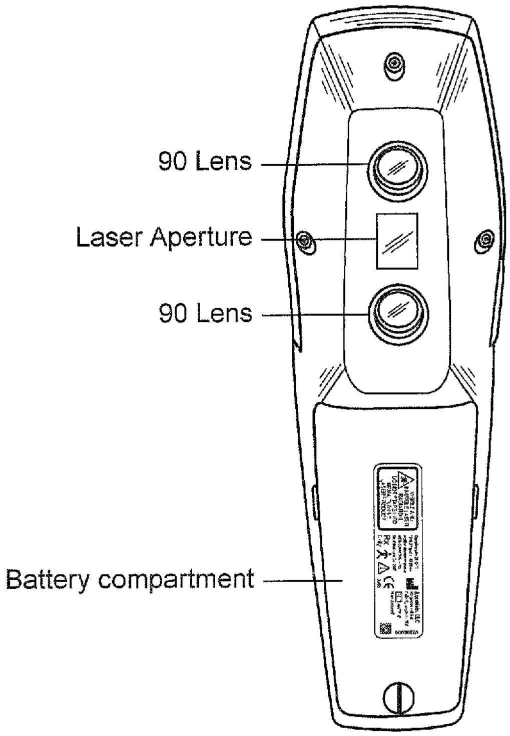
FIG. 6 is a bottom view of the apparatus of FIG. 1.
Figure 7:
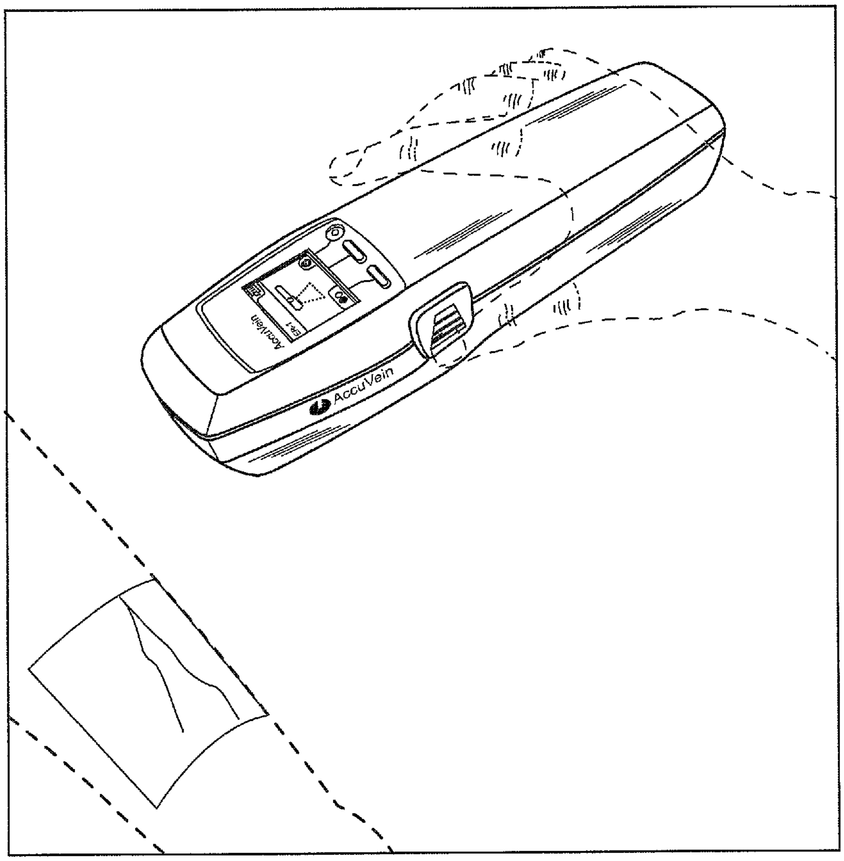
FIG. 7 is an image of a health care professional utilizing the apparatus of FIG. 1 to enhance the vein image of veins in a patient's arm.
Figure 10:
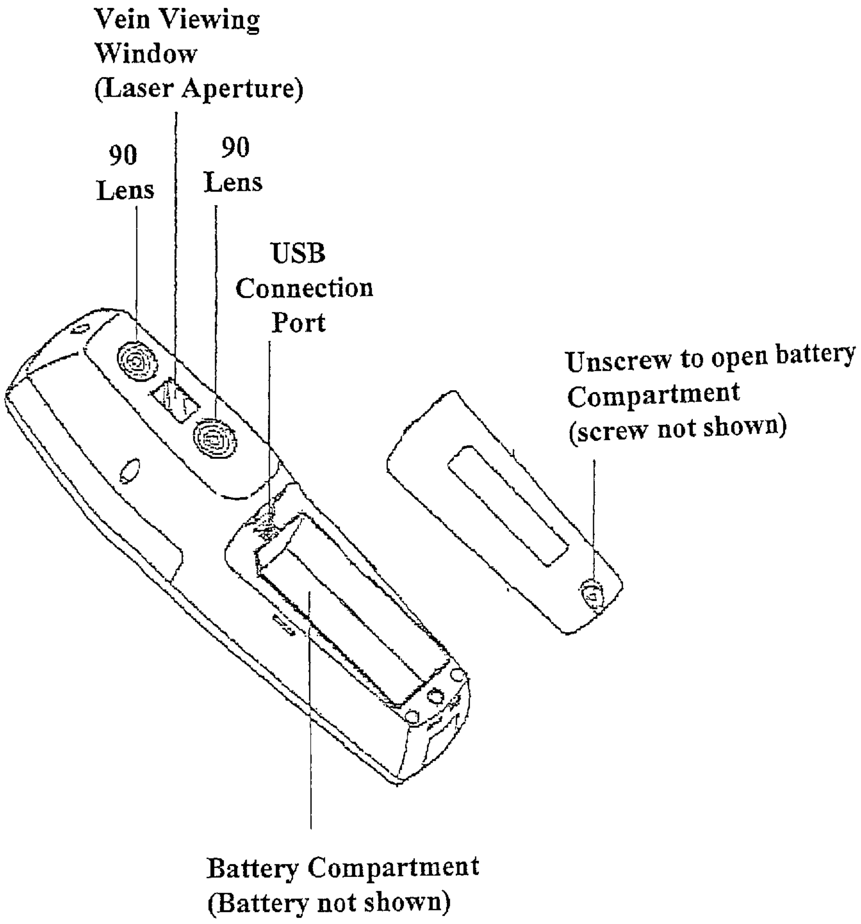
FIG. 10 is a perspective view of the apparatus of FIG. 1, with the battery cover removed to show the battery compartment.
Figure 11:
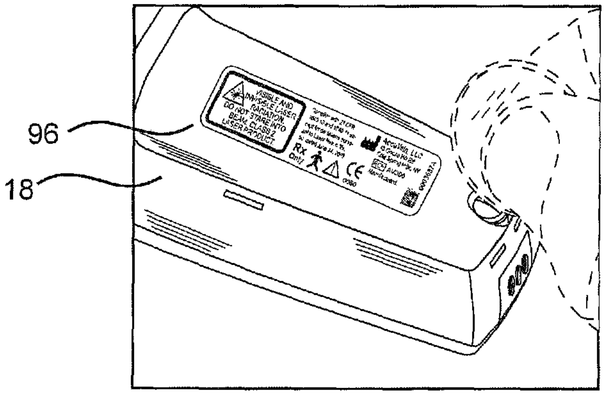
FIG. 11 is a perspective view of the apparatus showing removal of the battery cover.
Figure 12:
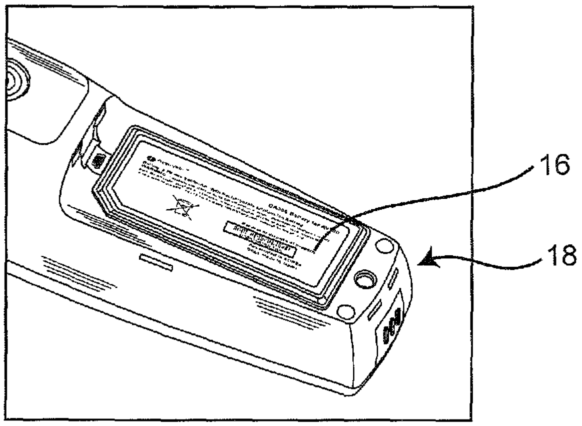
FIG. 12 is a perspective view of the apparatus with the battery cover removed, exposing the battery when properly installed in the battery compartment.

The bottom wall 23 of housing bottom section 18 may be provided with two orifices 28, and 29. On the outside surface of bottom wall 23 there may be one or more annular recesses 28A and 29A, being concentric to orifices 28 and 29, respectfully, each of which may be used to receive a lens 90 (FIGS. 6 and 10).

Protruding inward from the inside of bottom wall 23 may be cylindrical protrusions 31, and 32. Protrusions 31 and 32 may be concentric with orifices 28 and 29, respectfully, and may be adapted to receive a portion of the photodiode masks 66 and 67 of the scanner assembly 15, which are discussed later.

Figure 13:
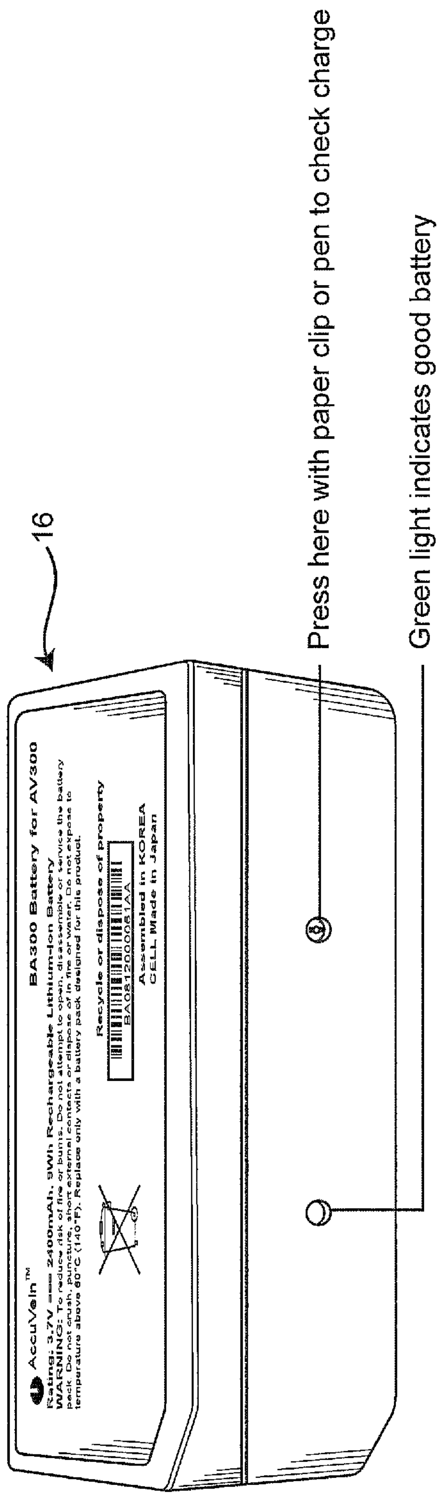
FIG. 13 is a perspective view of battery of the apparatus.
Figure 16:
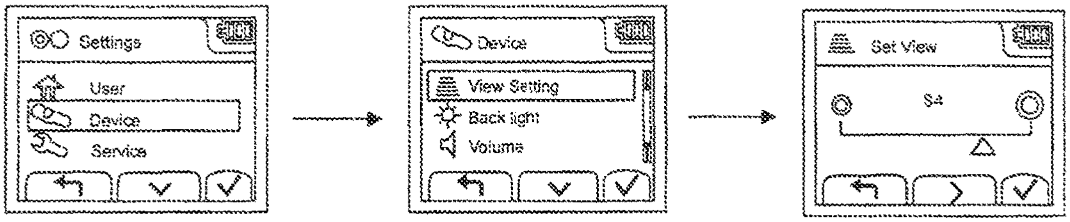
FIG. 16 is a series of screen shots of the LCD display used for modifying the default Vein Display Setting.
Figure 17:
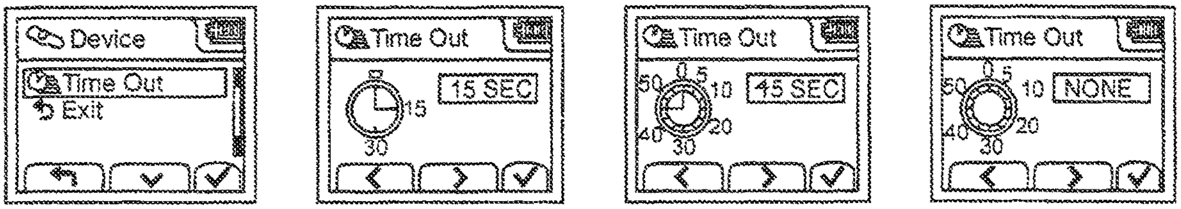
FIG. 17 is a series of screen shots of the LCD display illustrating changing of the Display Time-out interval.
Figure 18:
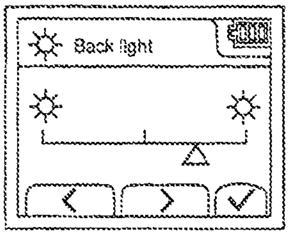
FIG. 18 is a screen shot illustrating how to change the Backlight Intensity of the apparatus.
Figure 19:
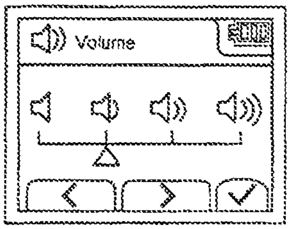
FIG. 19 is a screen shot of the LCD screen used for changing the speaker volume of the apparatus.
Figure 47:
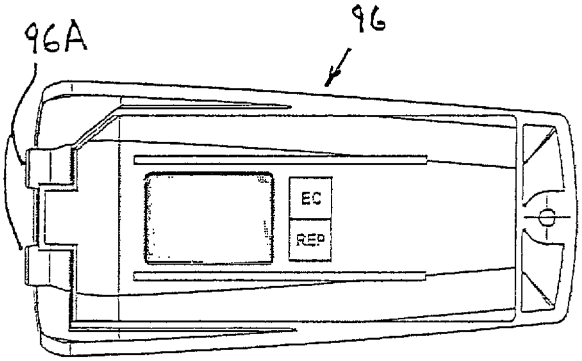
FIG. 47 is a view of the inside of the battery cover.
Figure 47A:
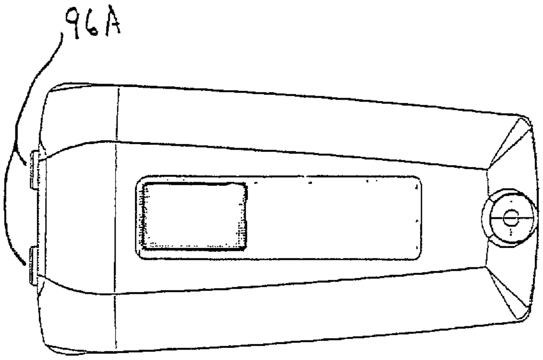
FIG. 47A is a view of the outside of the battery cover.
Figure 48A:
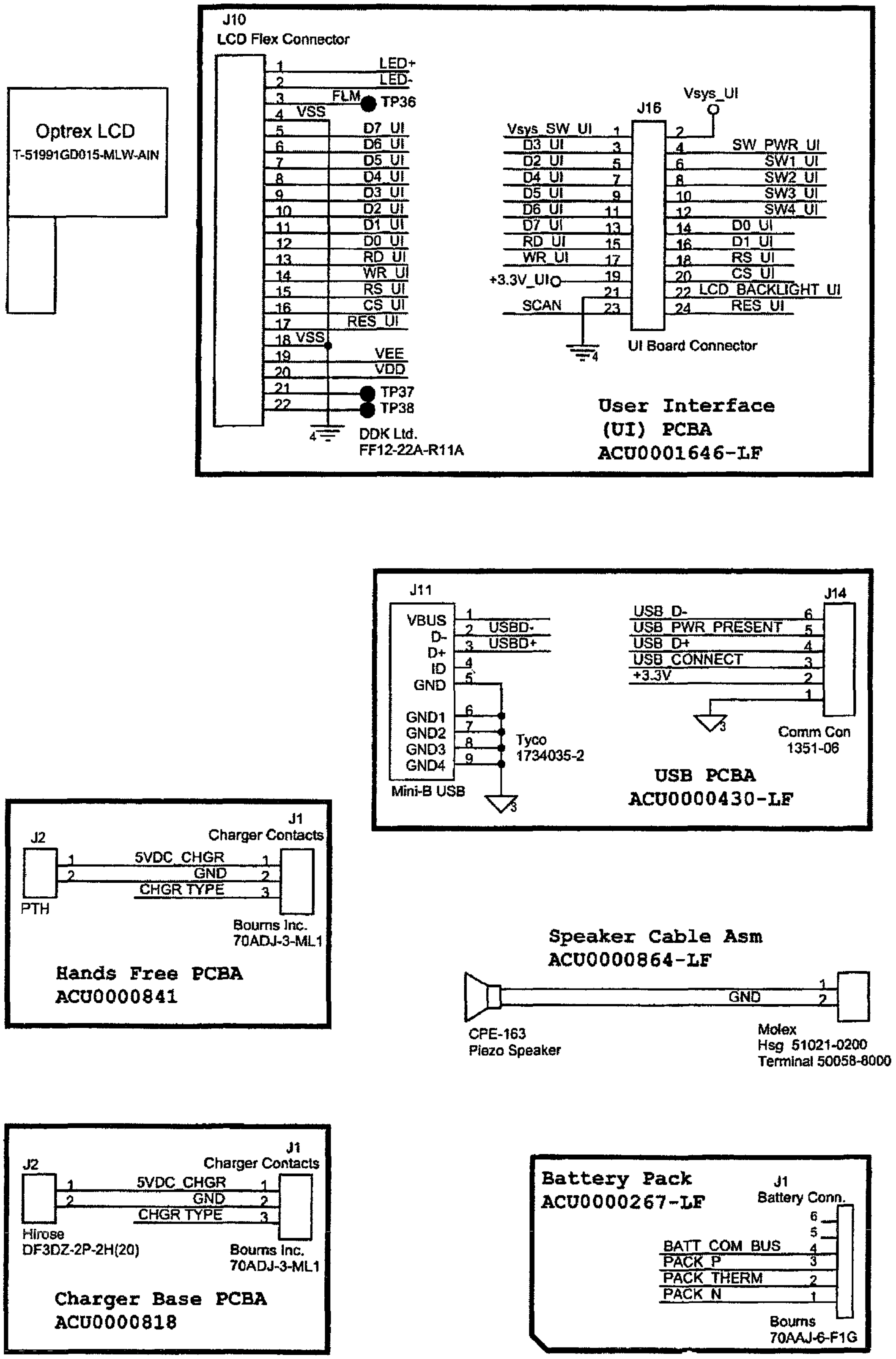
FIGS. 48A-D is a assembly level block/schematic diagram of the present invention
Figure 48B:
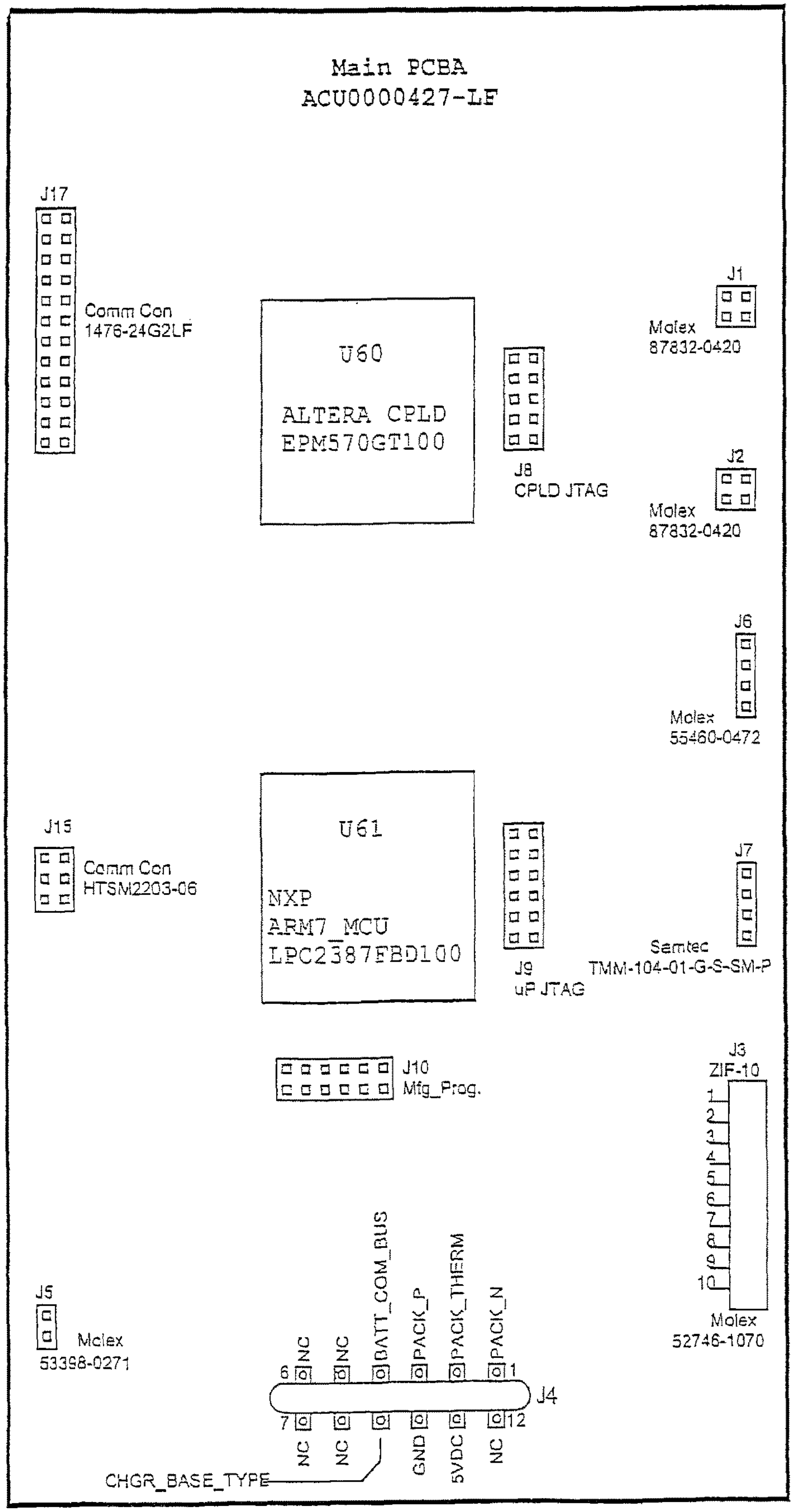
Figure 48C:
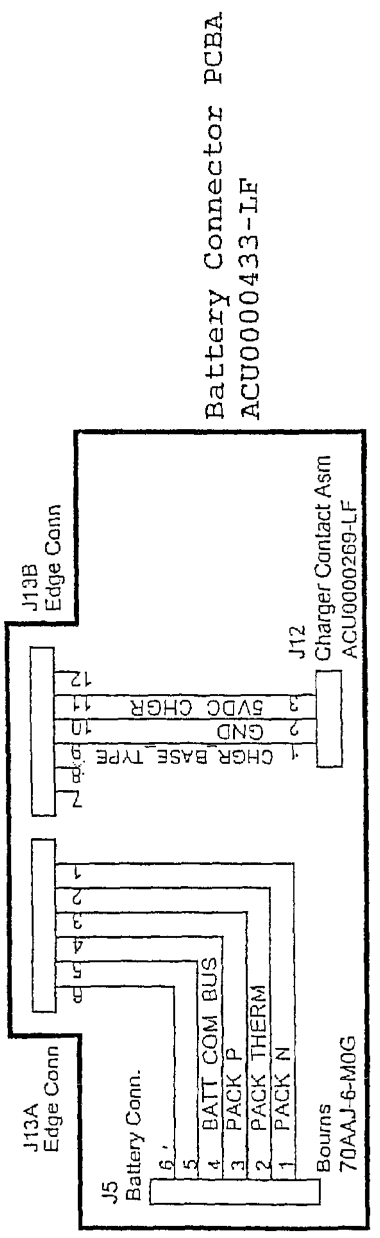
Figure 48D:
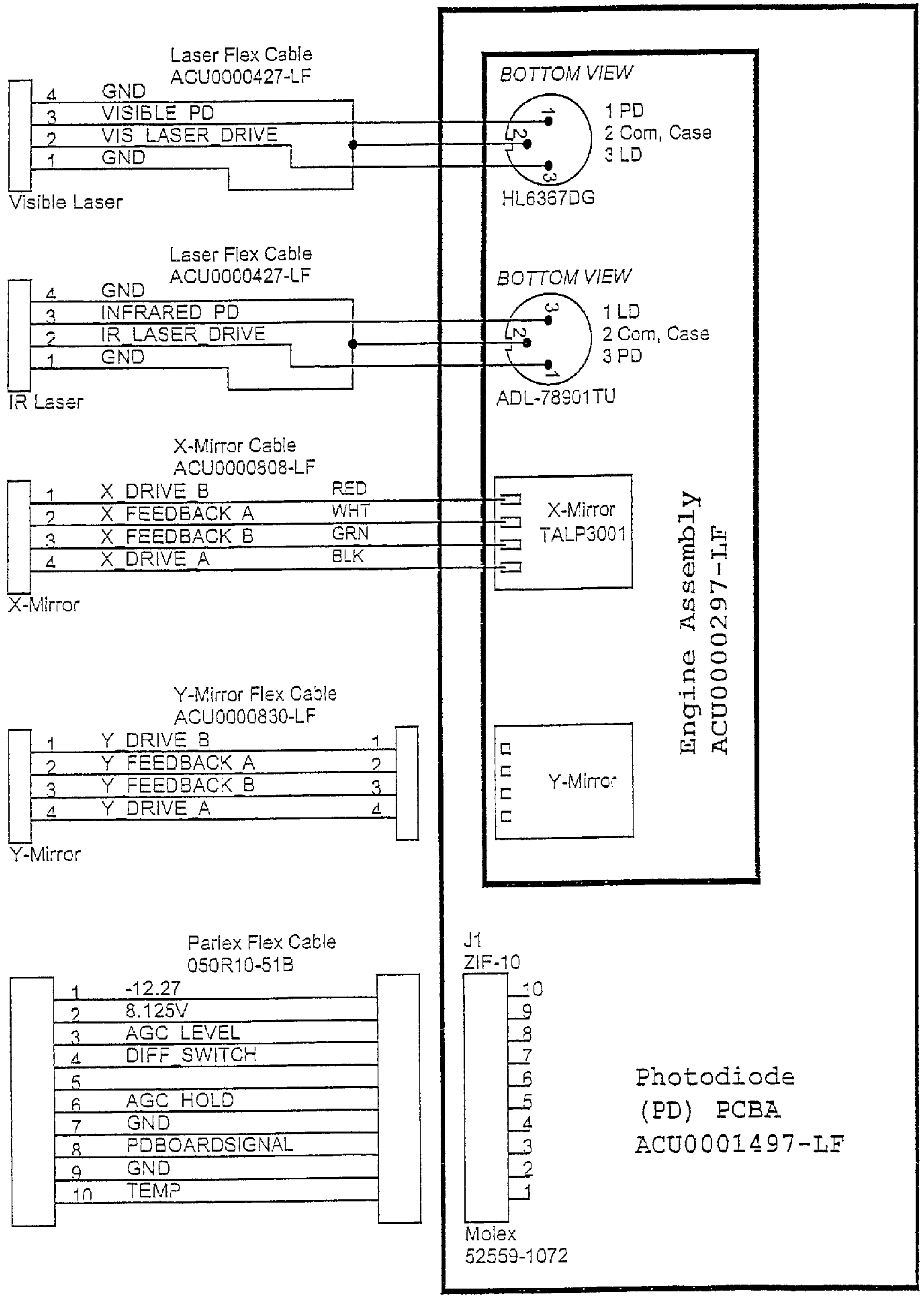
Figure 49A:
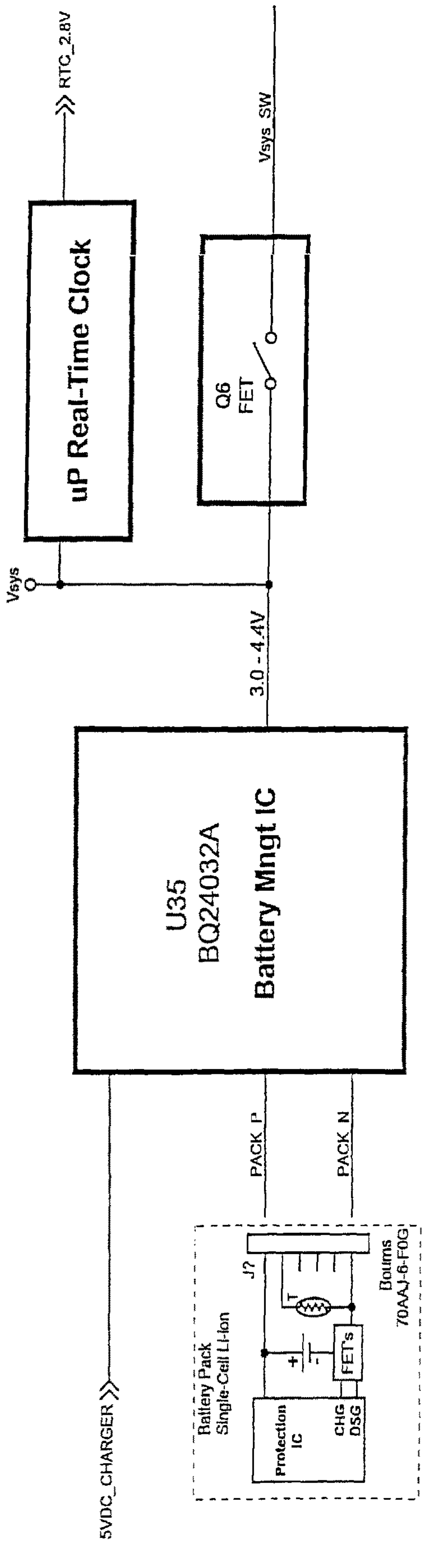
FIGS. 49A-C is an additional assembly level block diagram of the present invention.
Figure 49B:
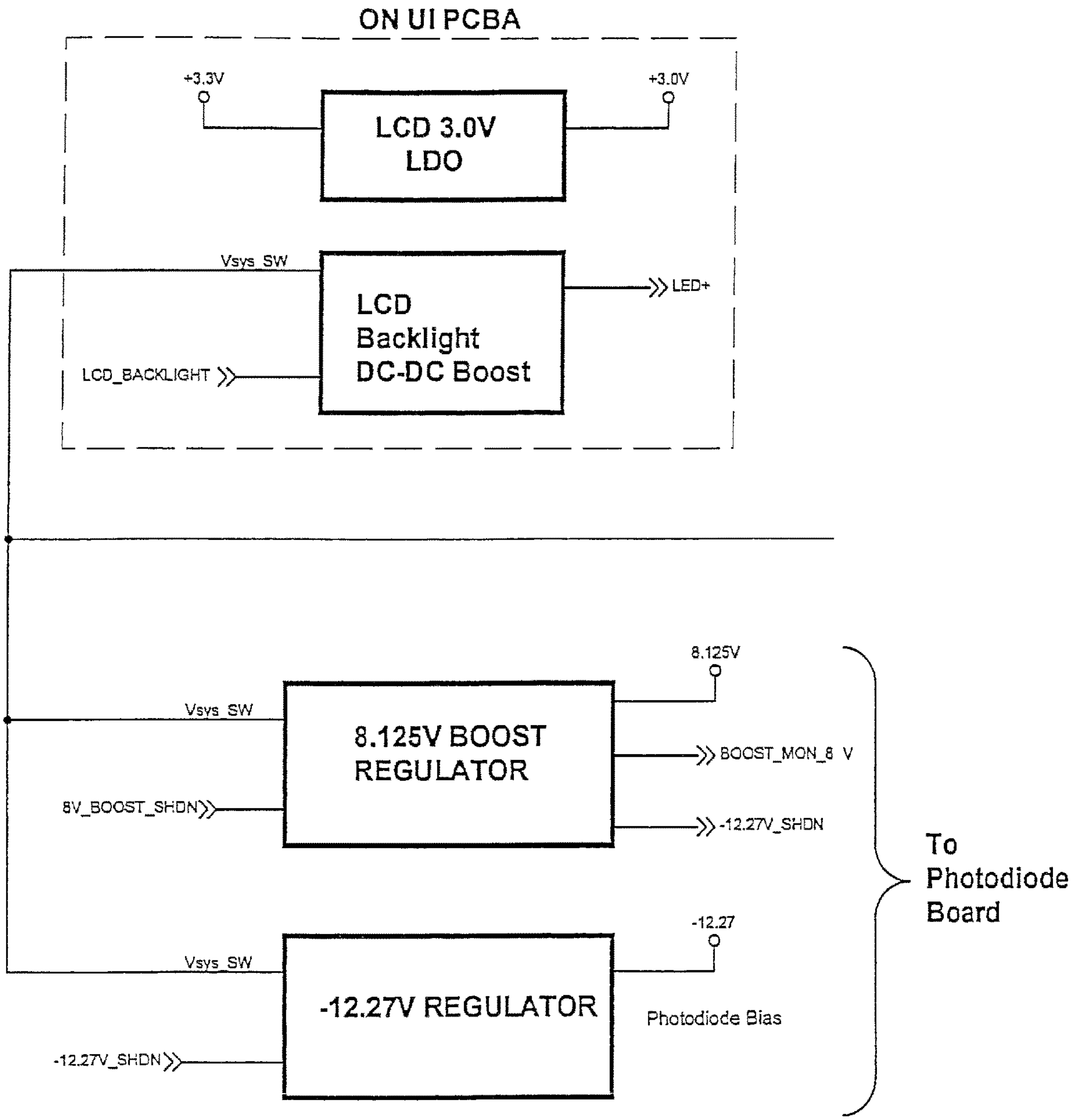
Figure 49C:
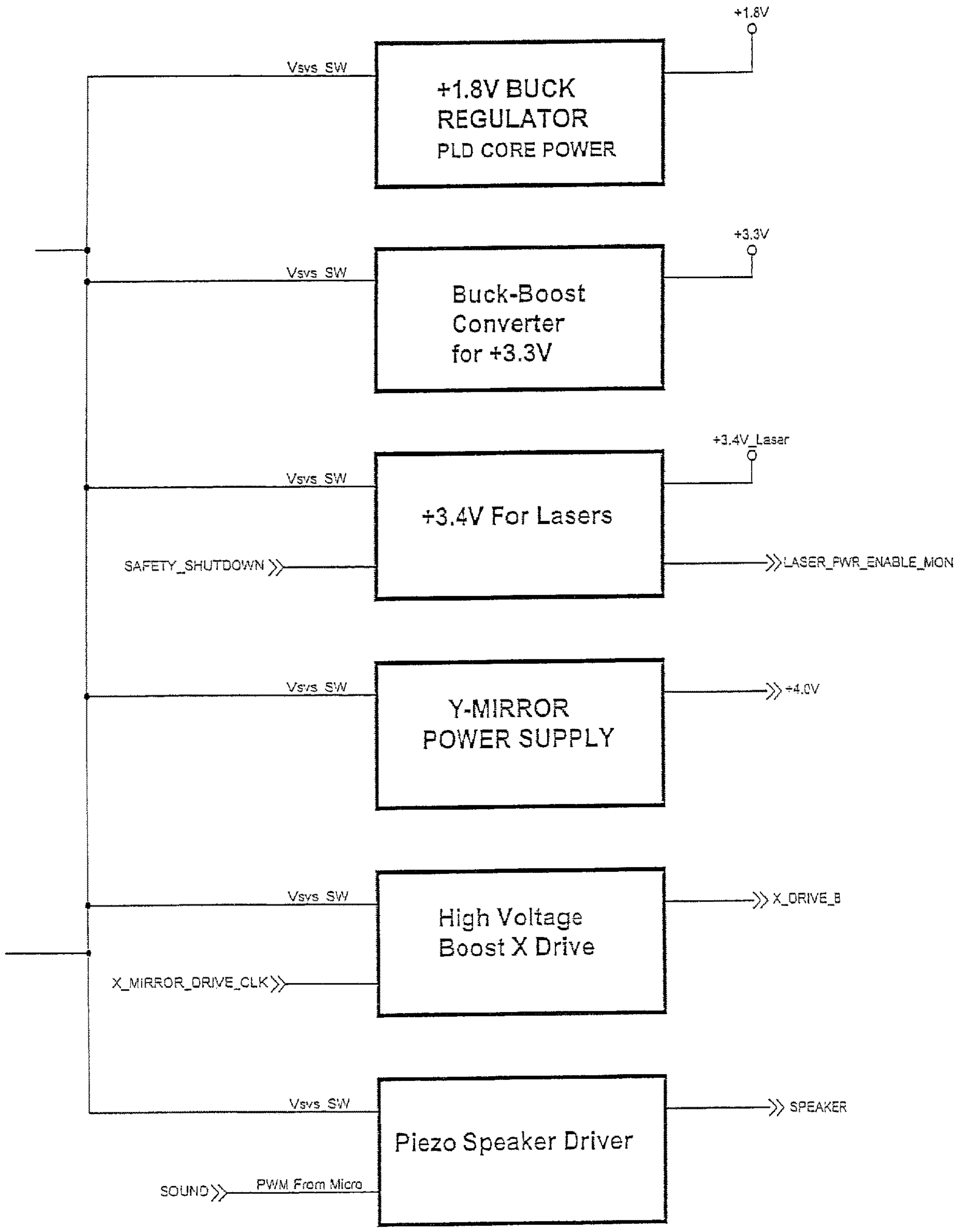
Figure 50A:
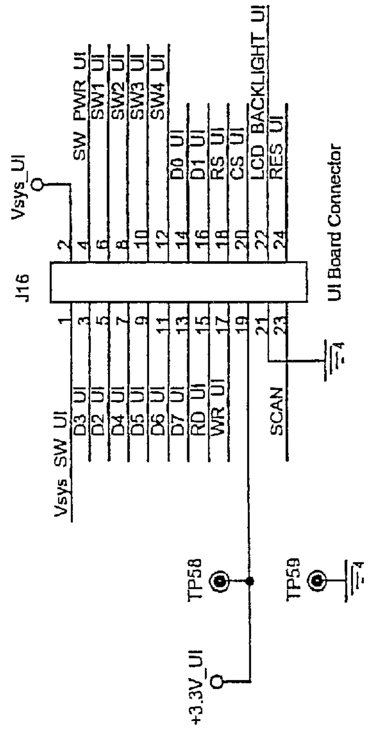
FIGS. 50A-D is a schematic of a circuit diagram of the user interface board.
Figure 50B:
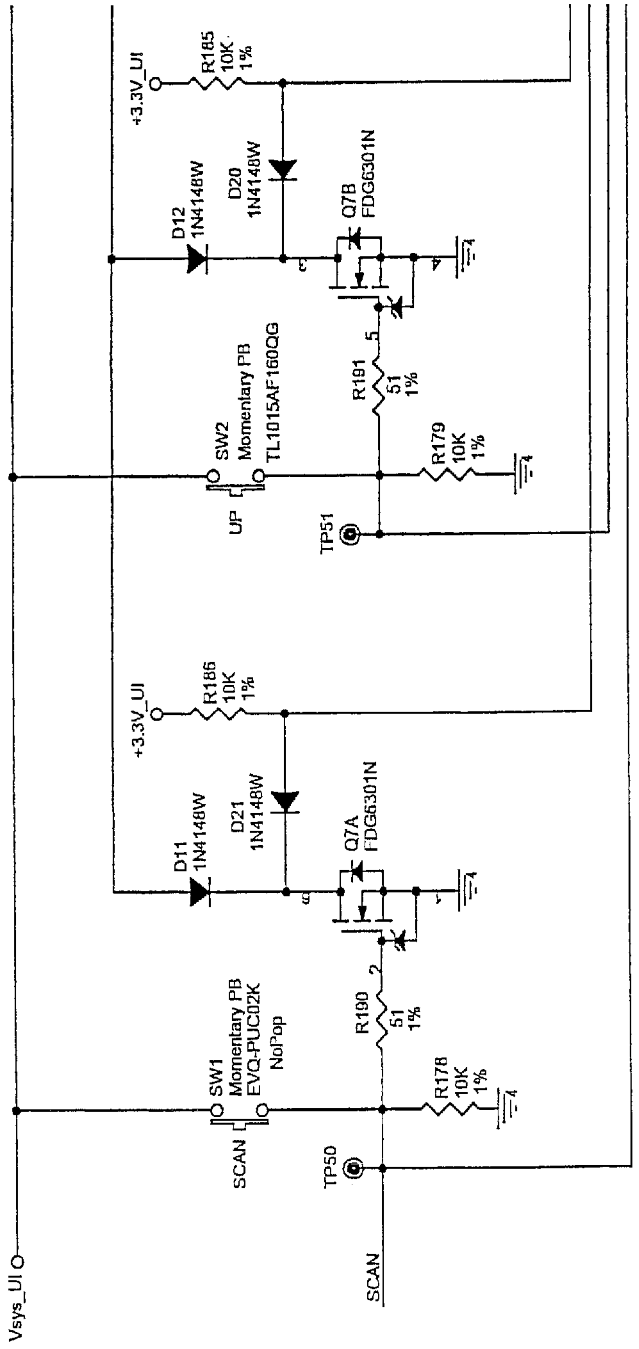
Figure 50C:
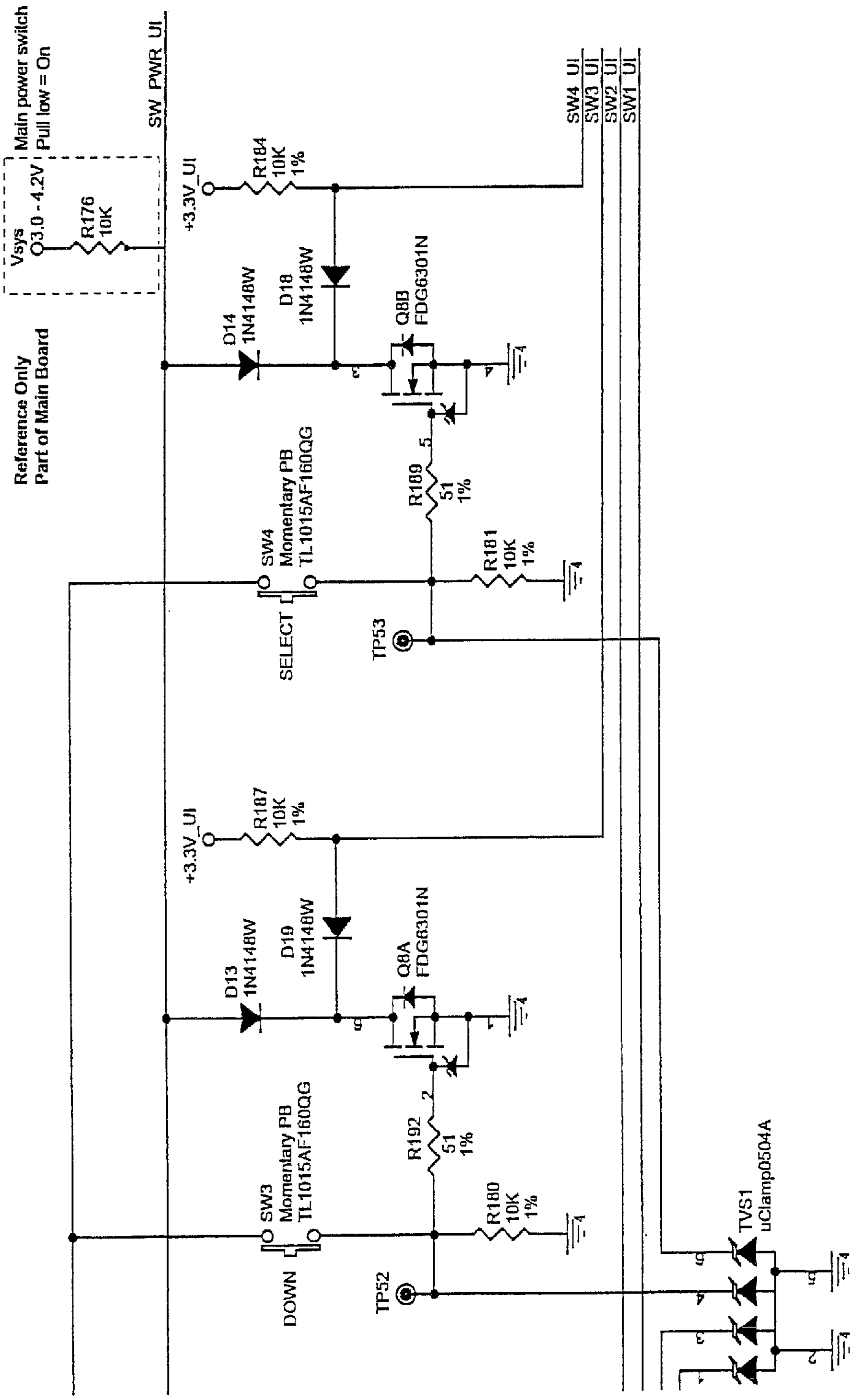
Figure 50D:
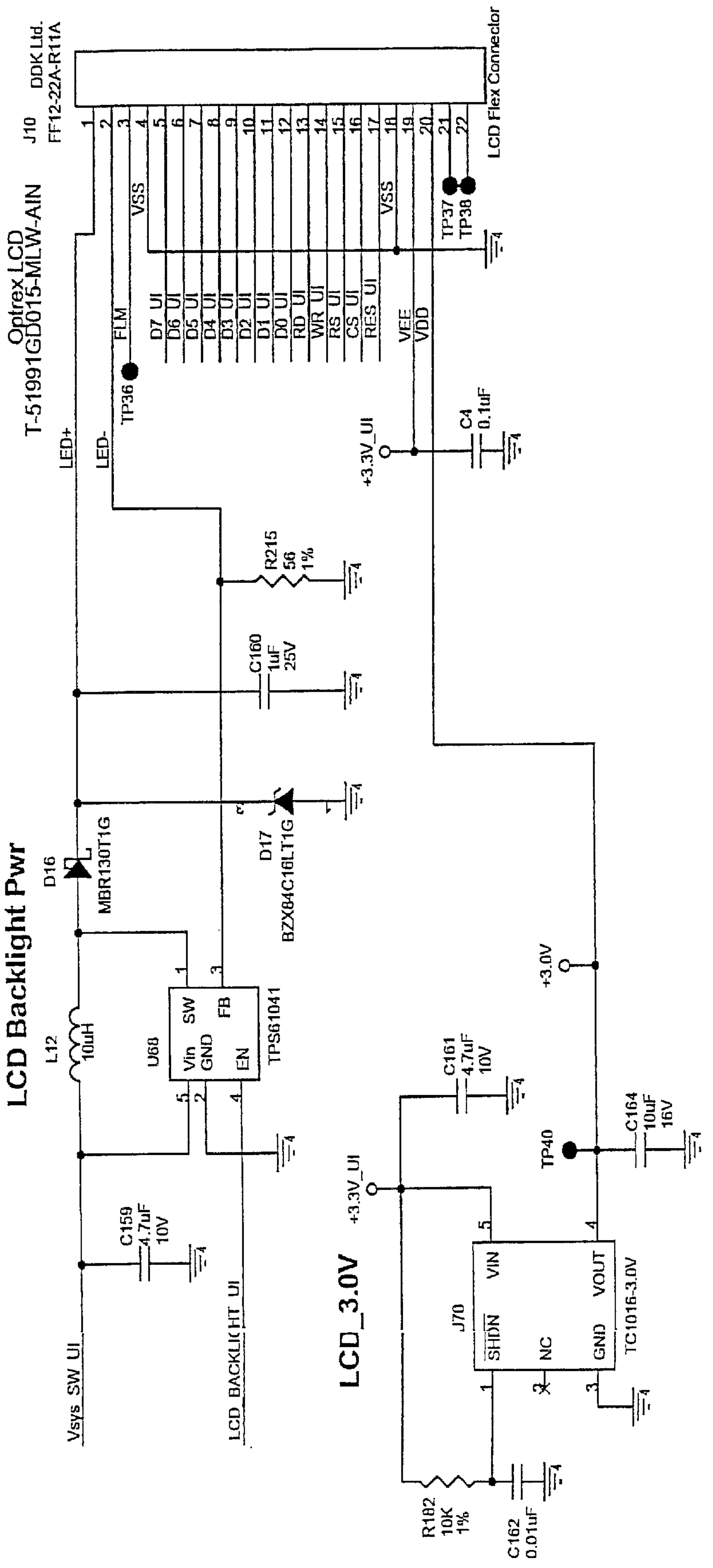
Figure 51A:
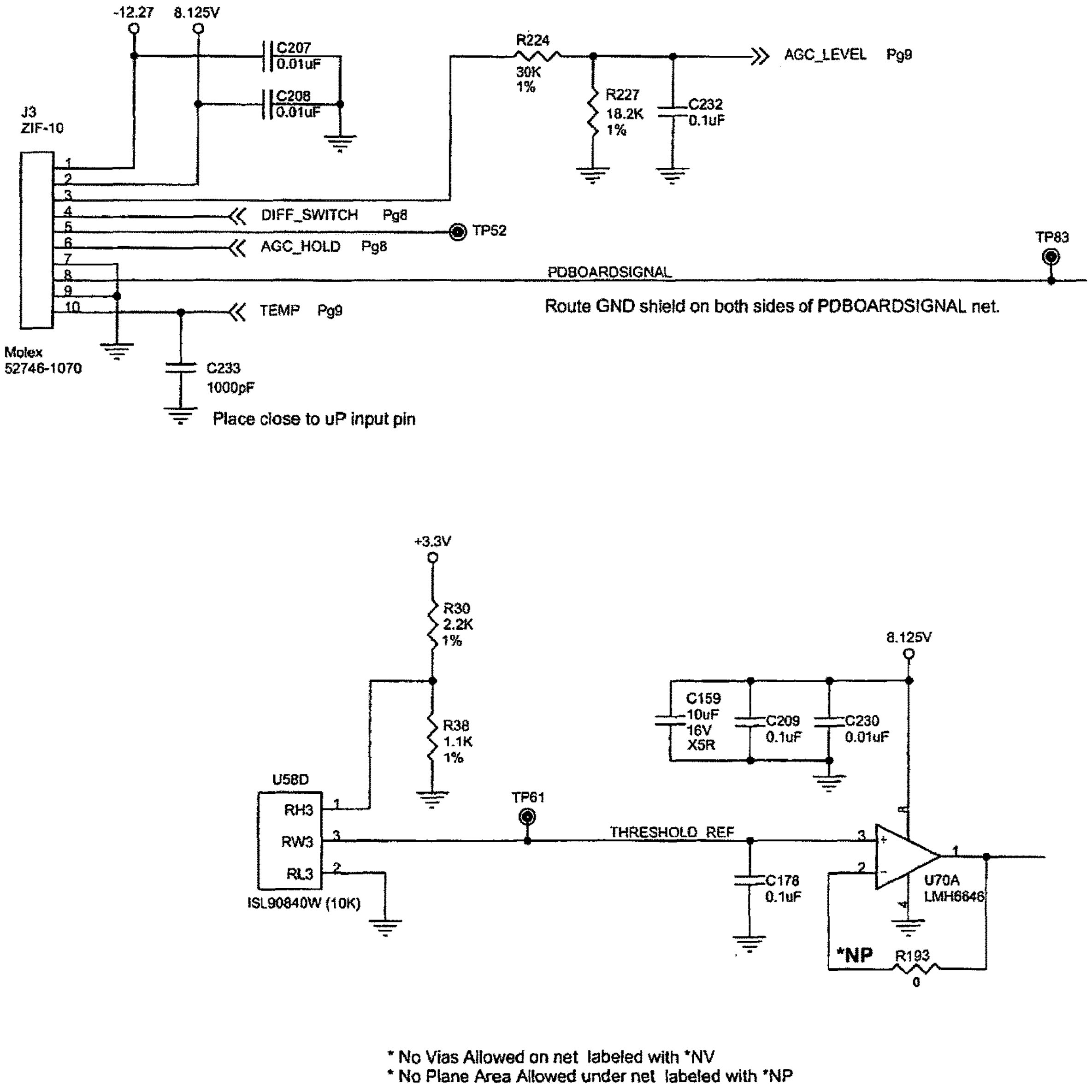
FIGS. 51A-B is a schematic of a circuit diagram of the photodiode board connection.
Figure 51B:
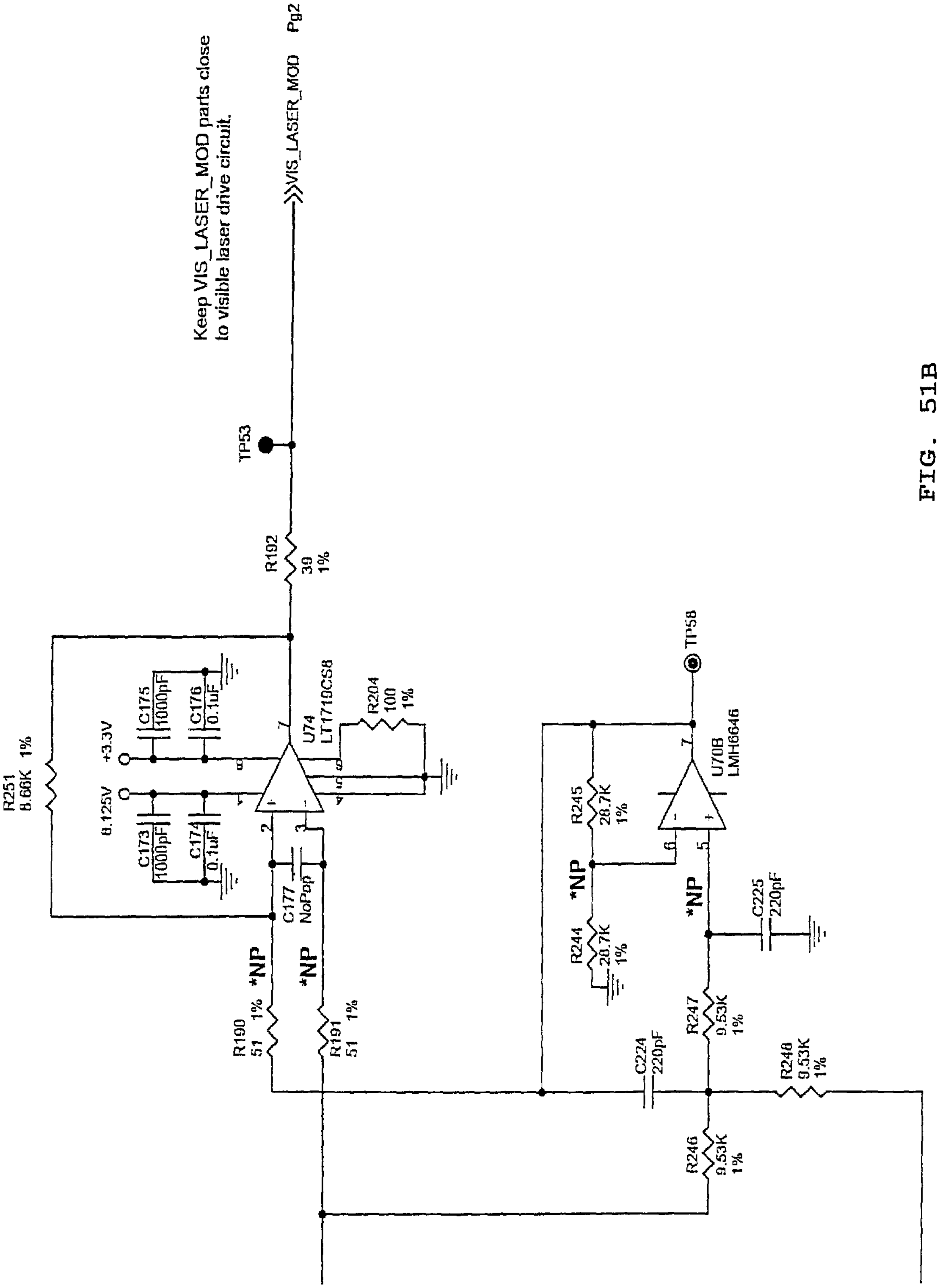
Figure 52:
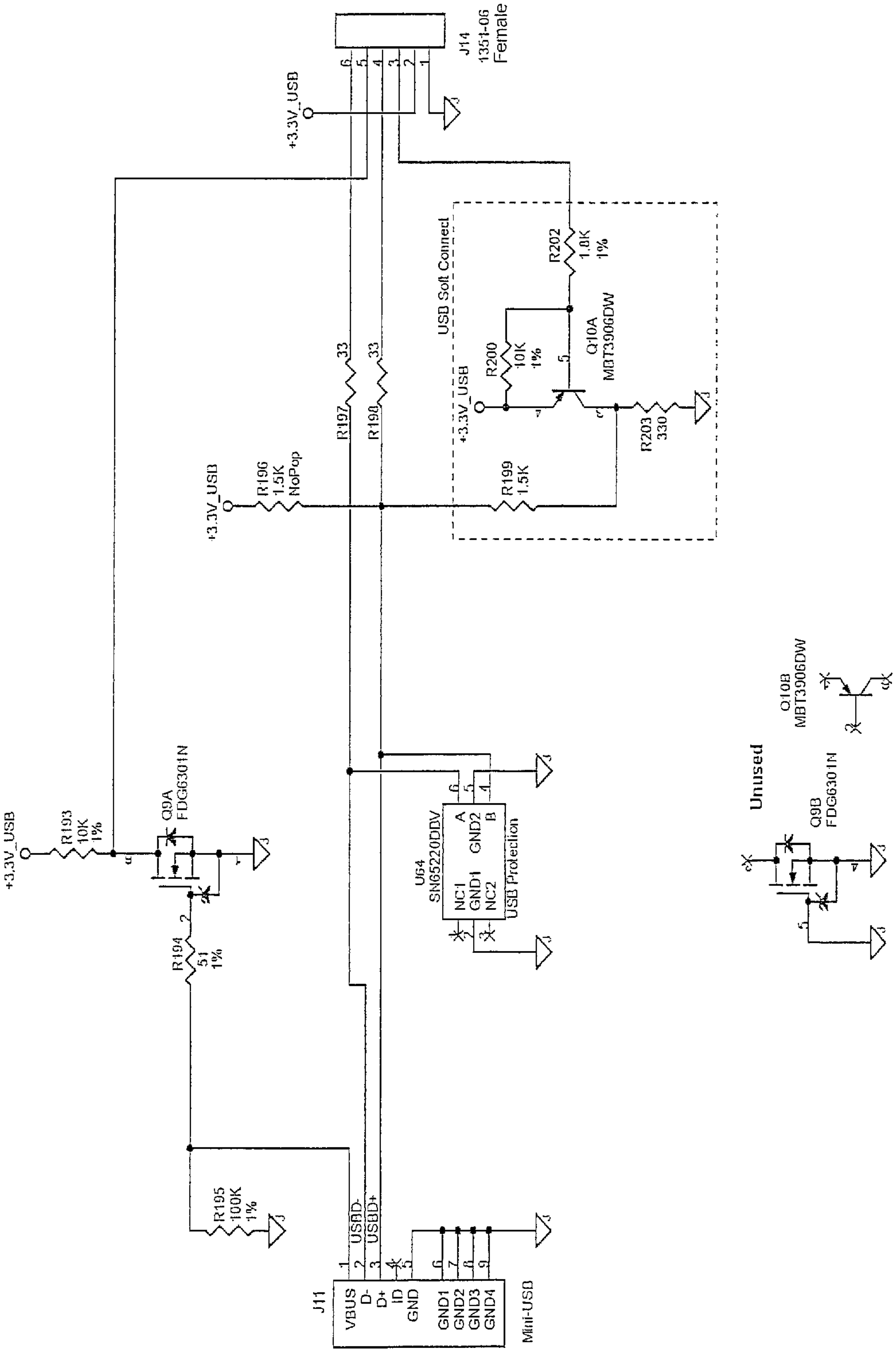
FIG. 52 is a schematic of a circuit diagram of the USB chip.
Figure 53A:
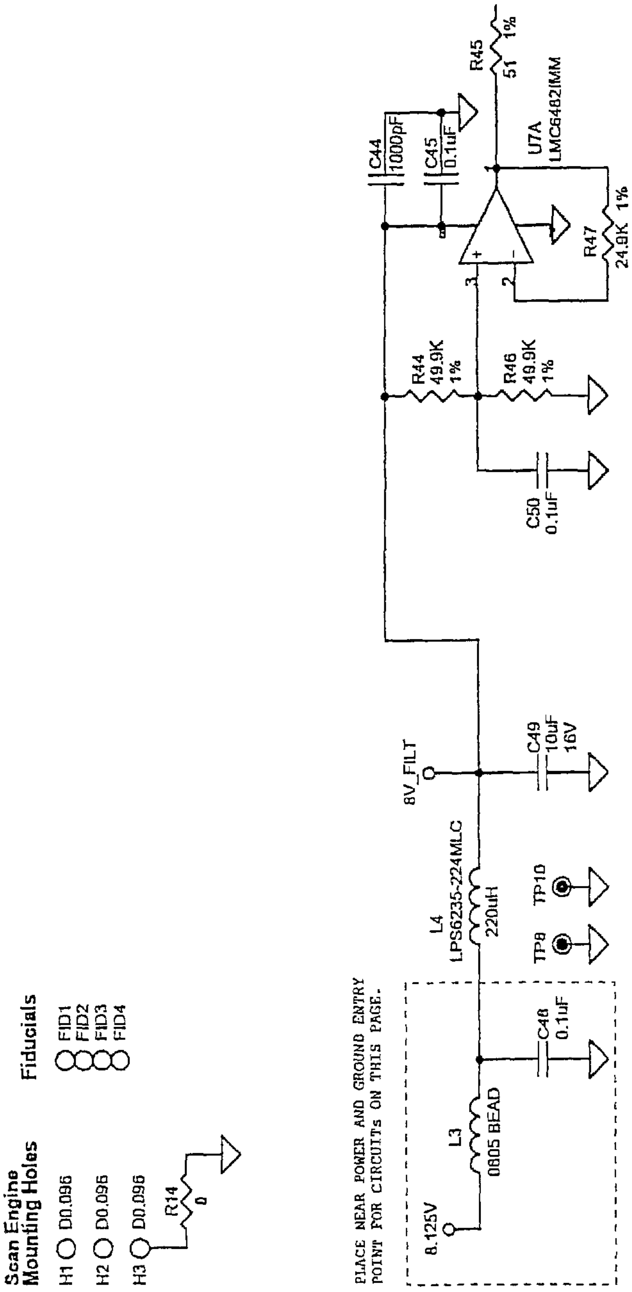
FIGS. 53A-E is a schematic of a circuit diagram of the photodiode board.
Figure 53B:
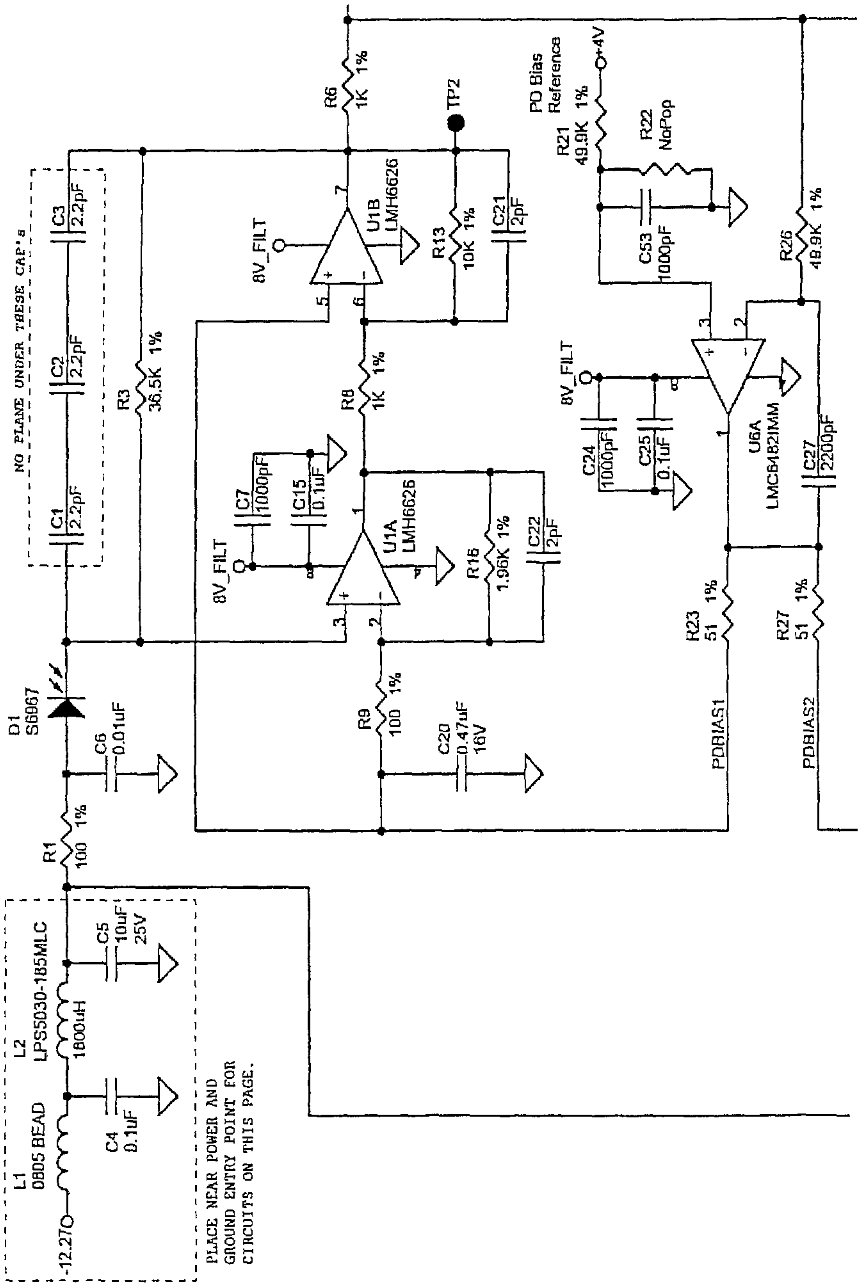
Figure 53C:
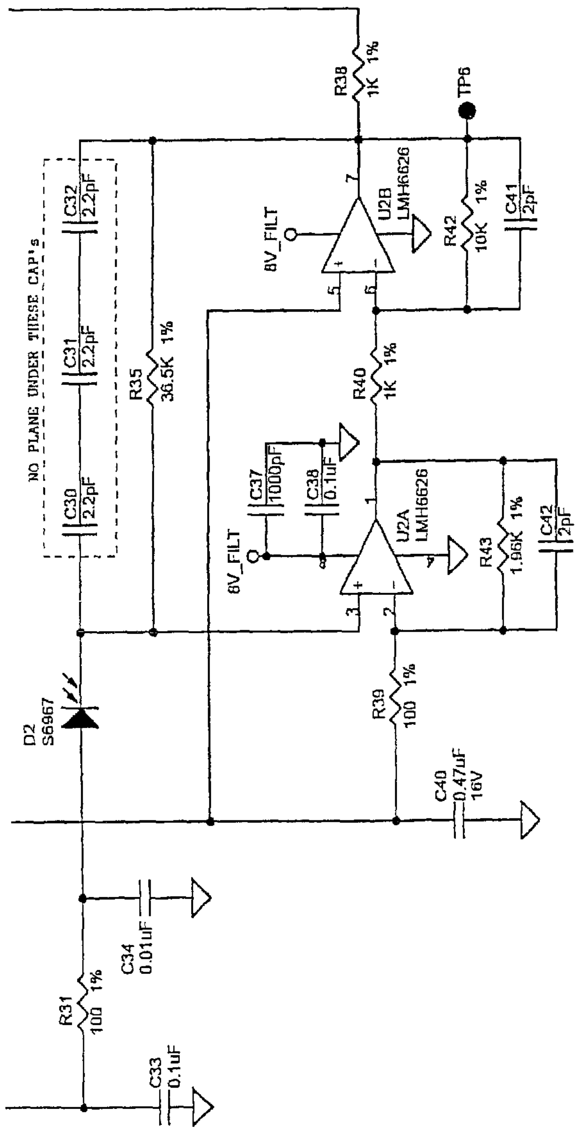
Figure 53D:
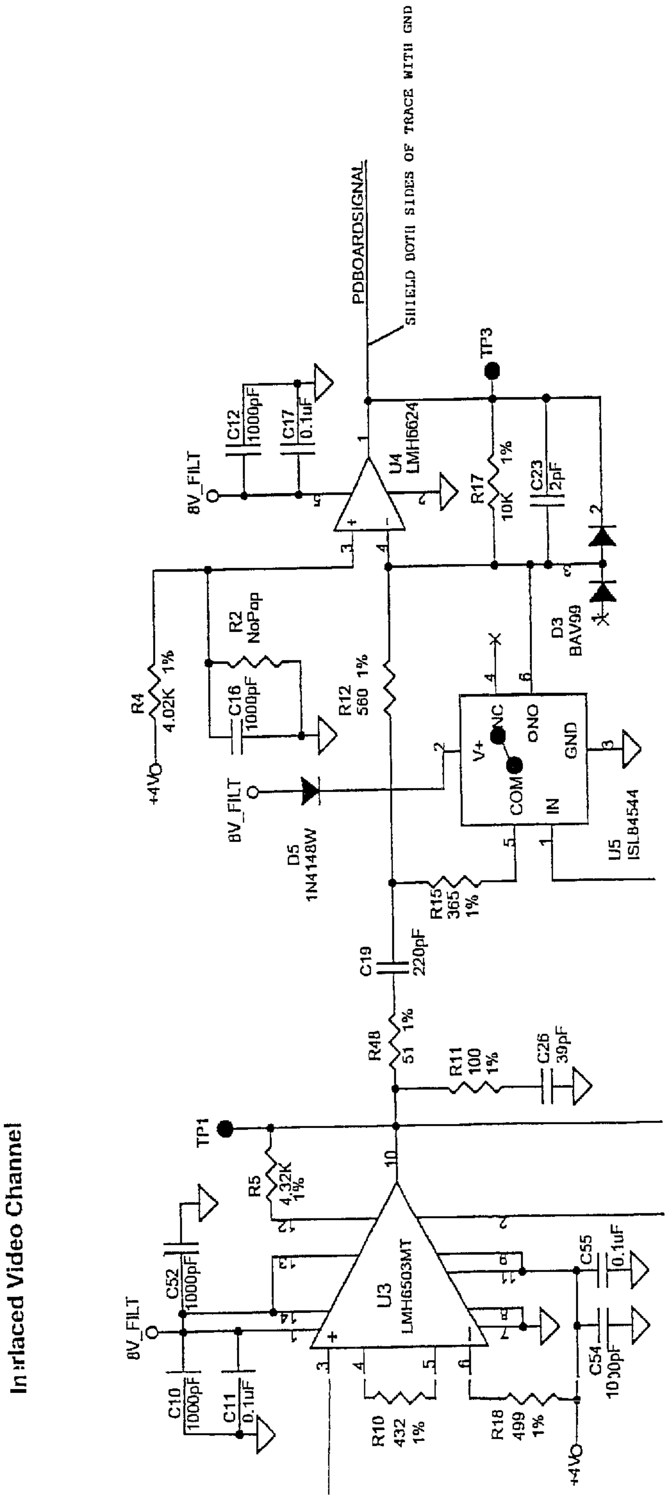
Figure 53E:
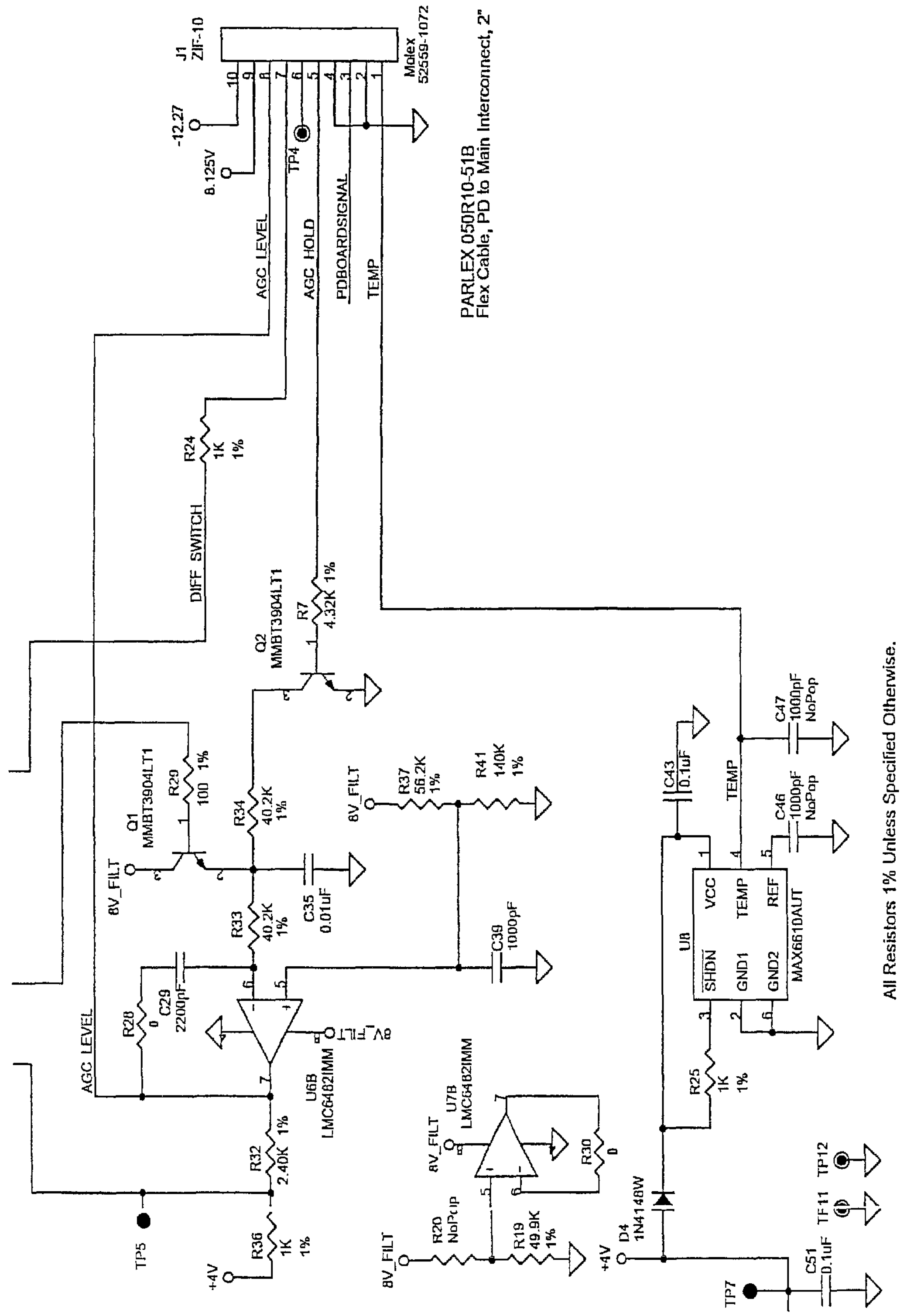
Figure 54:
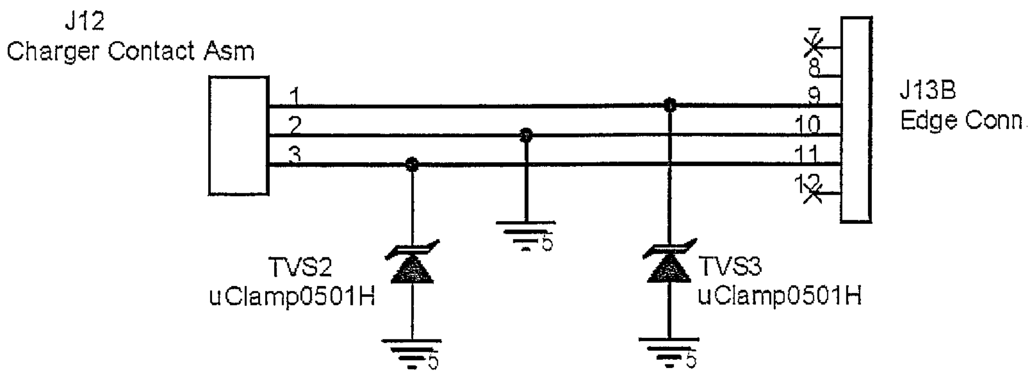
FIG. 54 is a schematic of a circuit diagram of the battery connector board.
Figure 54:
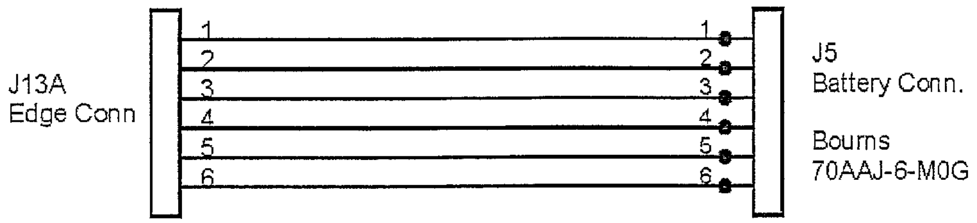
Figure 55A:
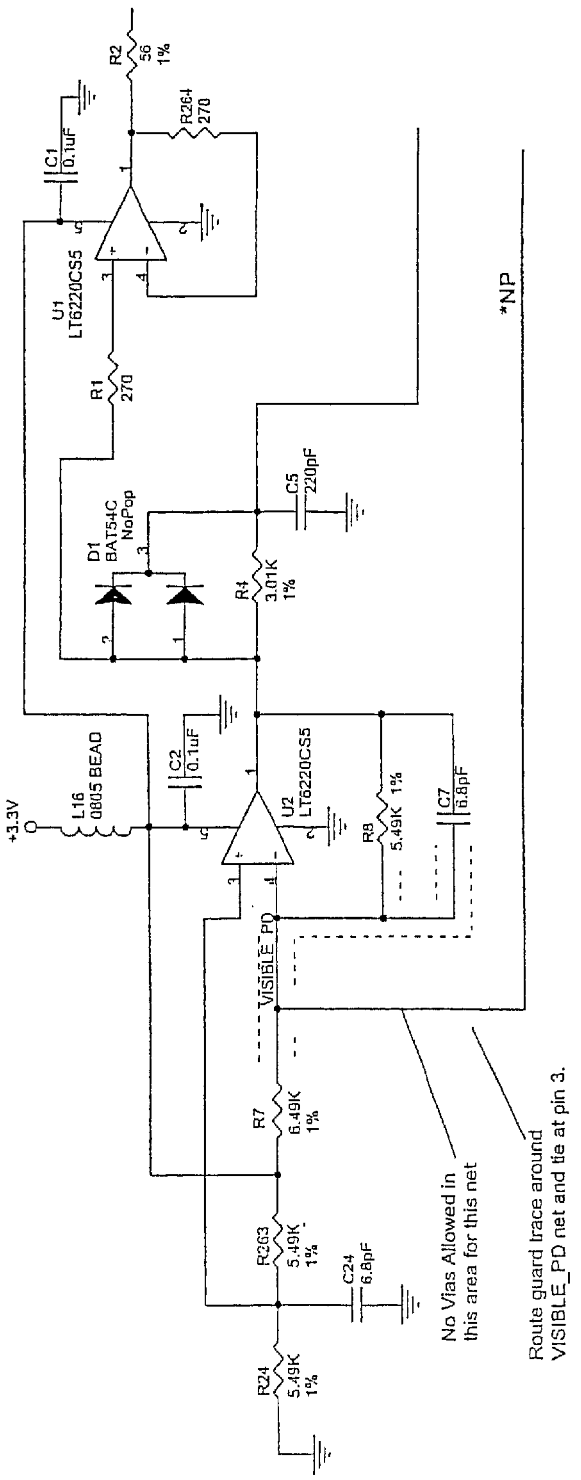
FIGS. 55A-E is a schematic of a circuit diagram of the visible laser drive.
Figure 55B:
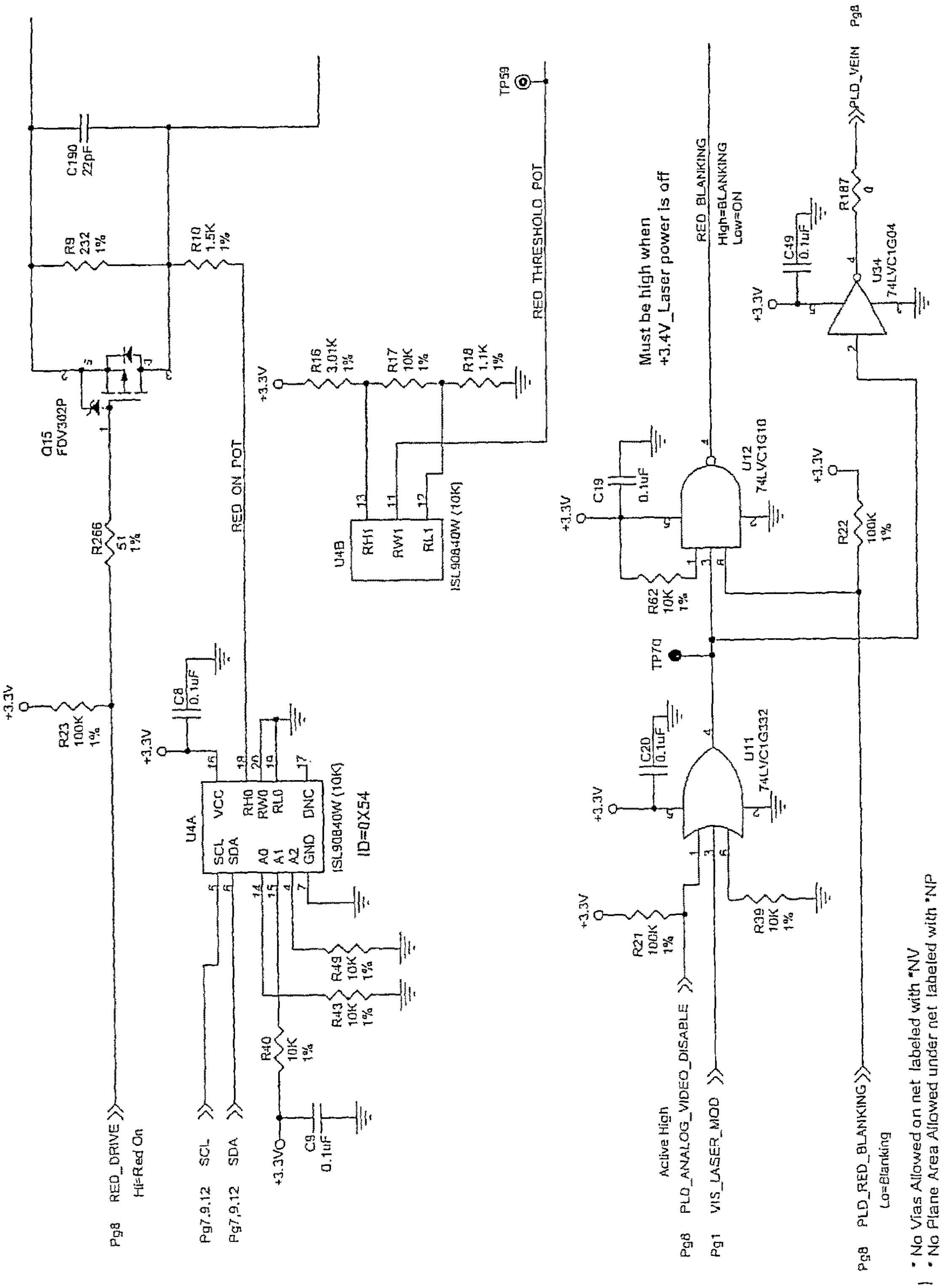
Figure 55C:
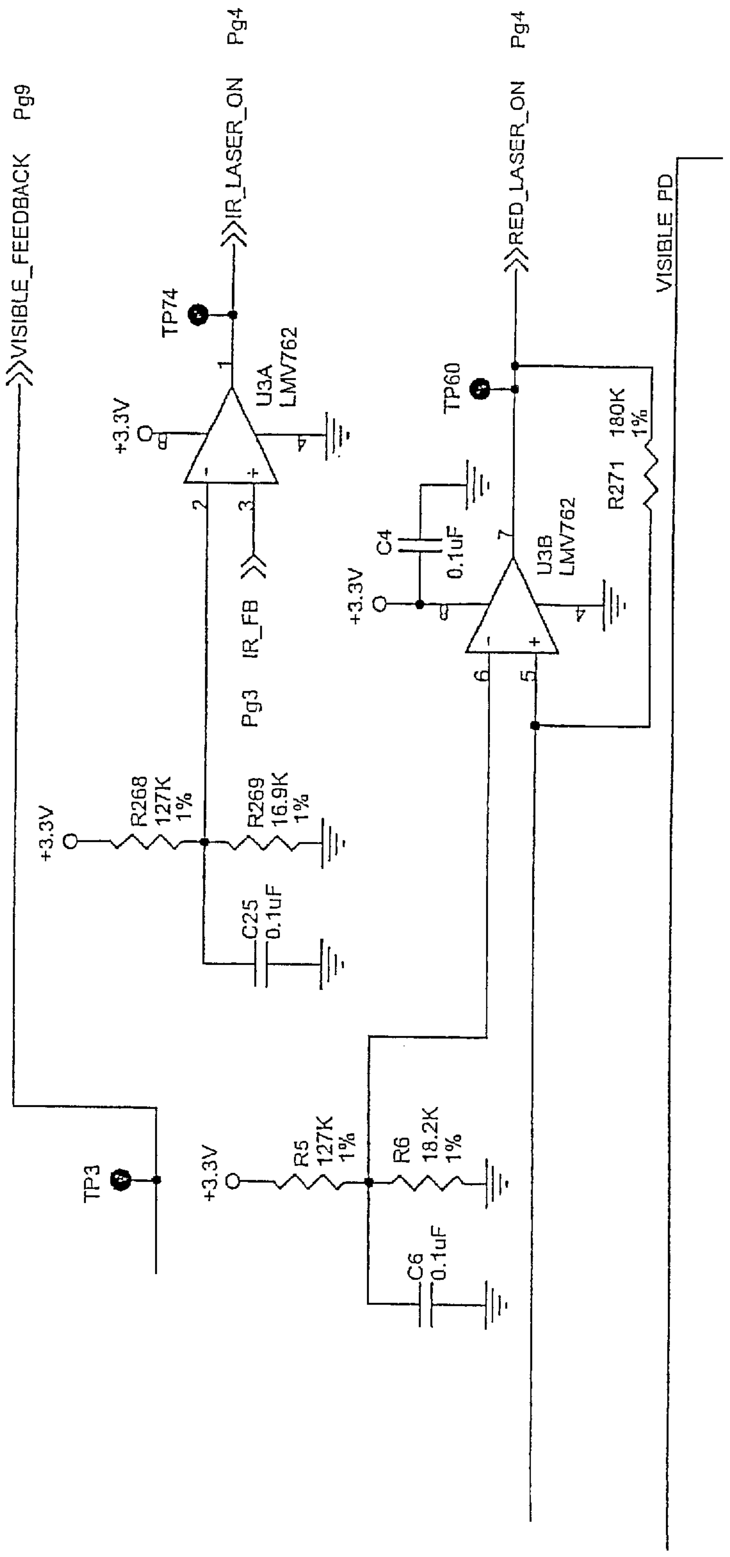
Figure 55D:
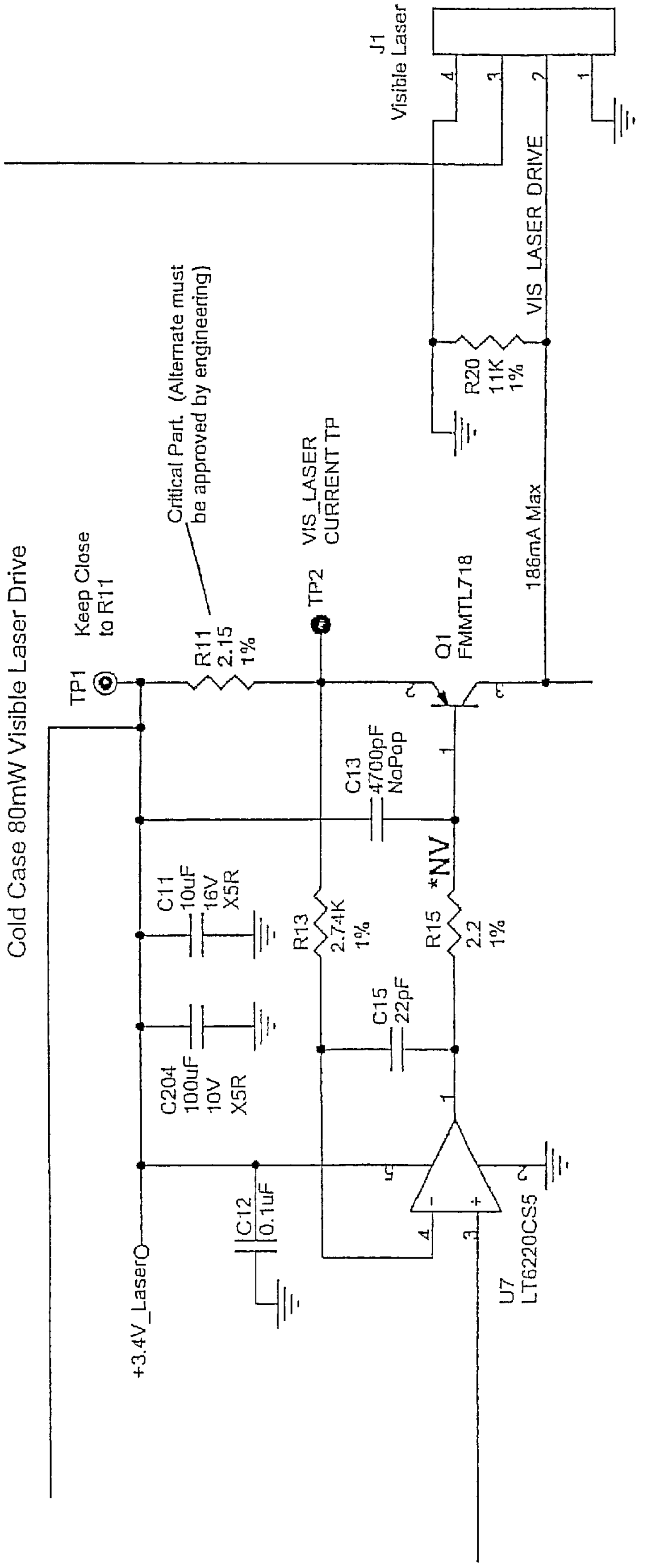
Figure 55E:
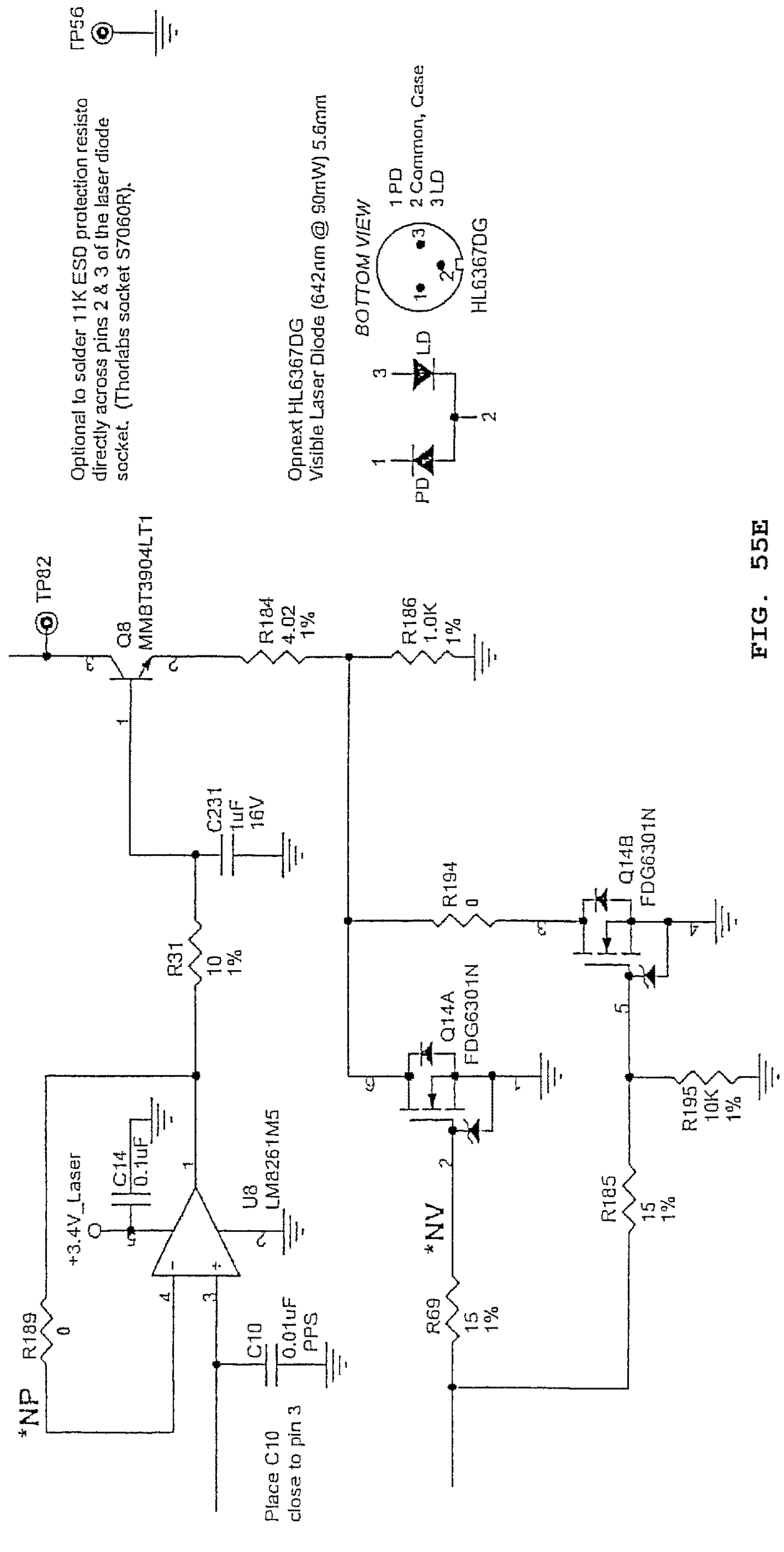
Figure 56A:
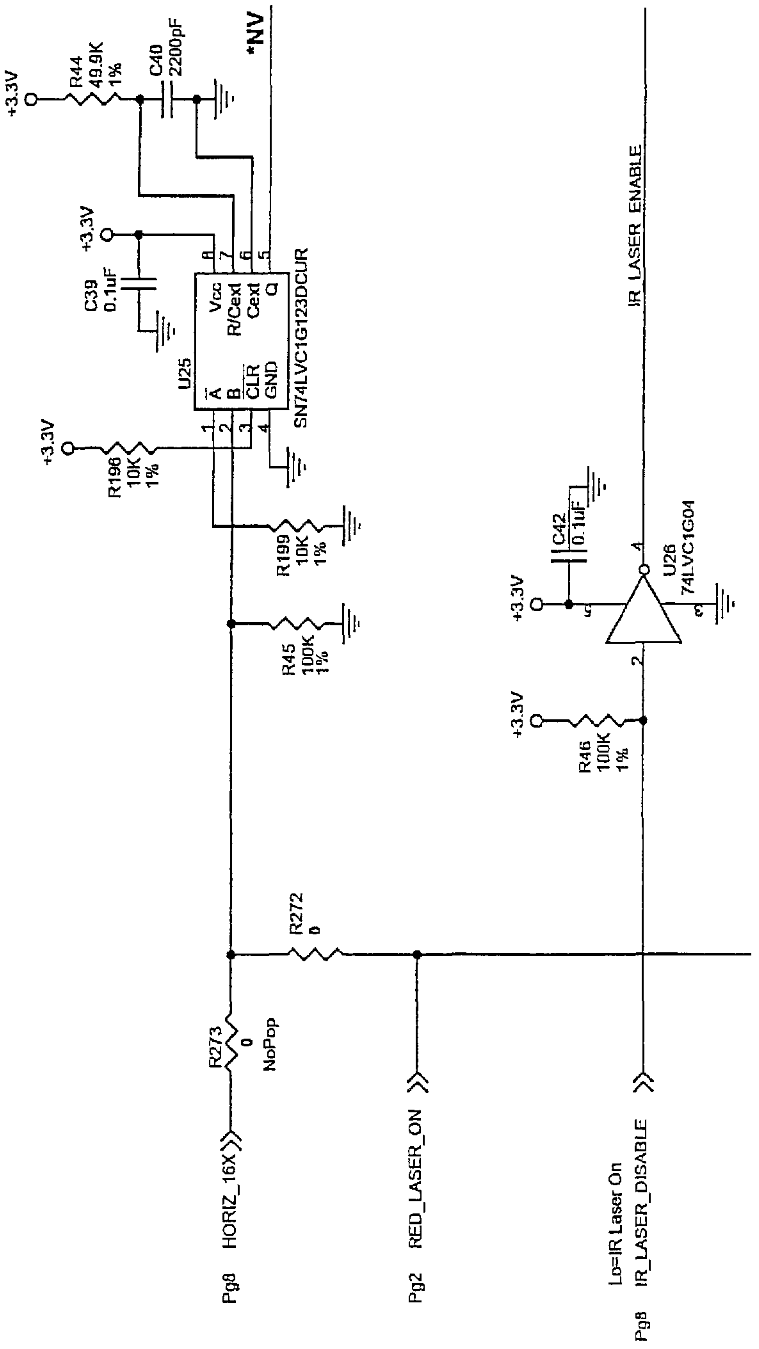
FIGS. 56A-D is a schematic of a circuit diagram of the laser safety feature of the present invention
Figure 56B:
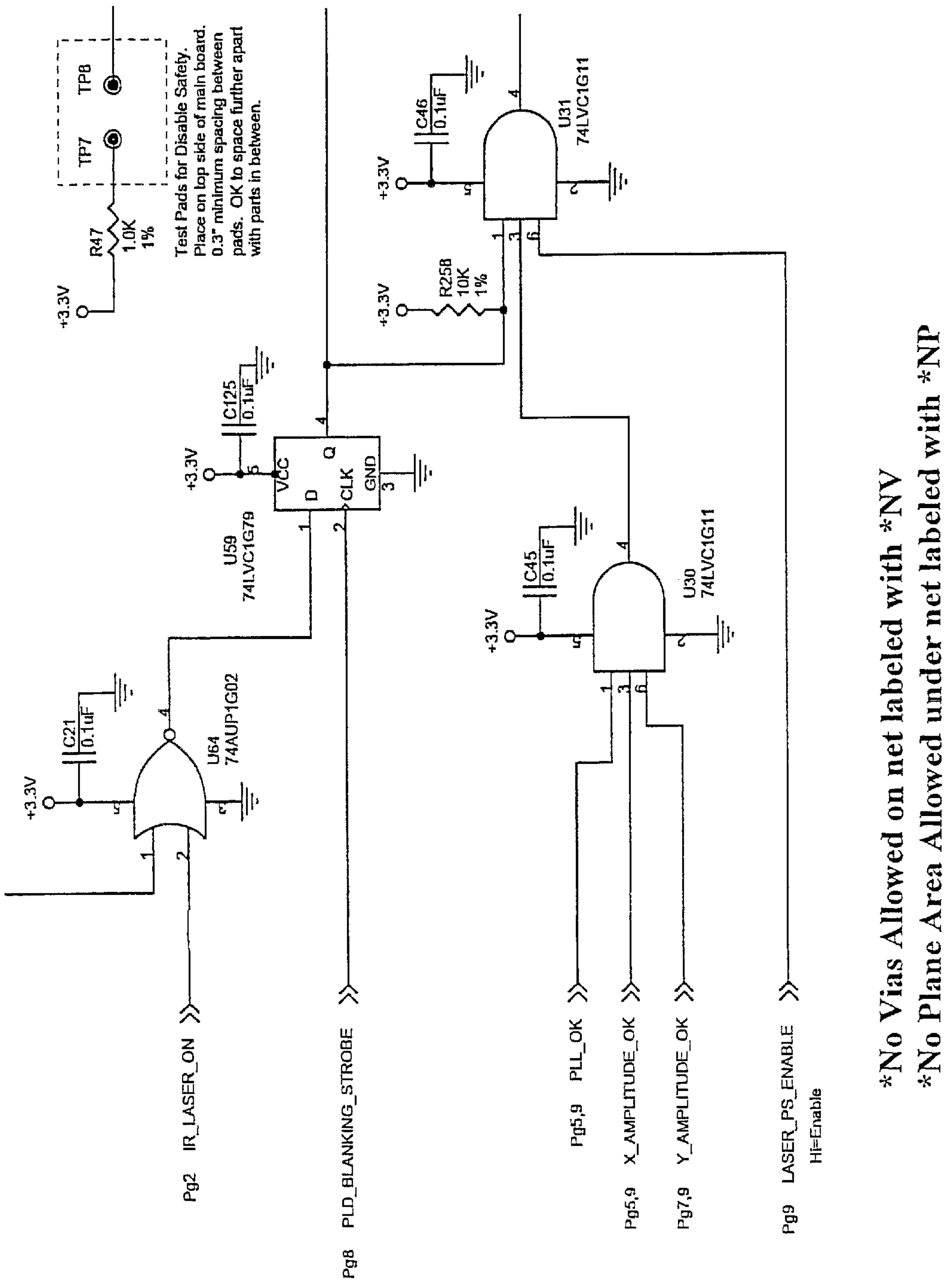
Figure 56C:
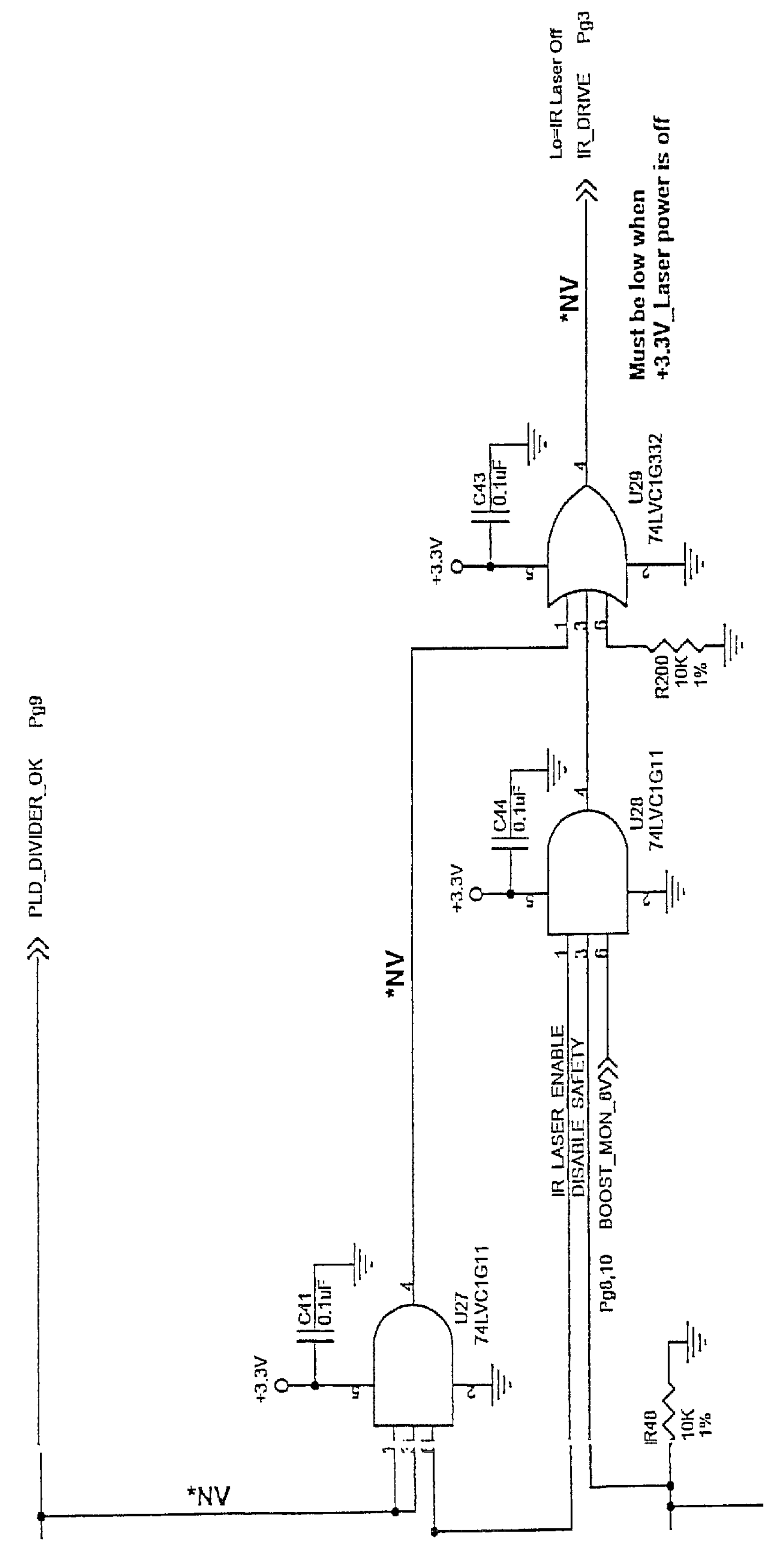
Figure 56D:
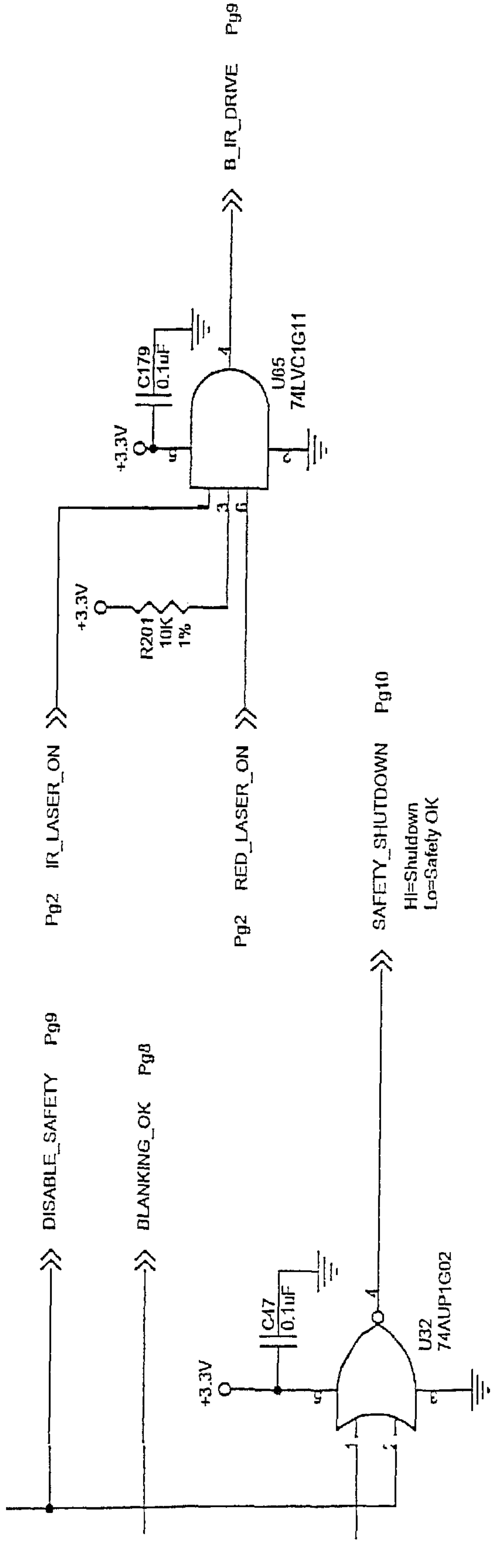
Figure 57A:
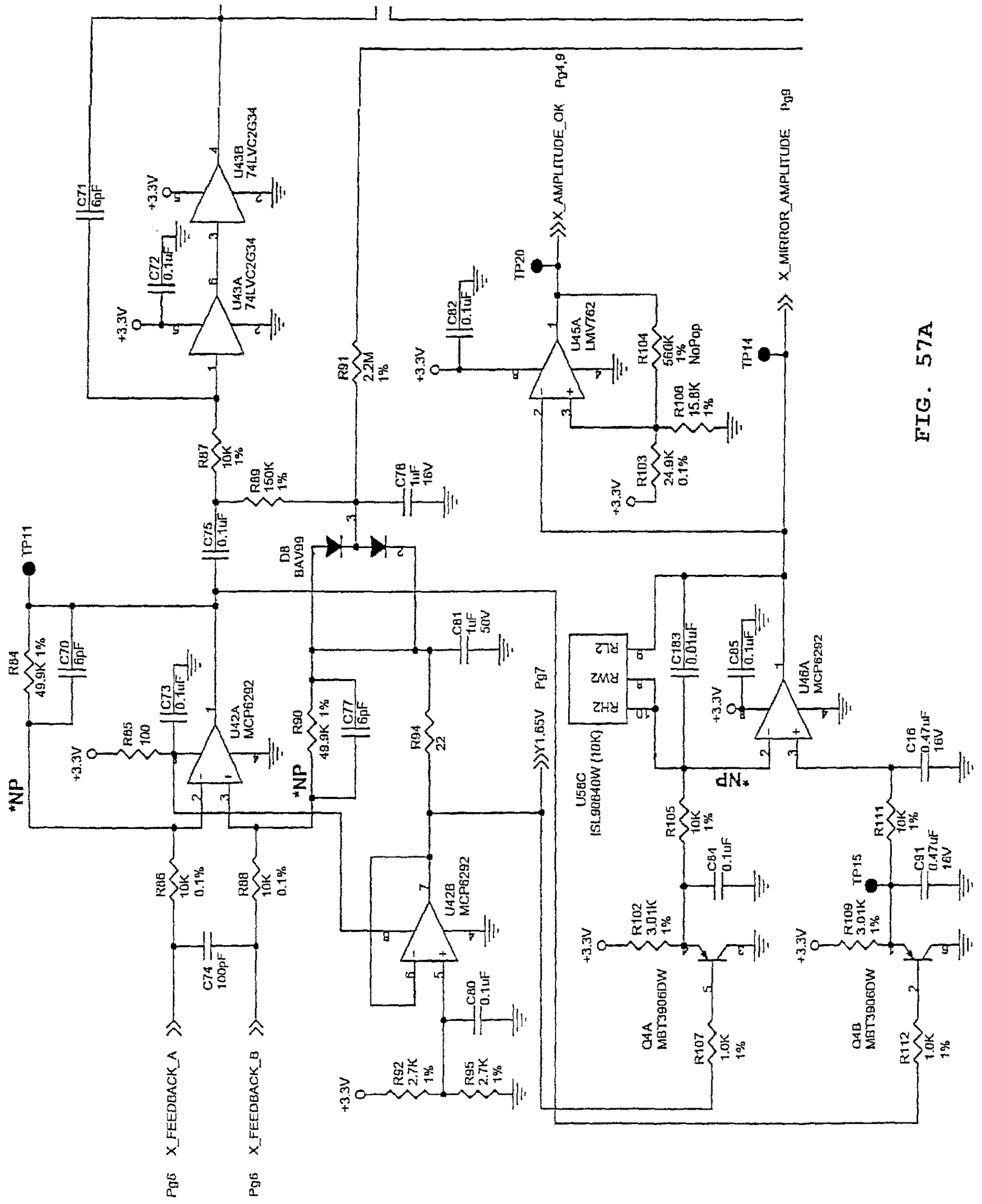
FIGS. 57A-D is an additional schematic of a circuit diagram of the photodiode engine.
Figure 57B:
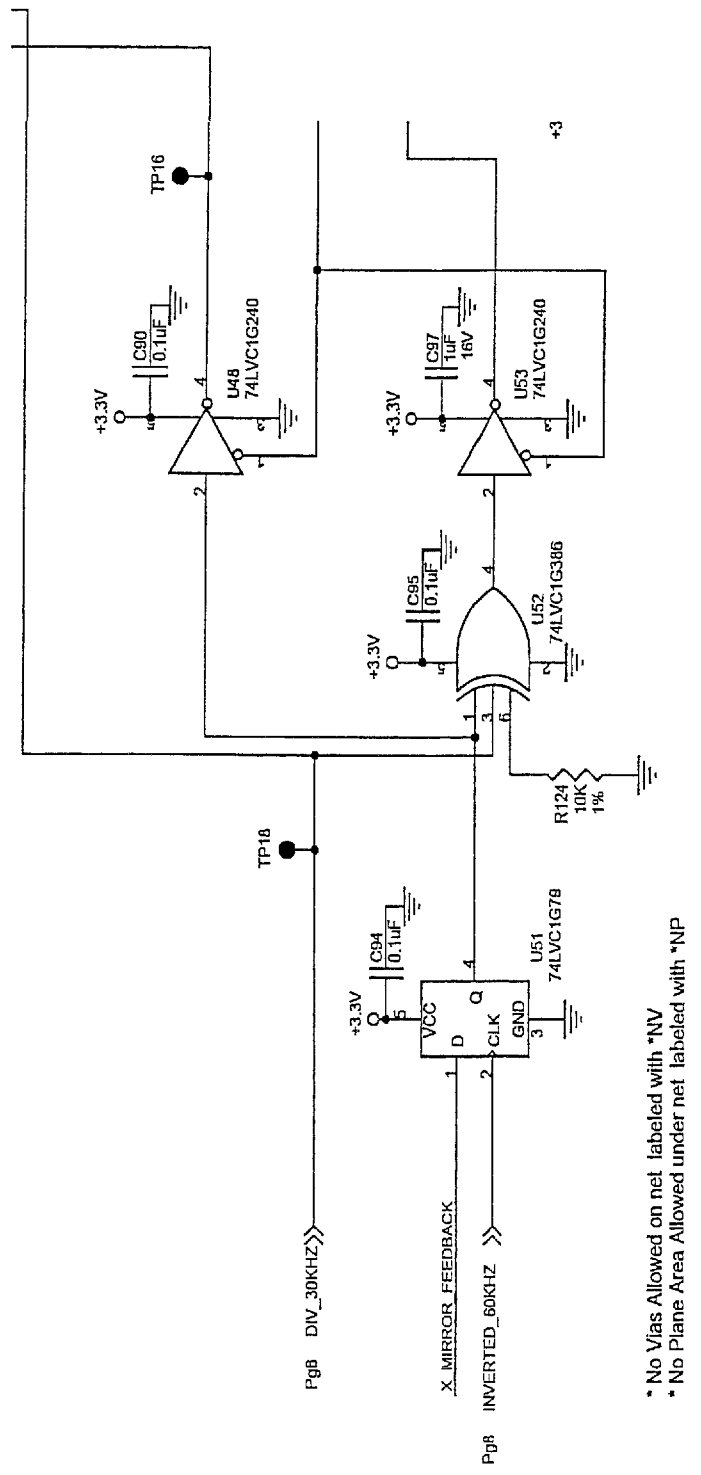
Figure 57C:
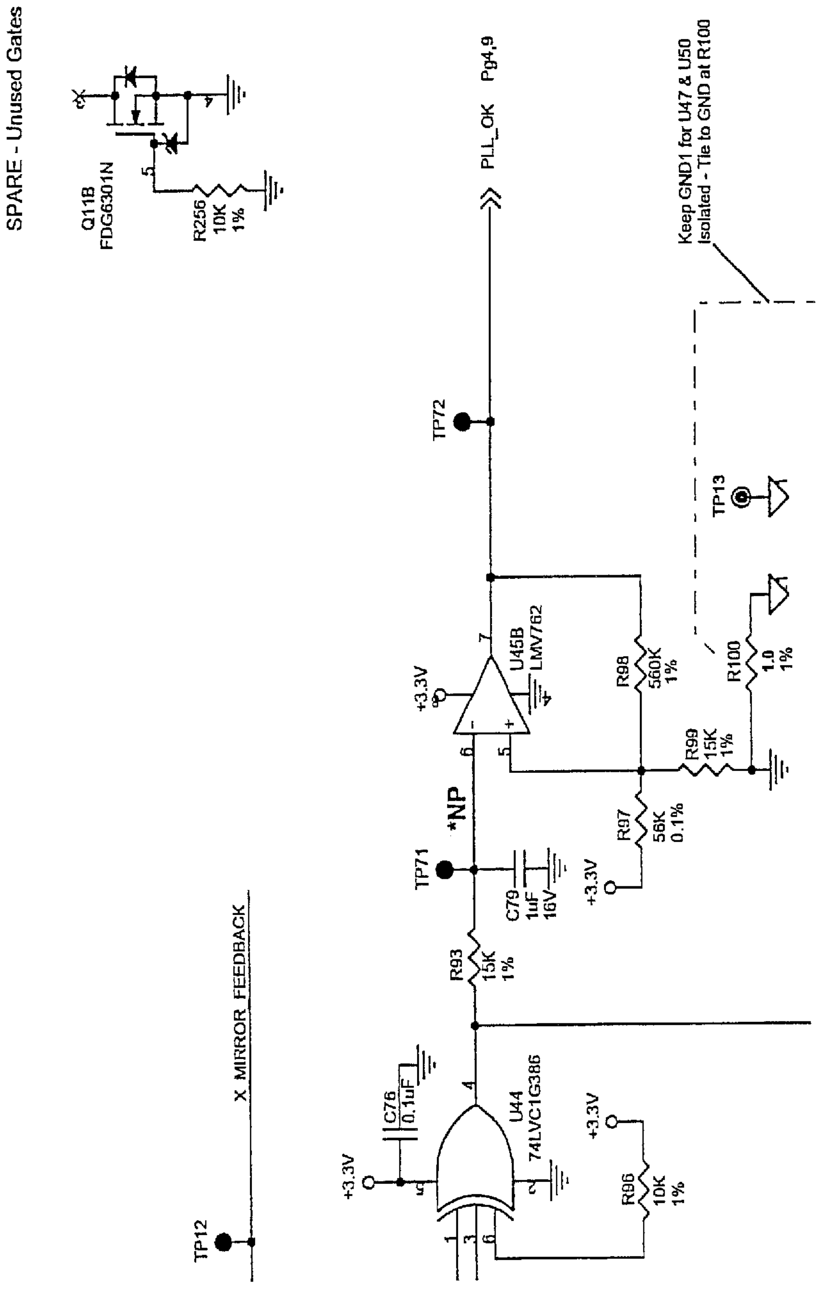
Figure 57D:
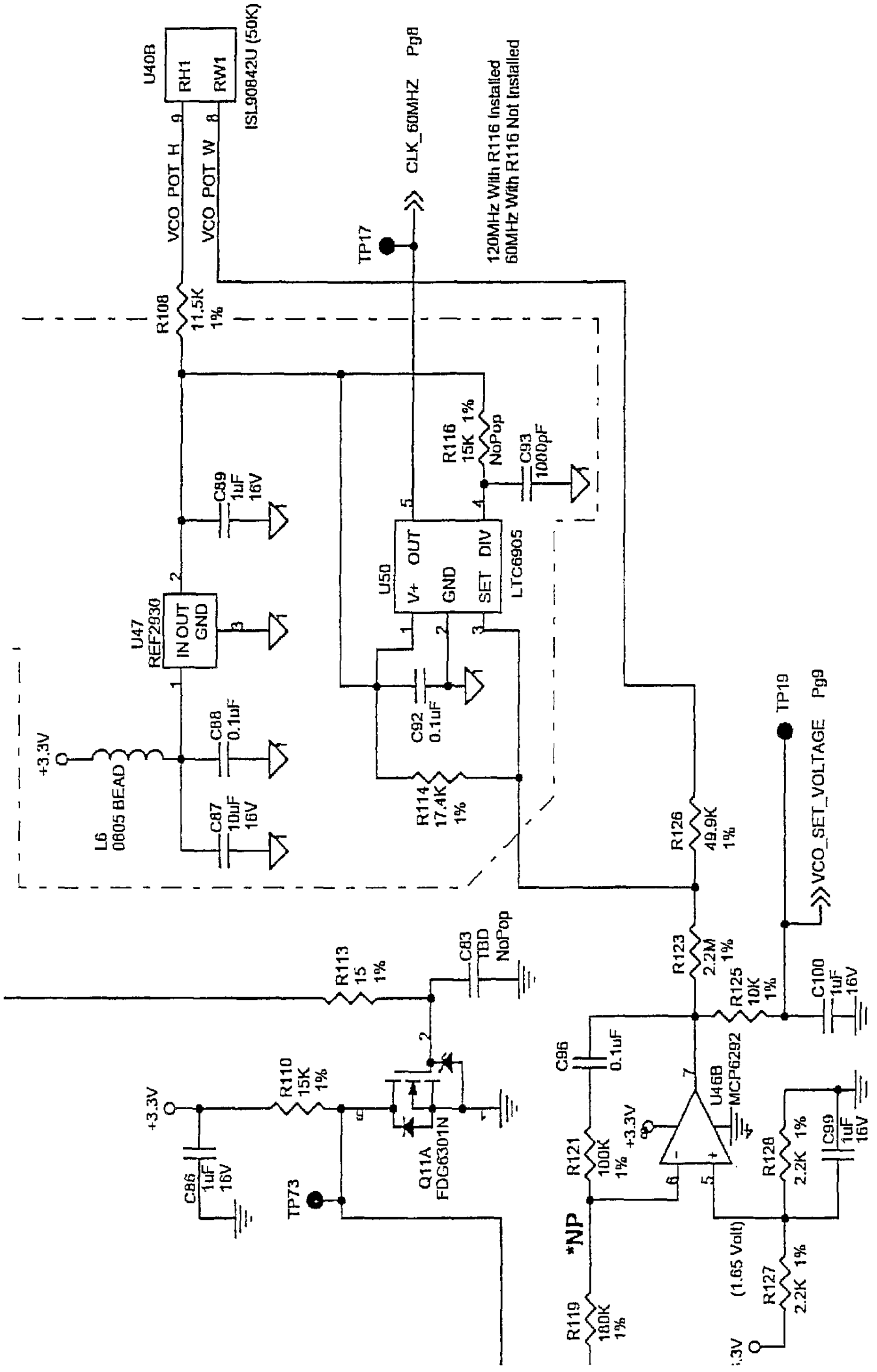
Figure 58A:
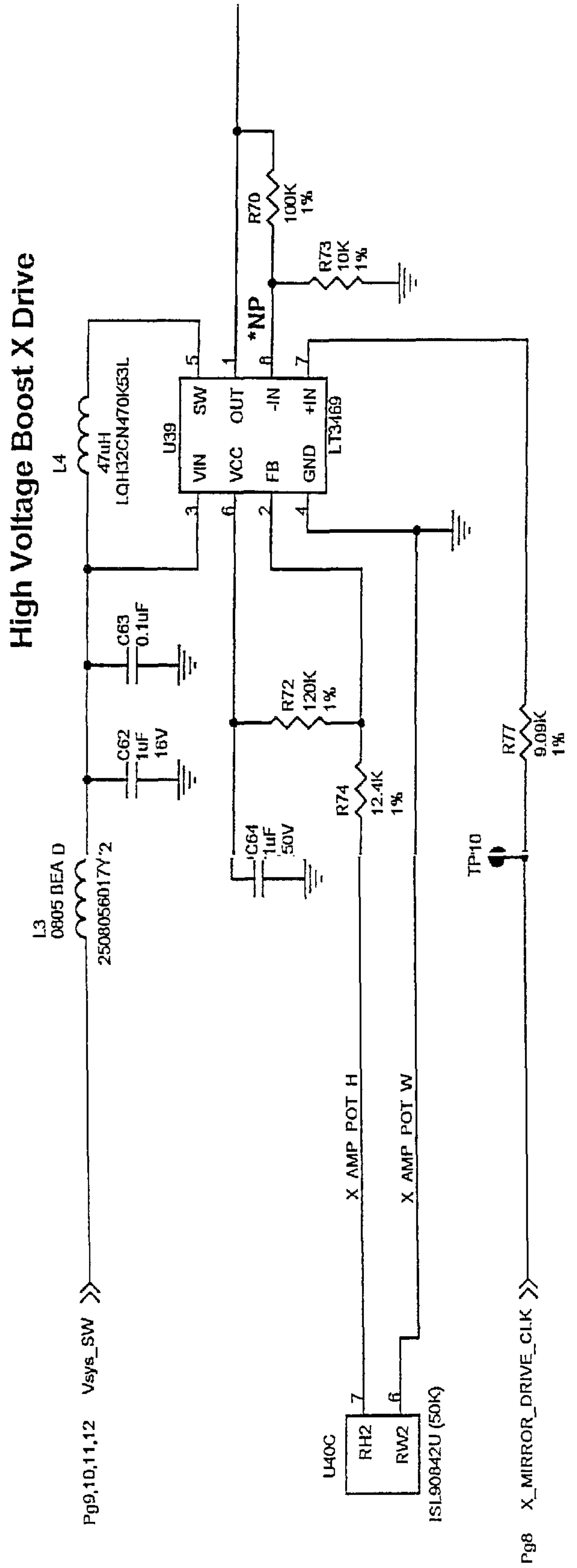
FIGS. 58A-E is a schematic of a circuit diagram of the speaker of the present invention.
Figure 58B:
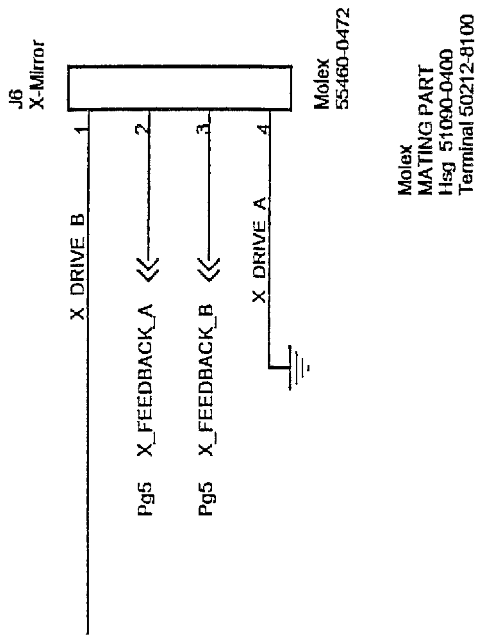
Figure 58C:
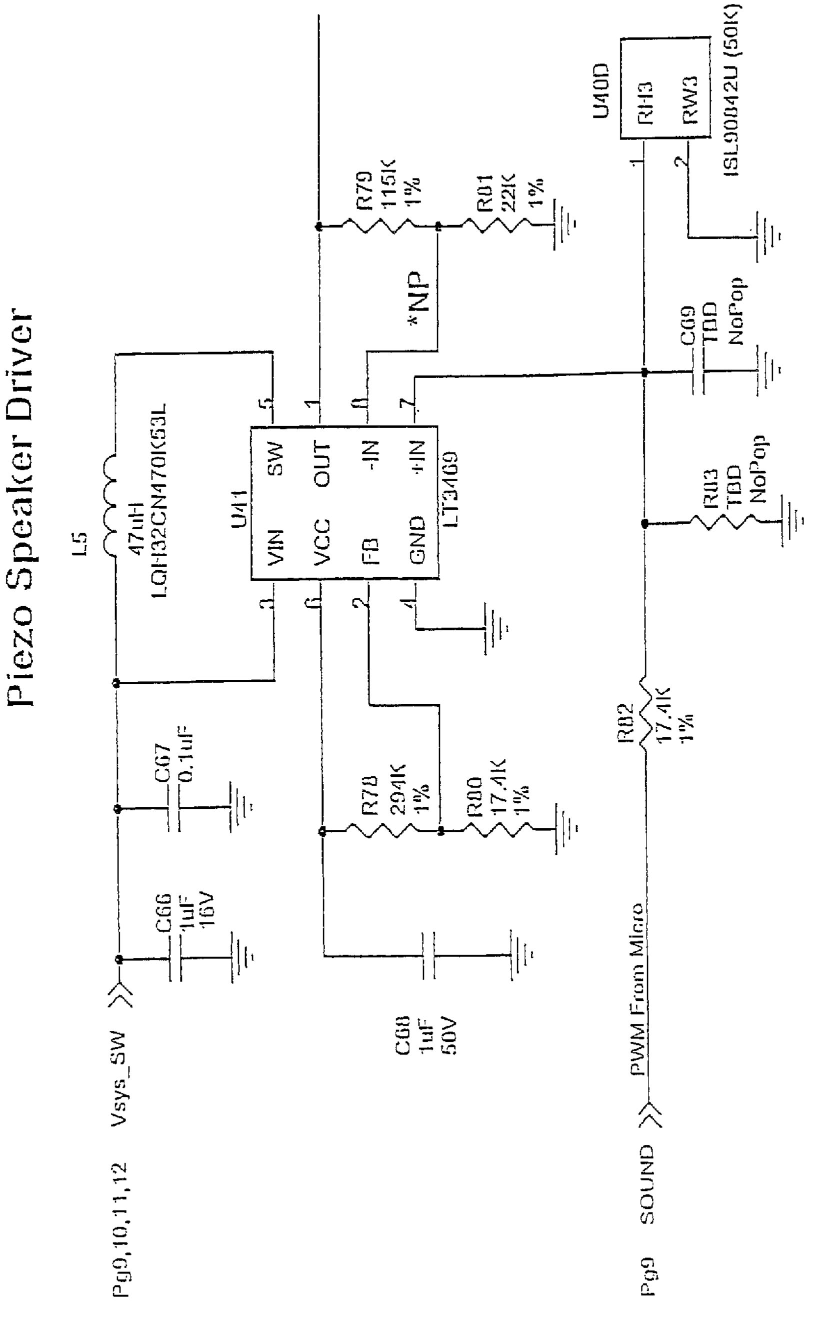
Figure 58D:
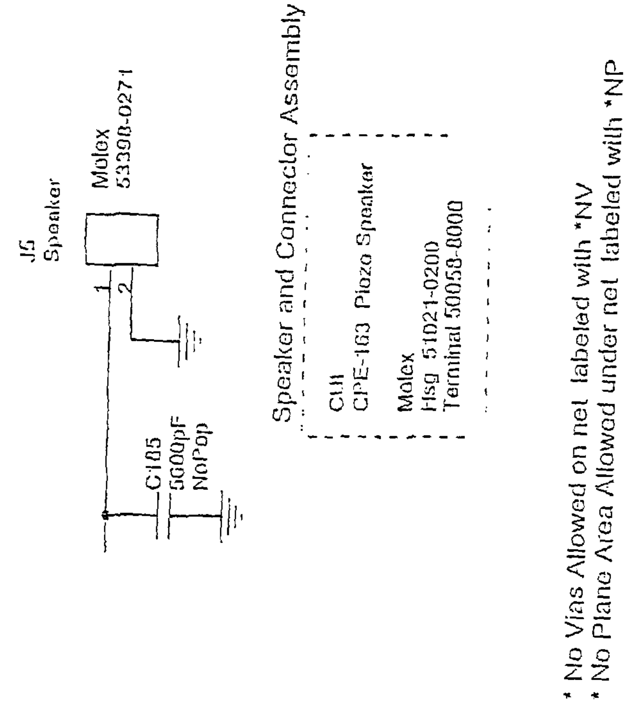
Figure 58E:
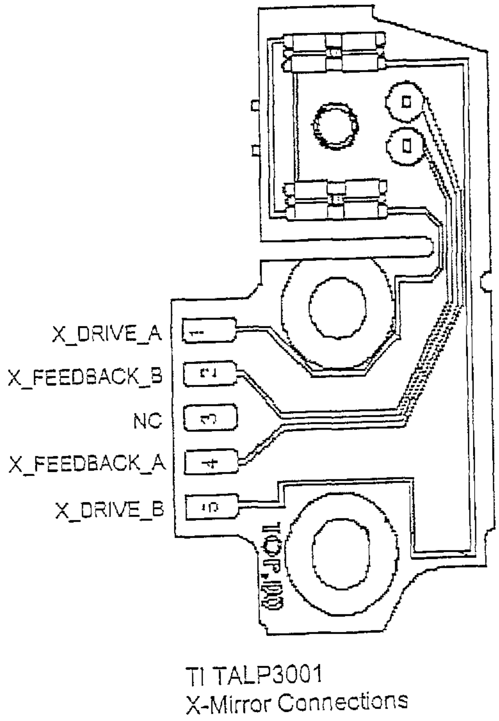
Figure 59A:
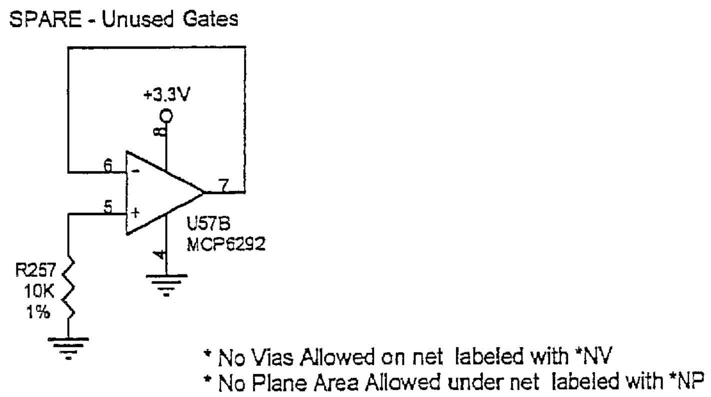
FIGS. 59A-G is an additional schematic of a circuit diagram of the photodiode engine.
Figure 59B:
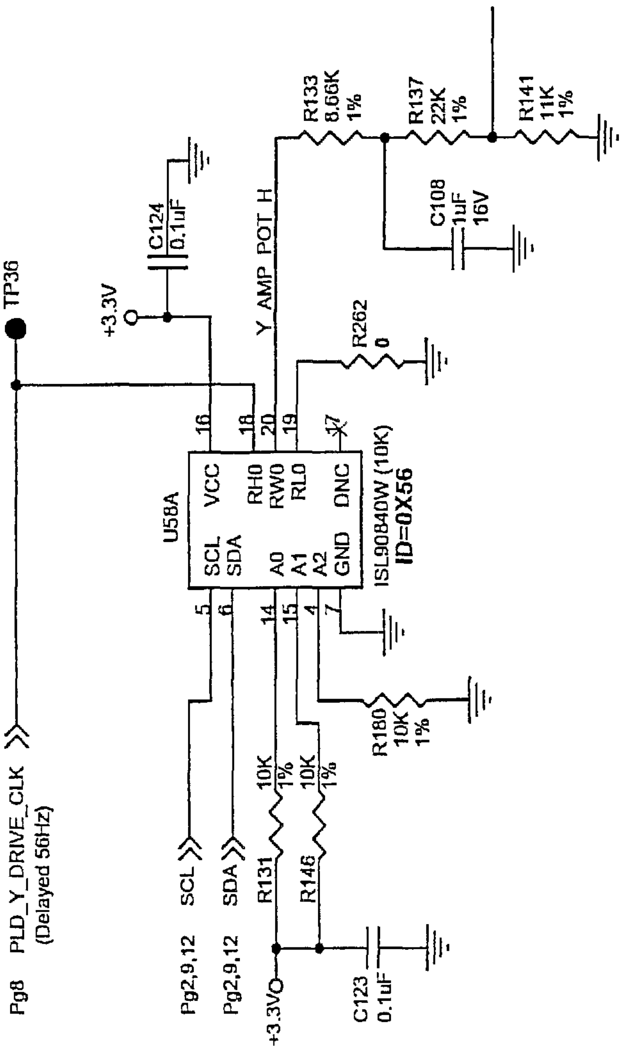
Figure 59C:
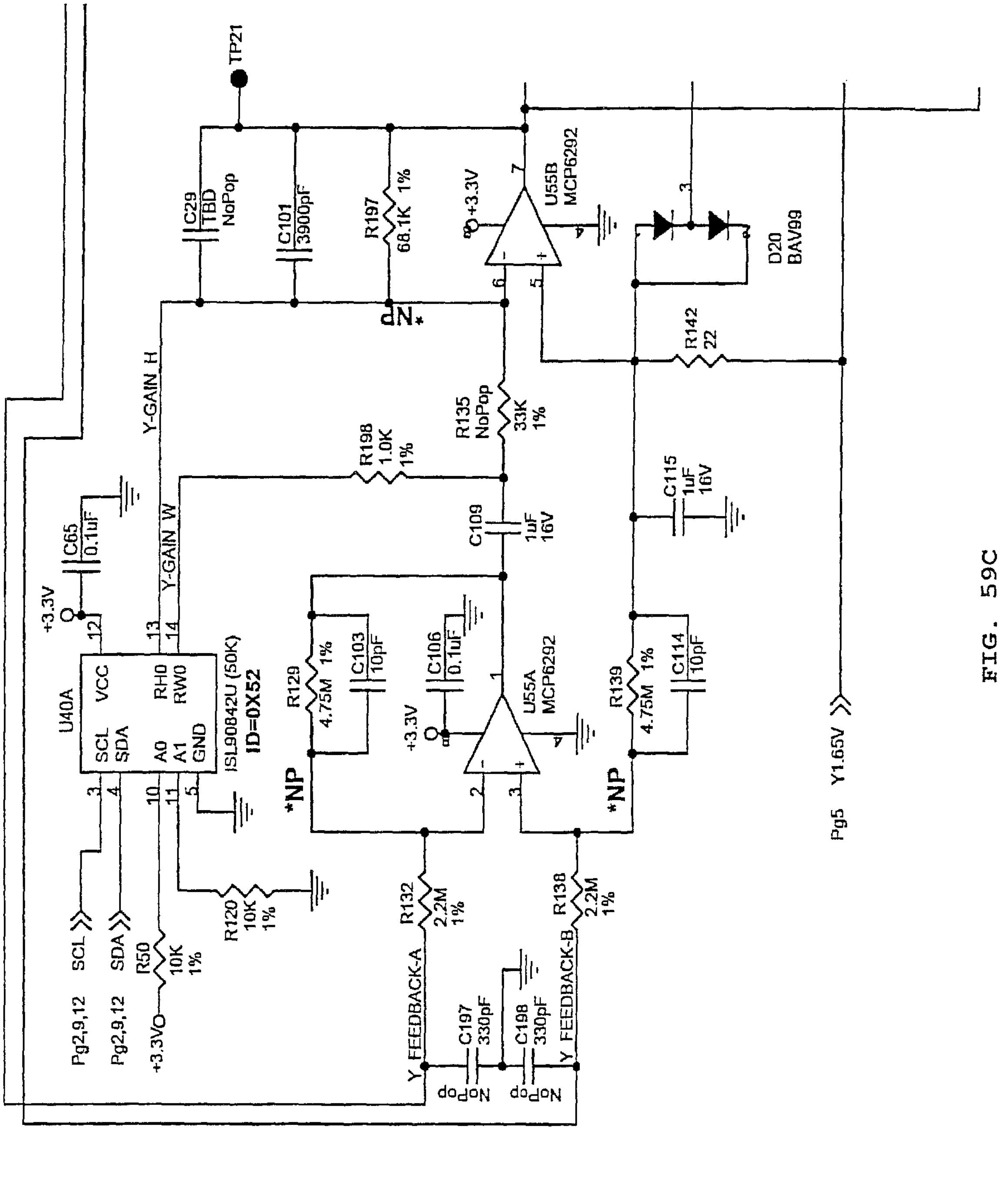
Figure 59D:
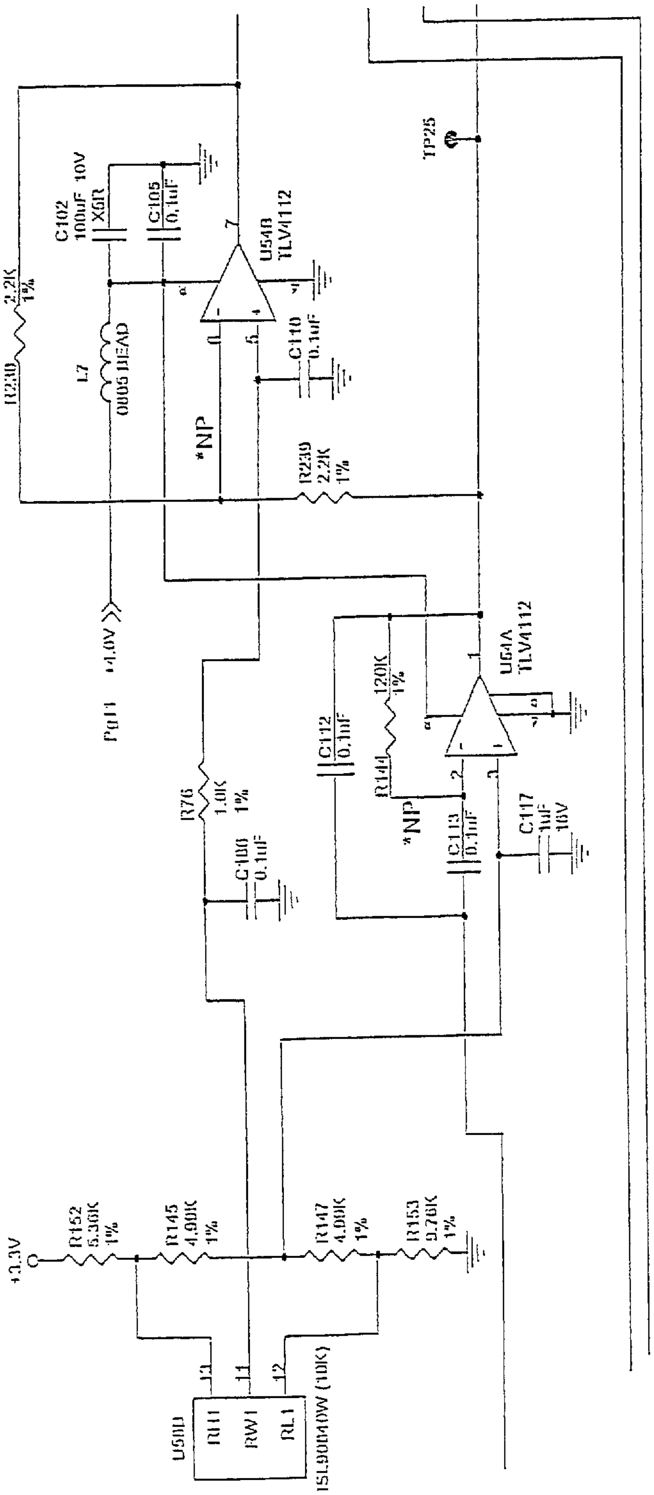
Figure 59E:
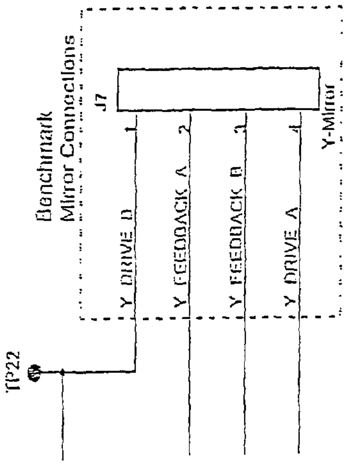
Figure 59F:
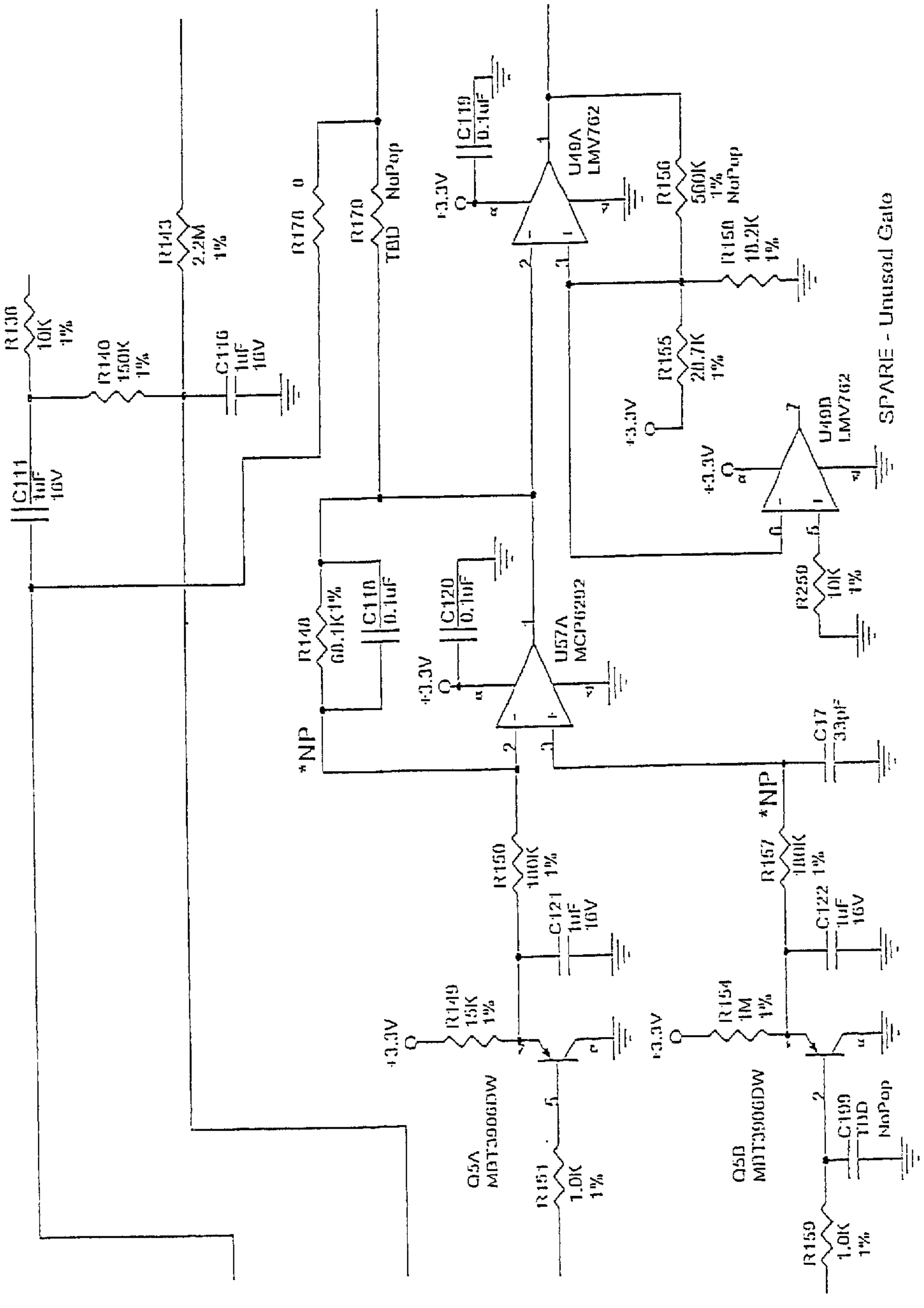
Figure 59G:
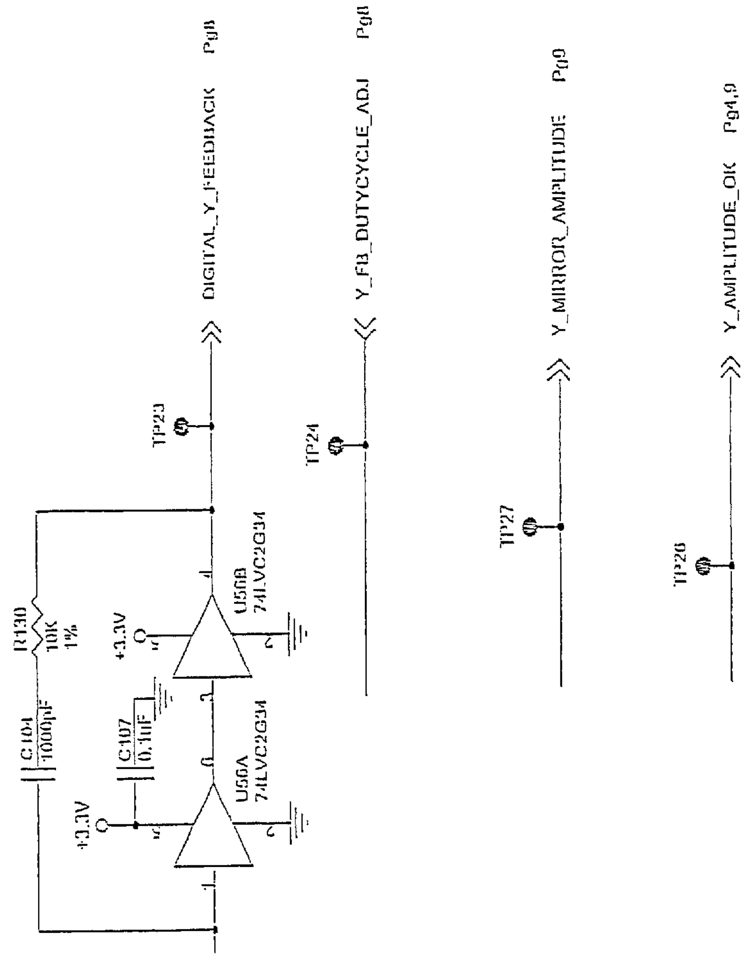
Figure 60A:
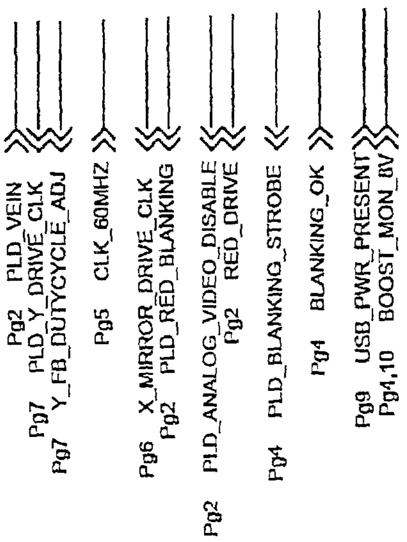
FIGS. 60A-F is an additional schematic of a circuit diagram of the photodiode assembly.
Figure 60B:
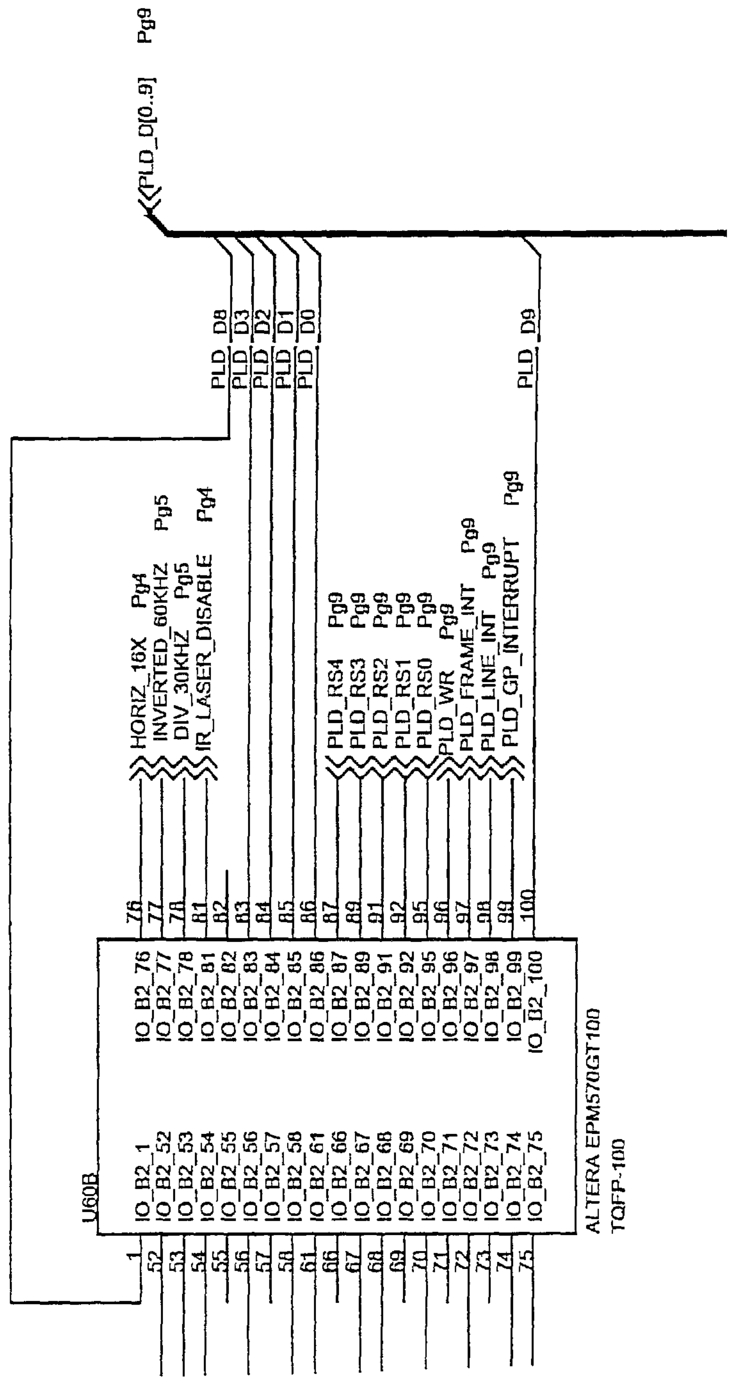
Figure 60C:
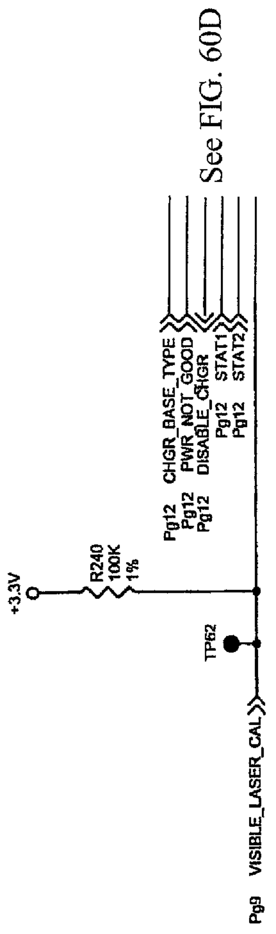
Figure 60D:
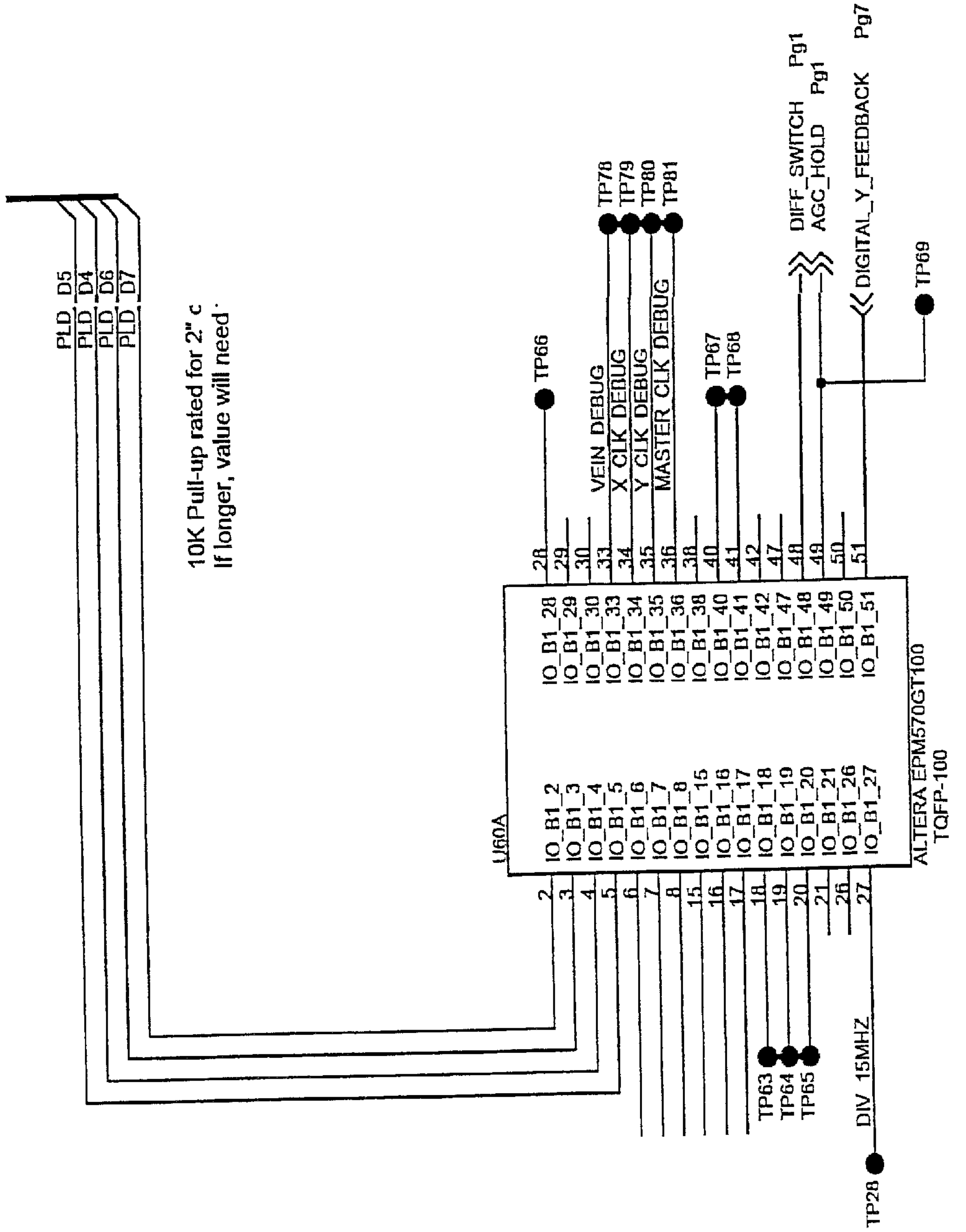
Figure 60E:
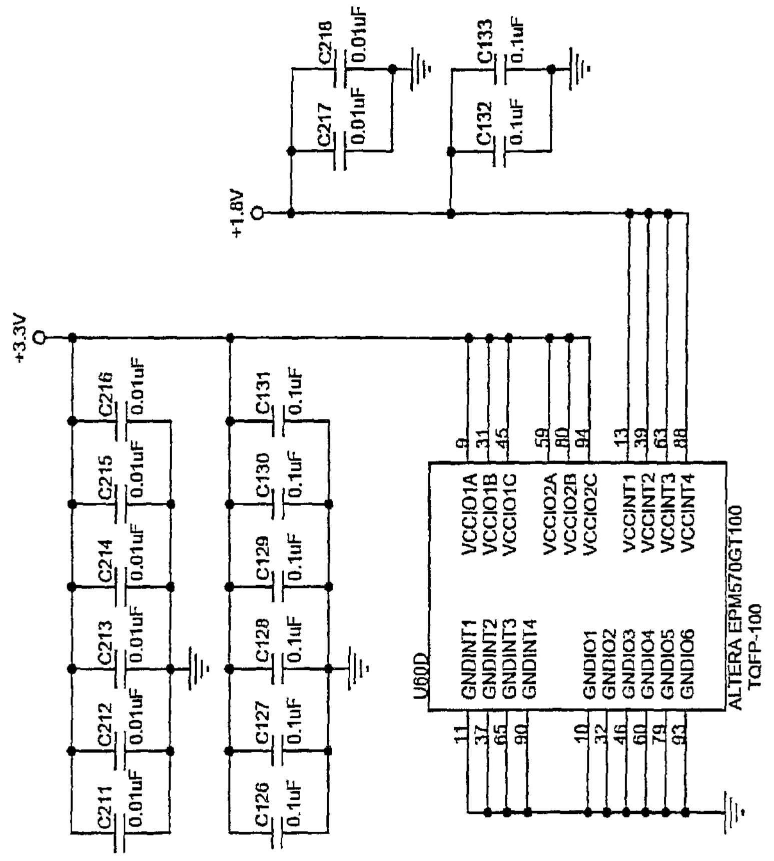
Figure 60F:
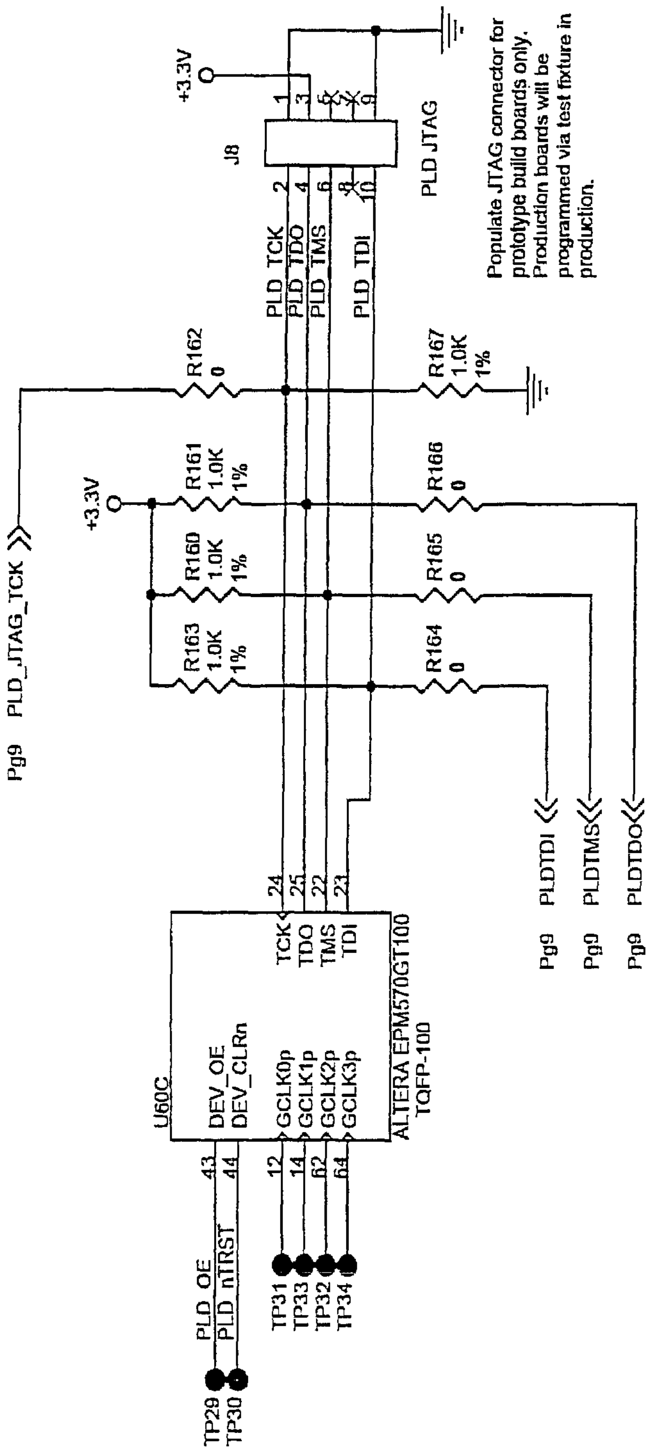
Figure 61A:
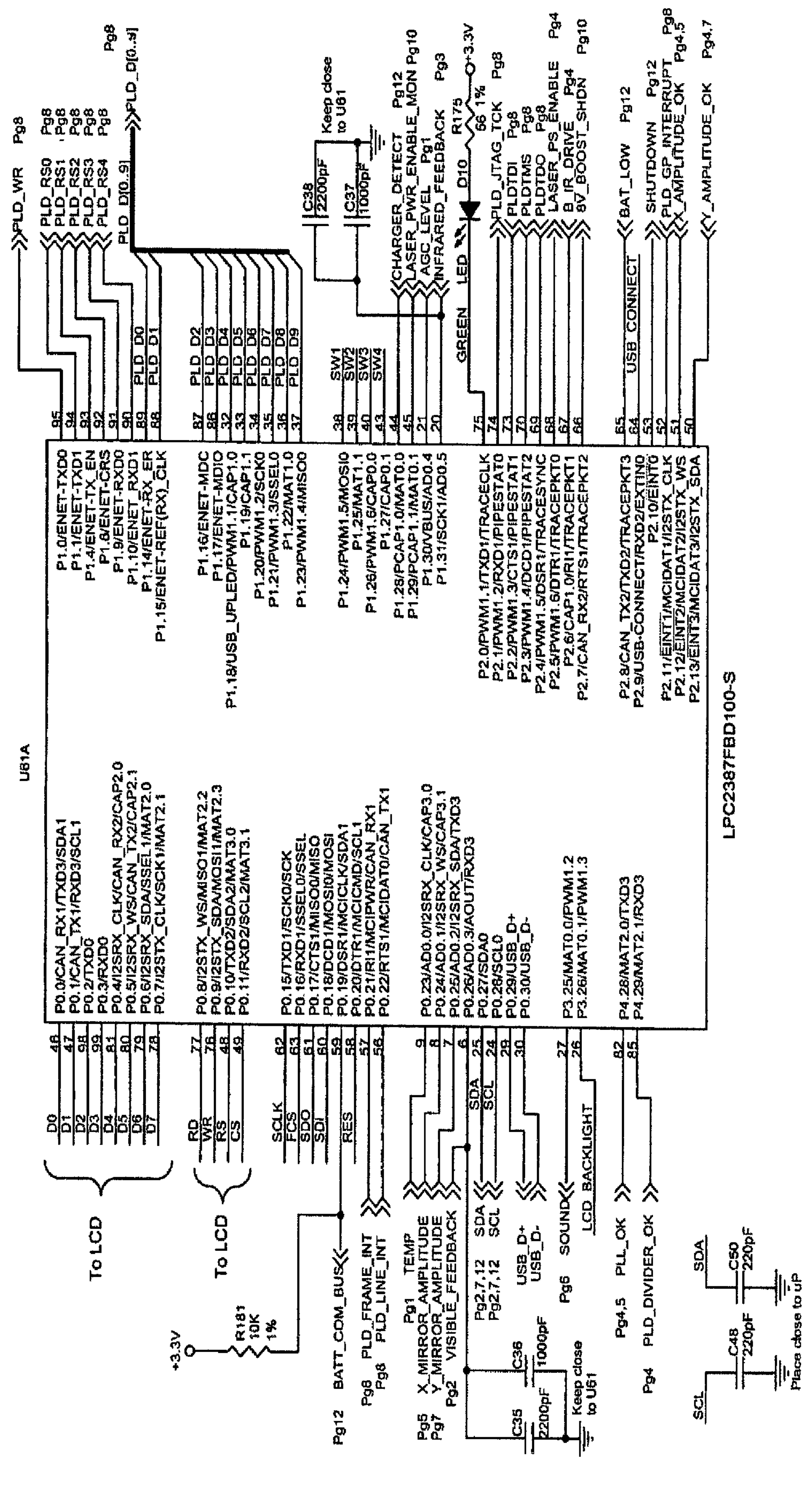
FIGS. 61A-E is a schematic of a circuit diagram of a microcontroller of the present invention.
Figure 61B:
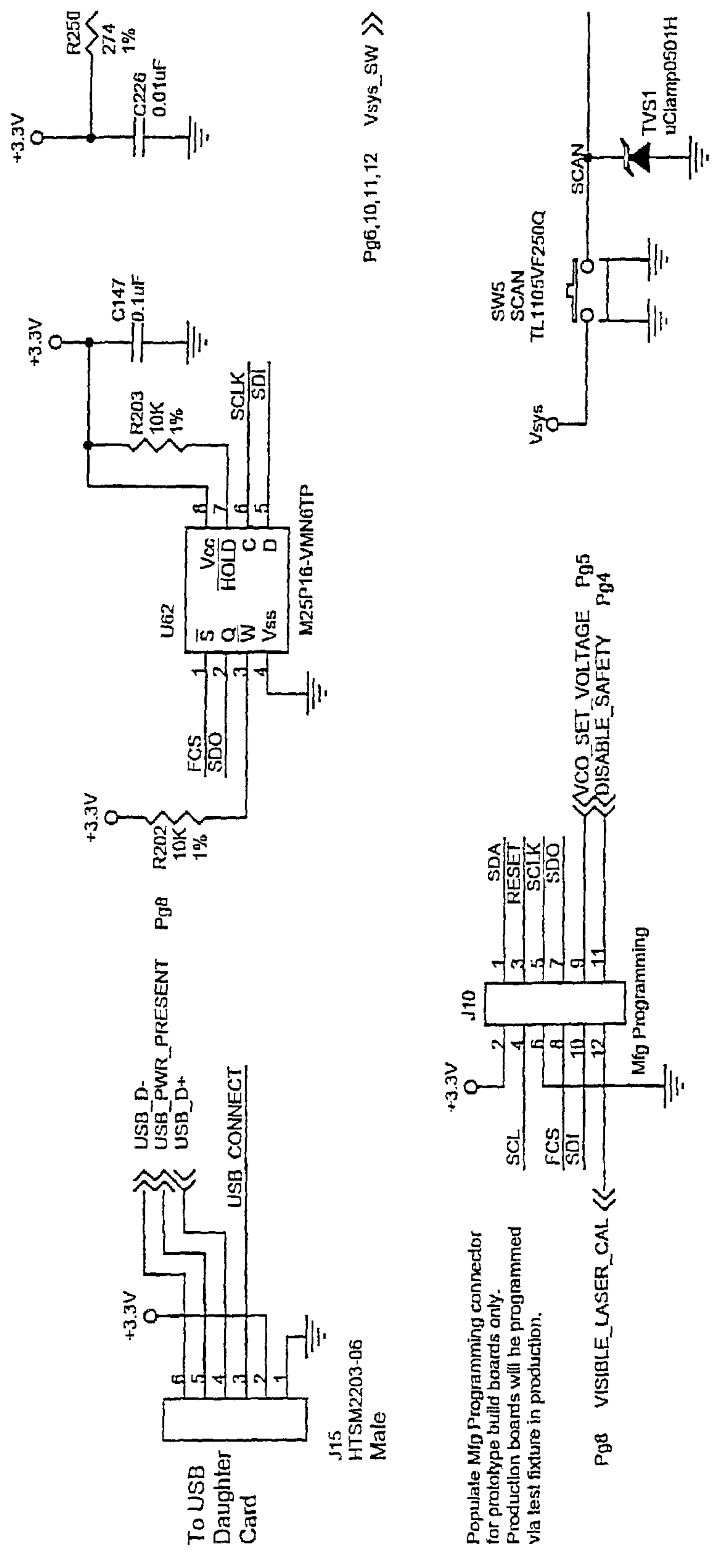
Figure 61C:
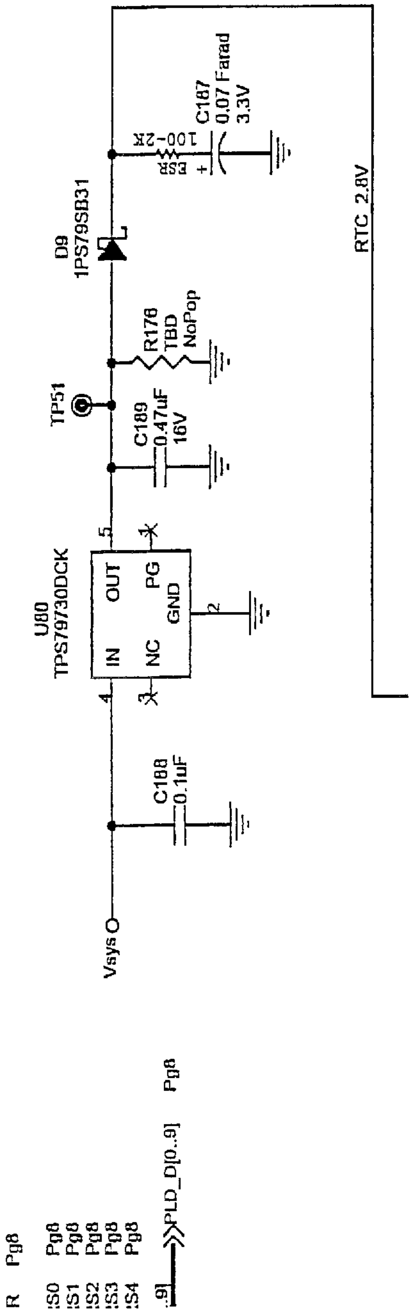
Figure 61D:
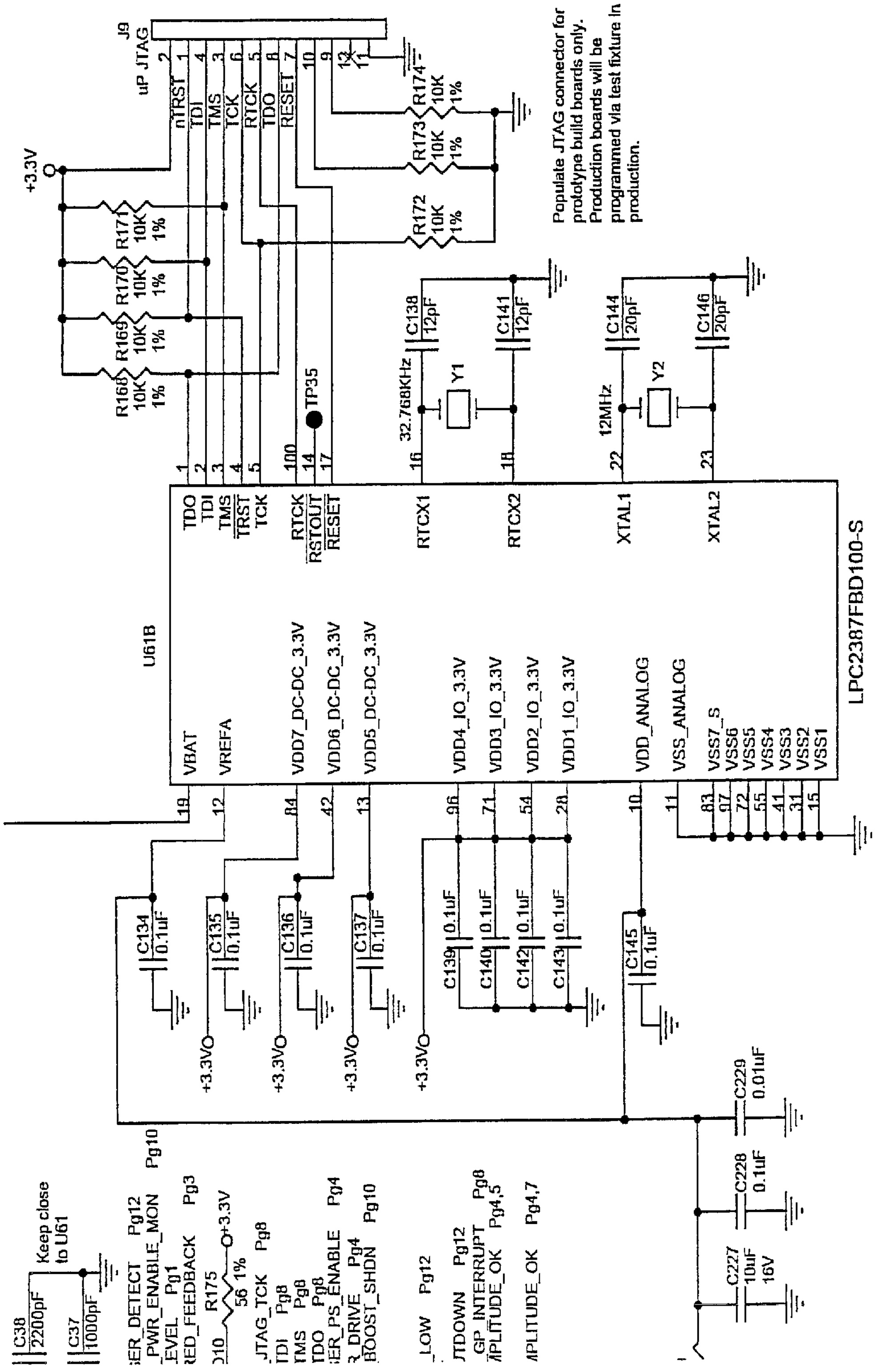
Figure 61E:
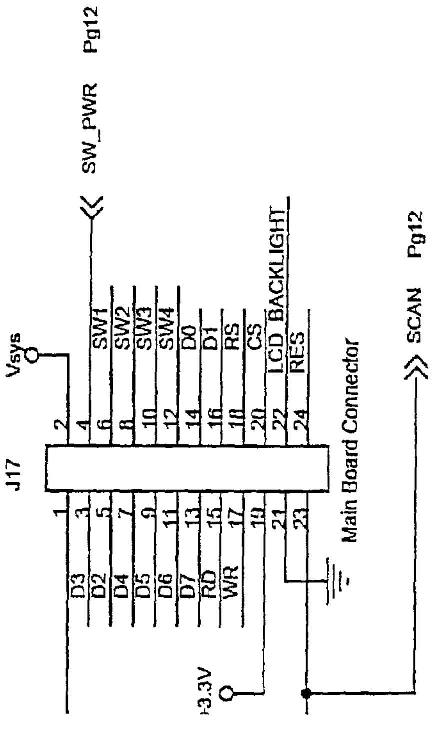
Figure 62A:
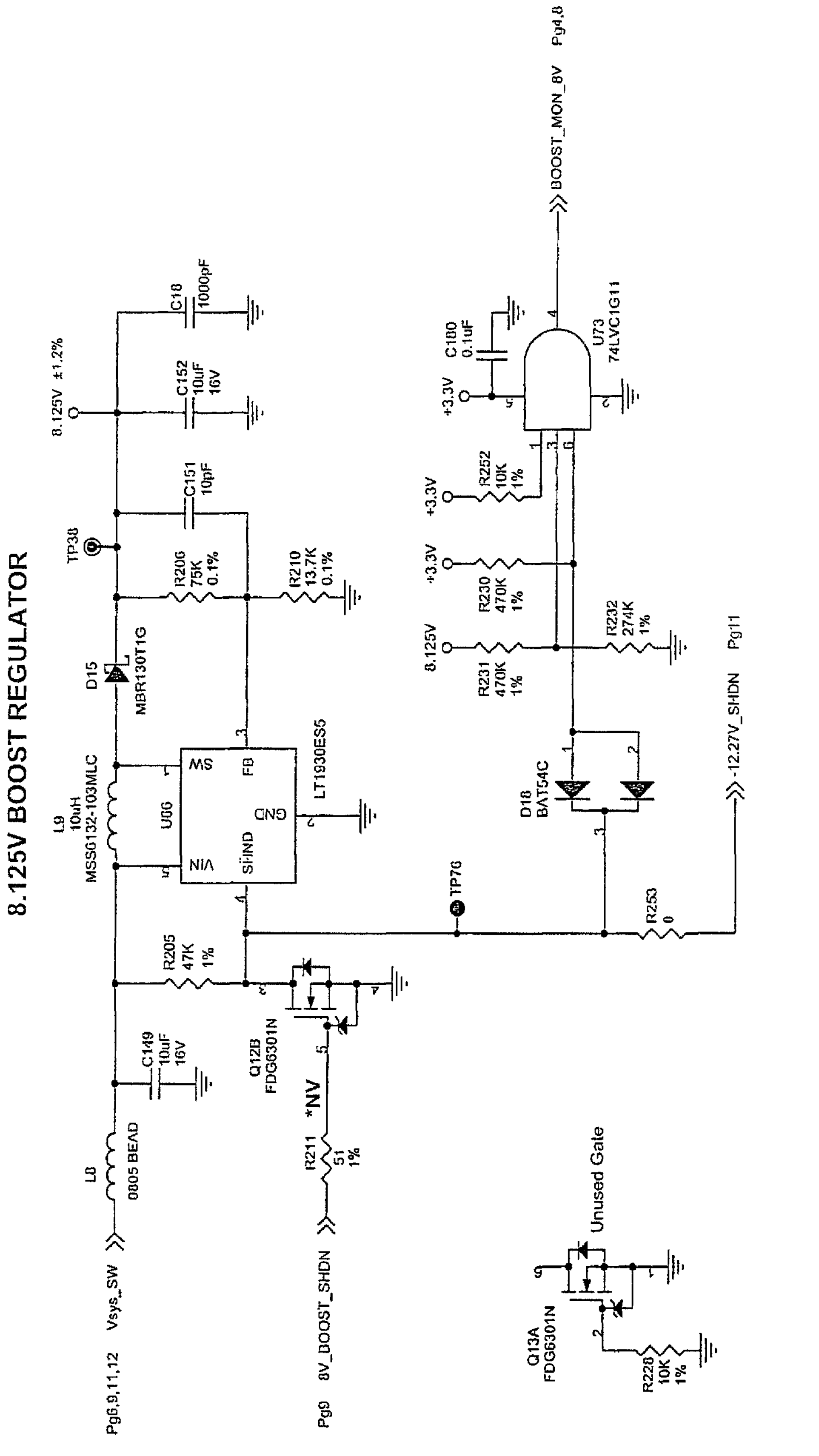
FIGS. 62A-D is a schematic of a circuit diagram of the power supply of the present invention.
Figure 62B:
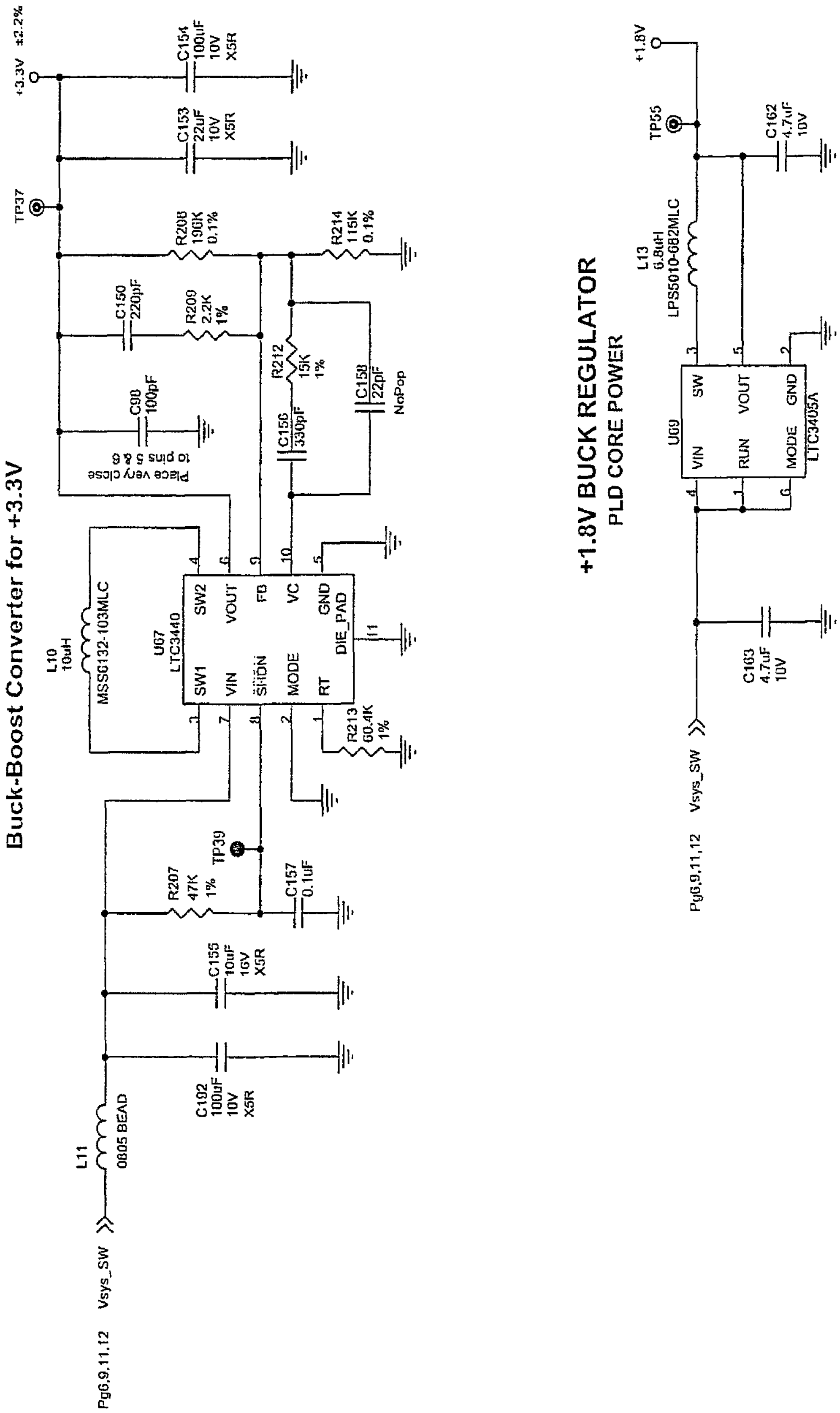
Figure 62C:
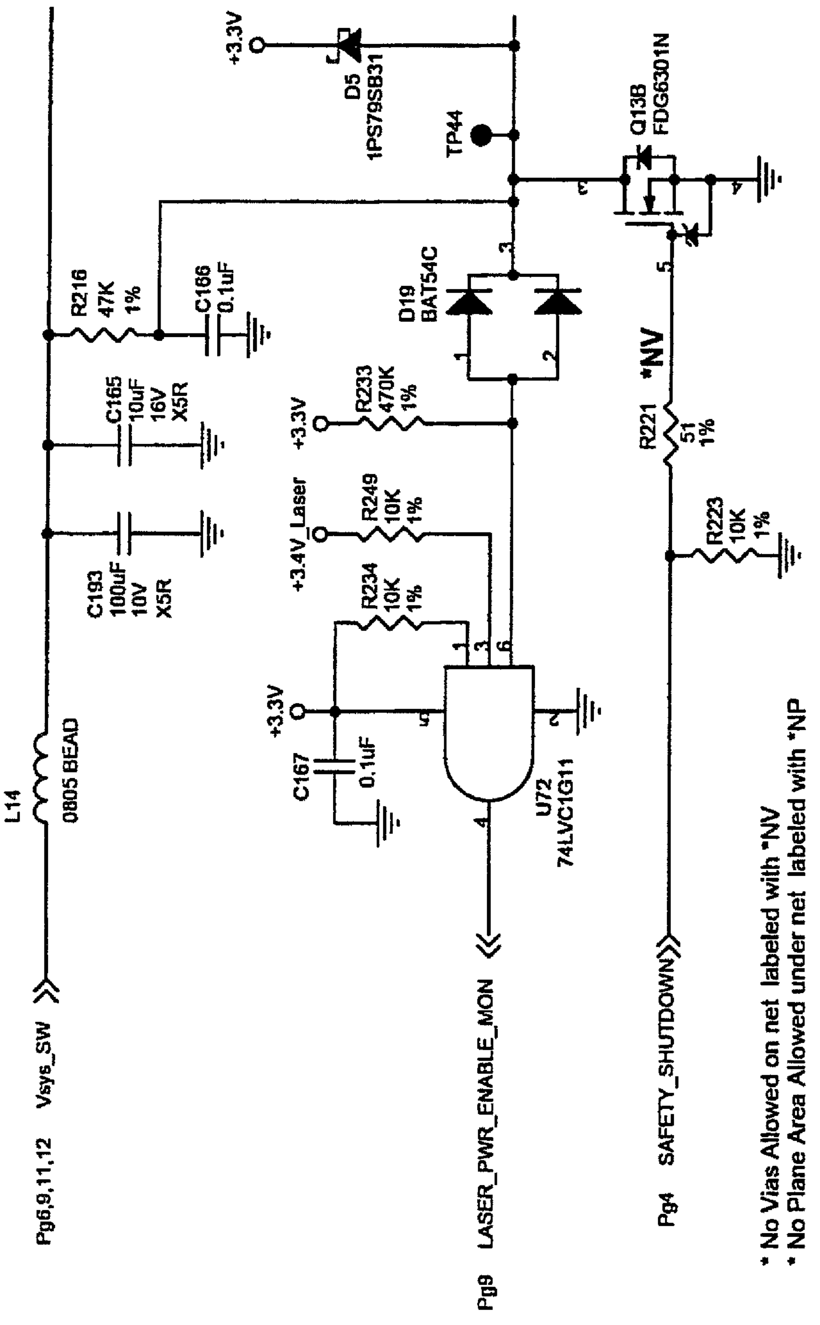
Figure 62D:
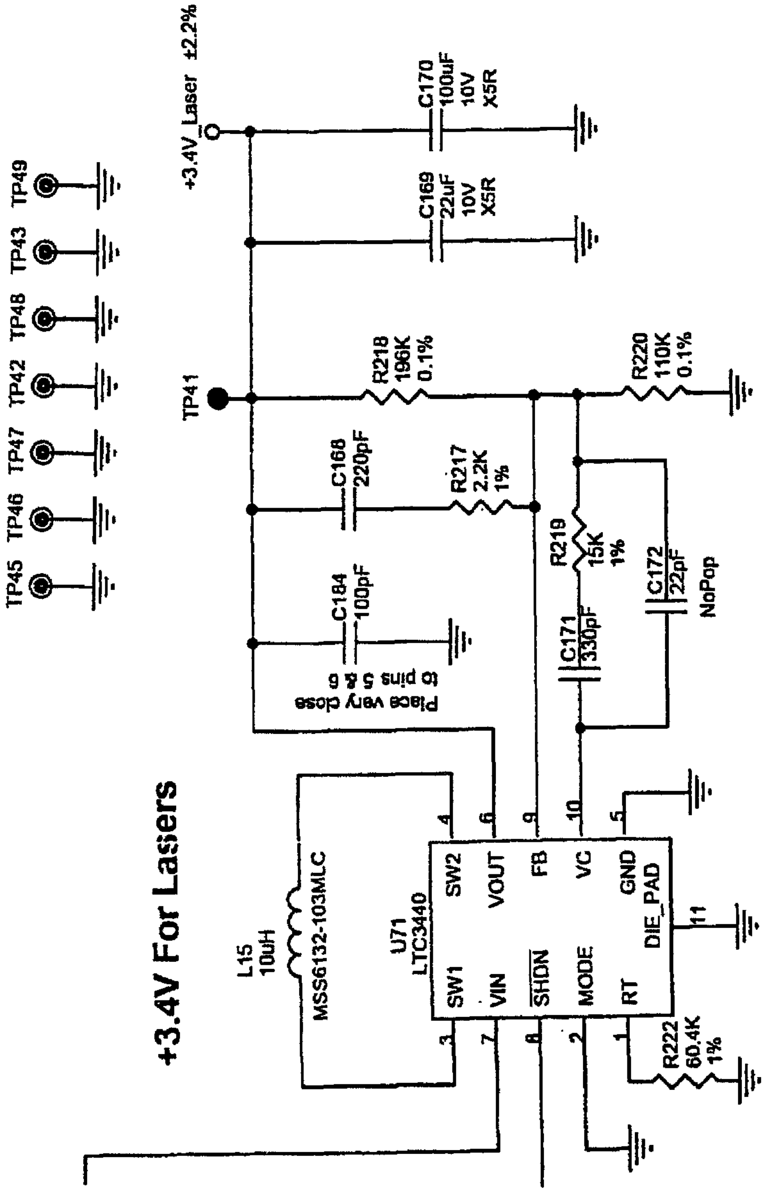
Figure 63A:
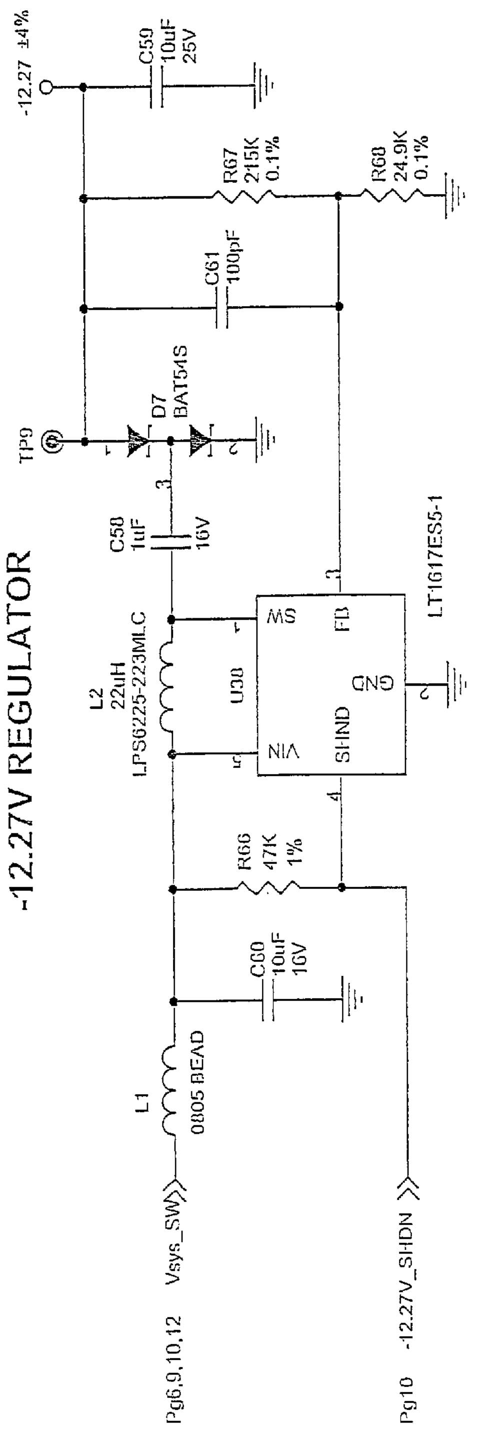
FIGS. 63A-B is an additional schematic of a circuit diagram of the power supply and its peripheral connections.
Figure 63B:
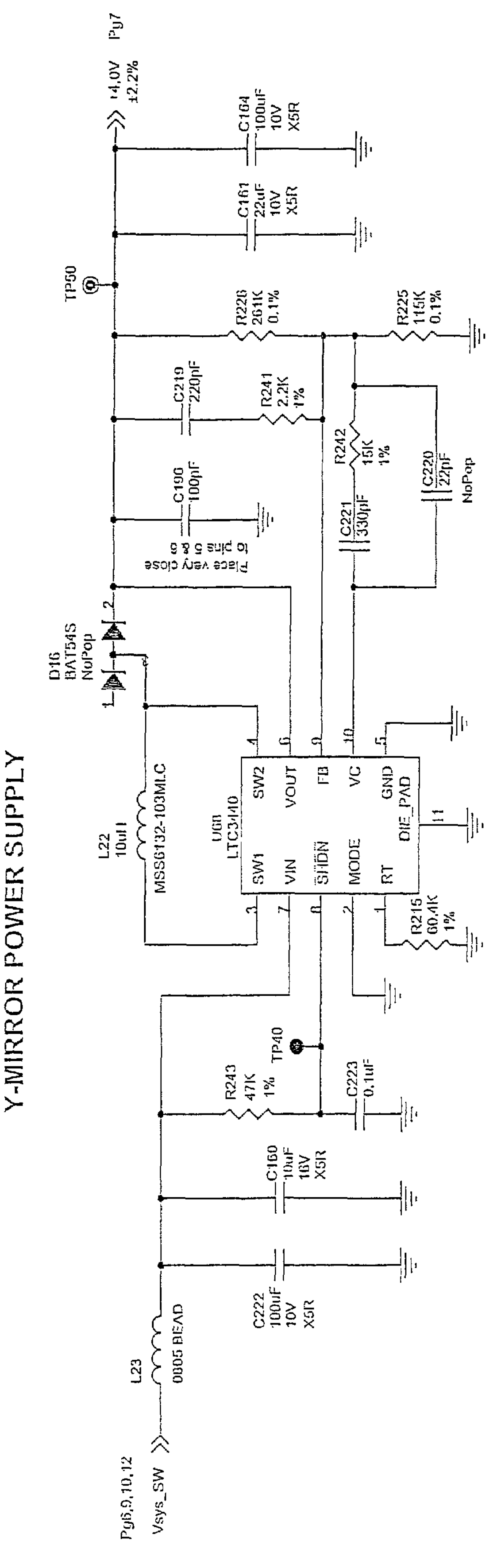
Figure 64A:
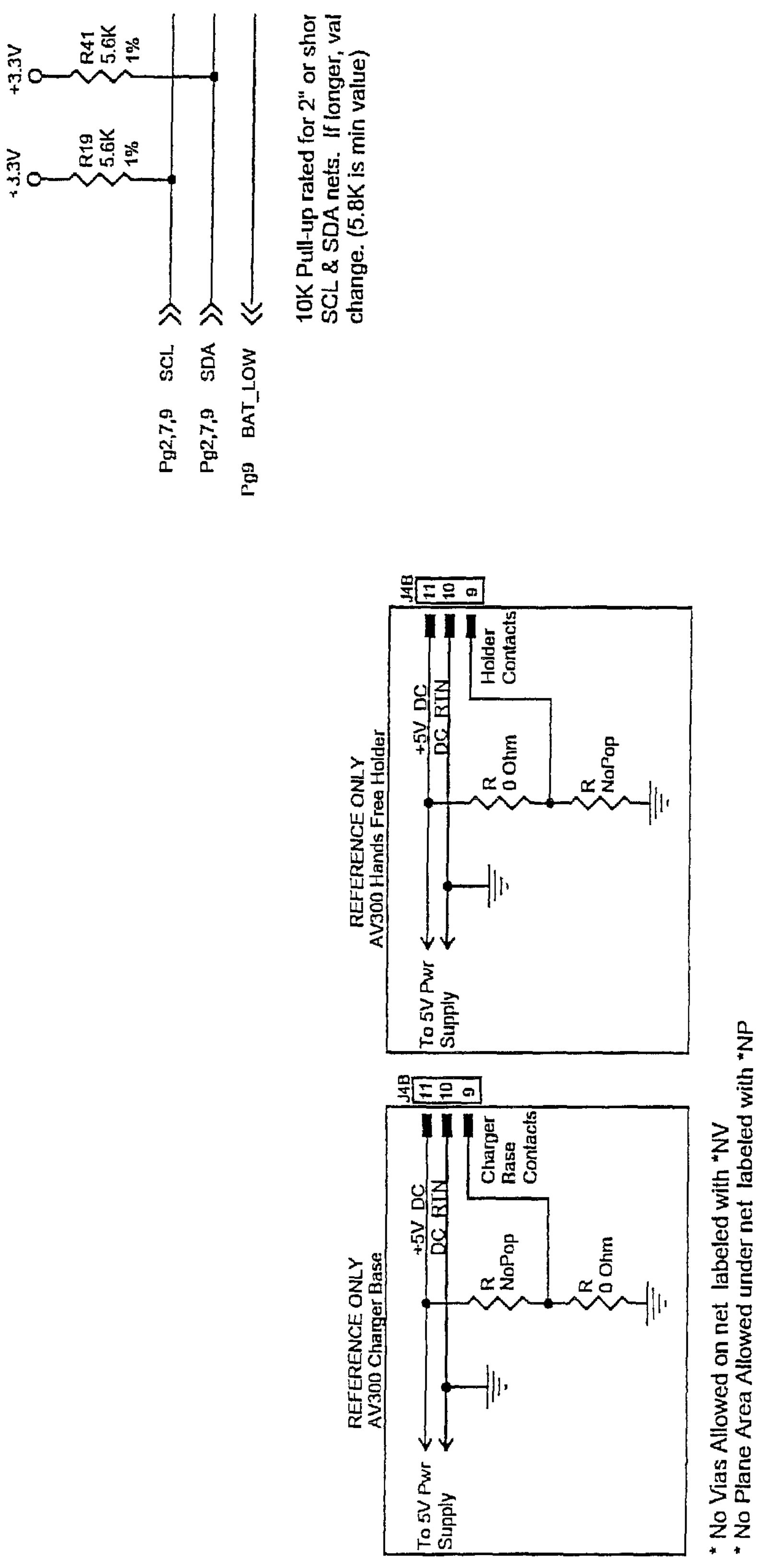
FIGS. 64A-E is a schematic of a circuit diagram of the battery management system.
Figure 64B:
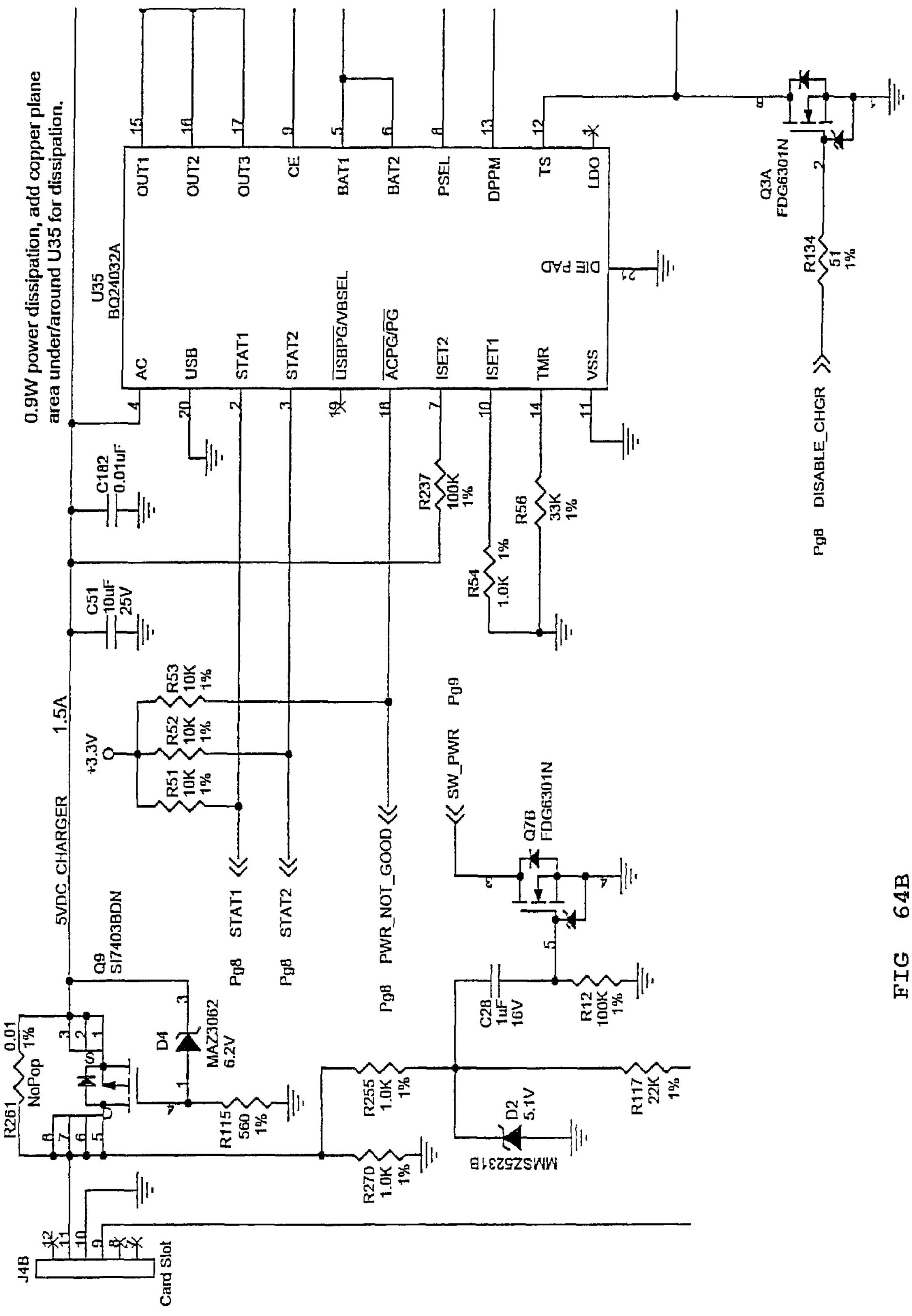
Figure 64C:
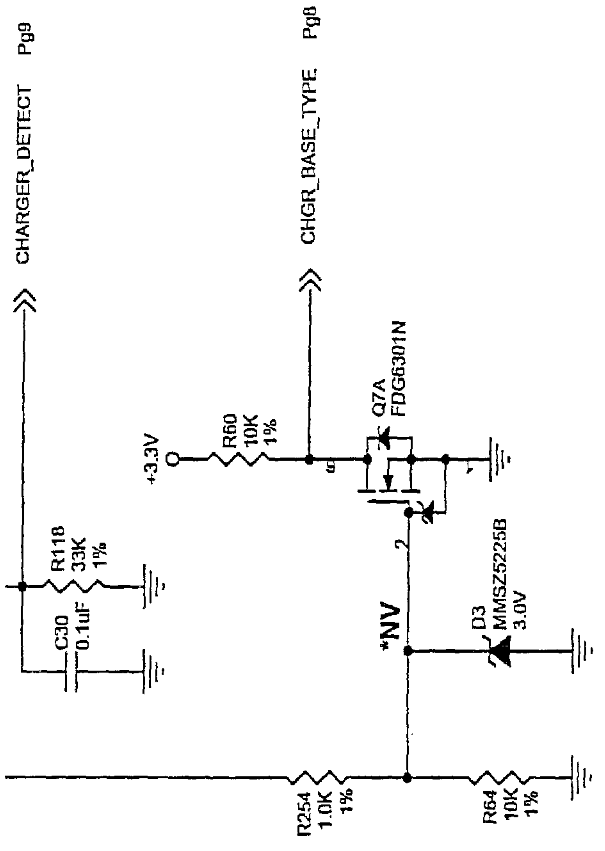
Figure 64D:
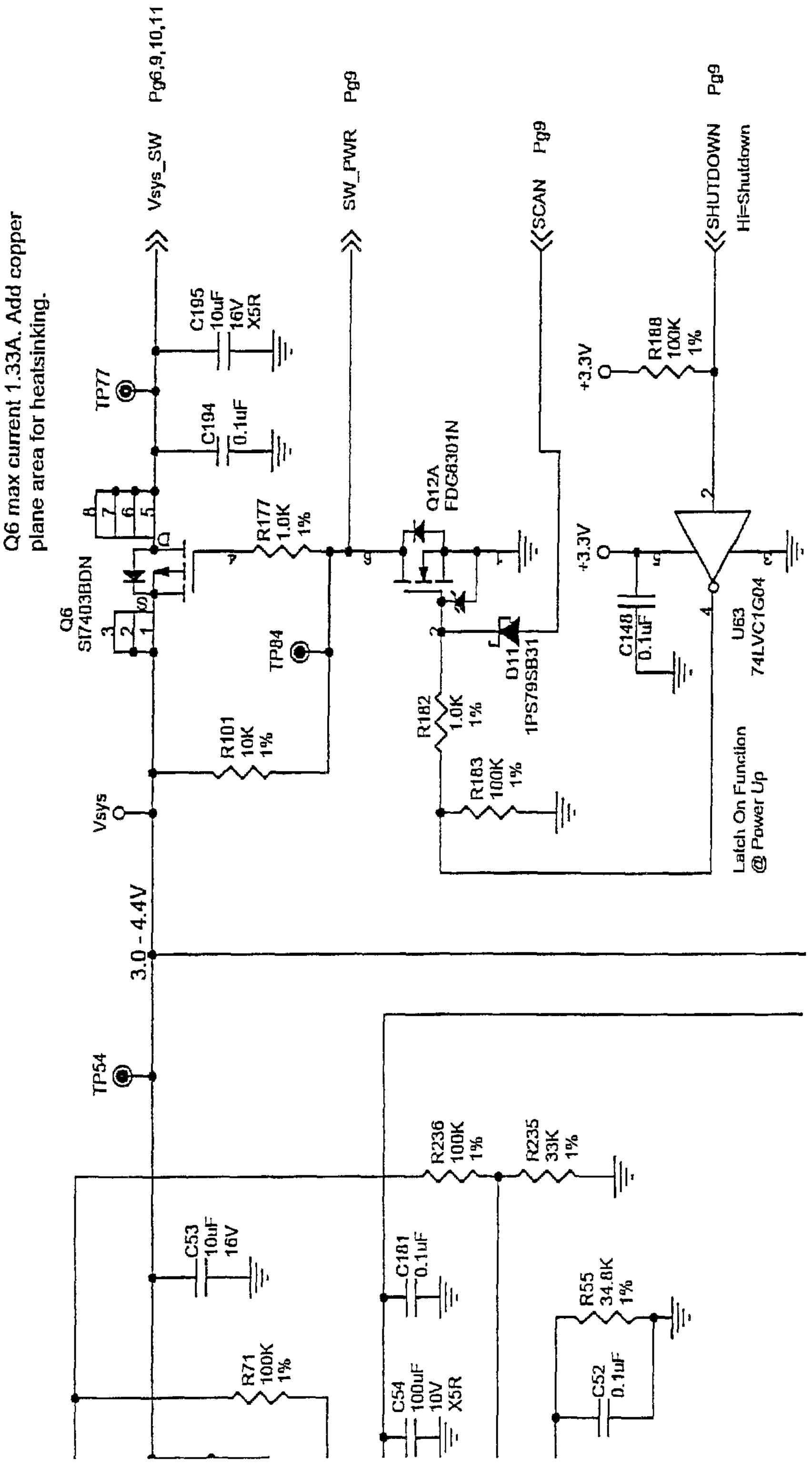
Figure 64E:
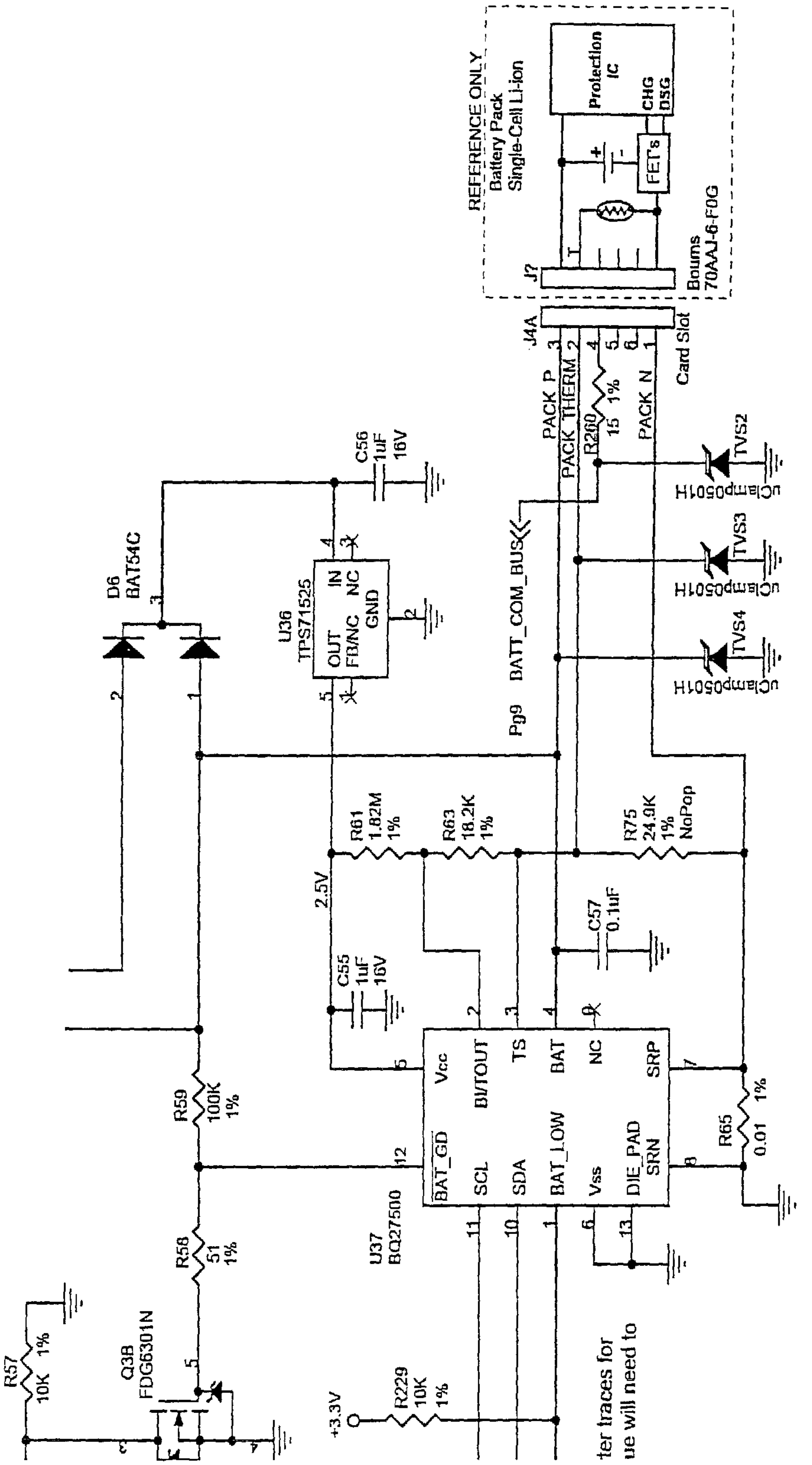
Figure 65A:
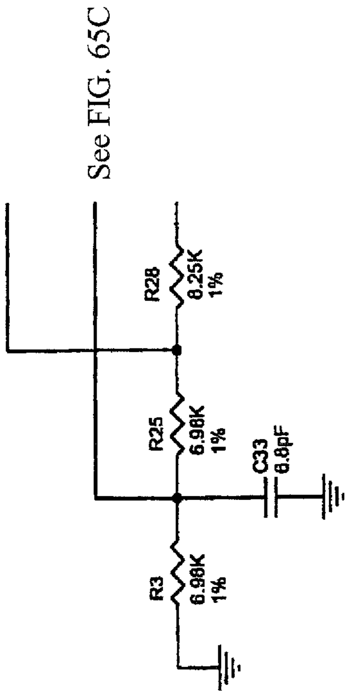
FIGS. 65A-D a schematic of a circuit diagram of the photodiode engine.
Figure 65B:
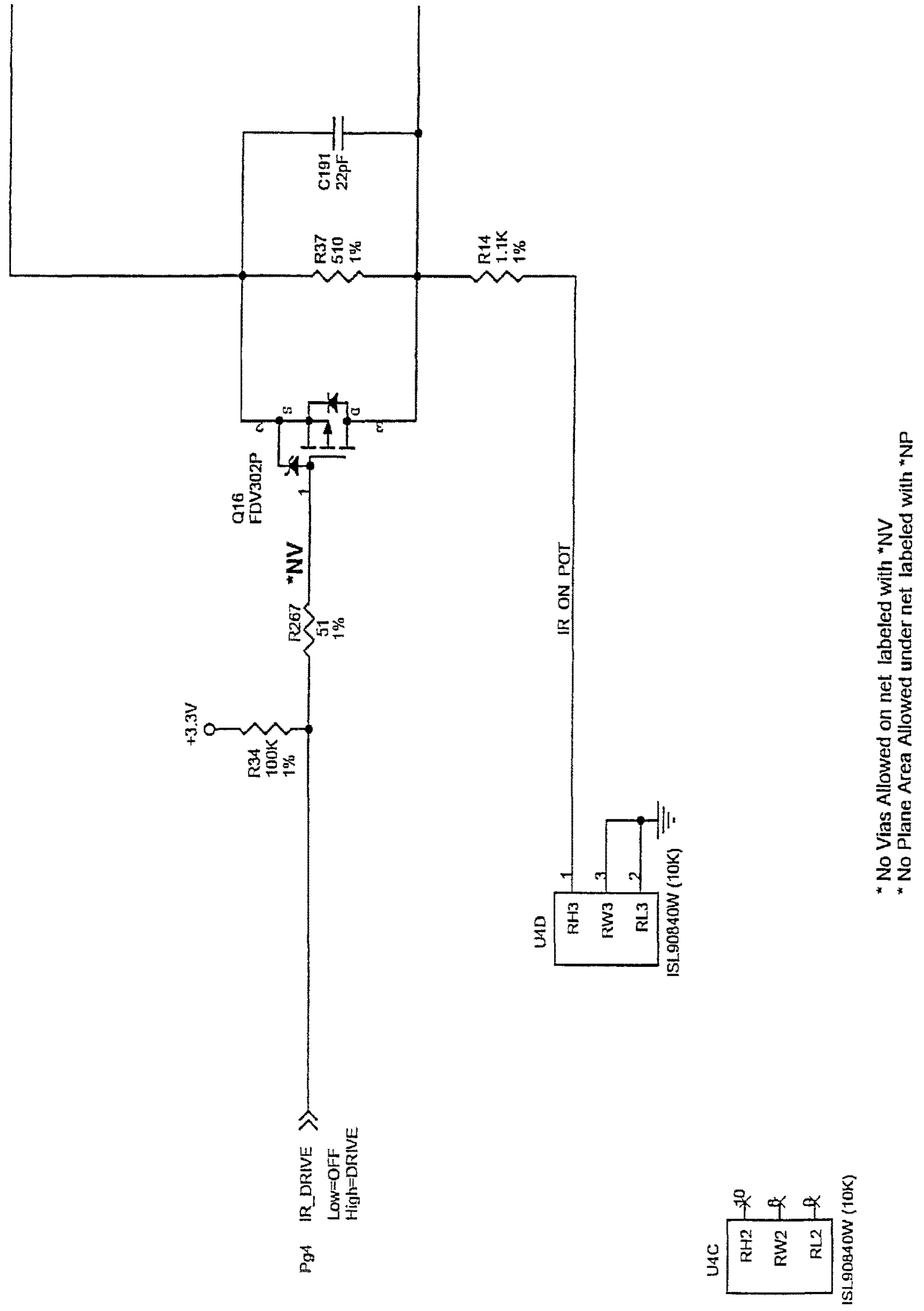
Figure 65C:
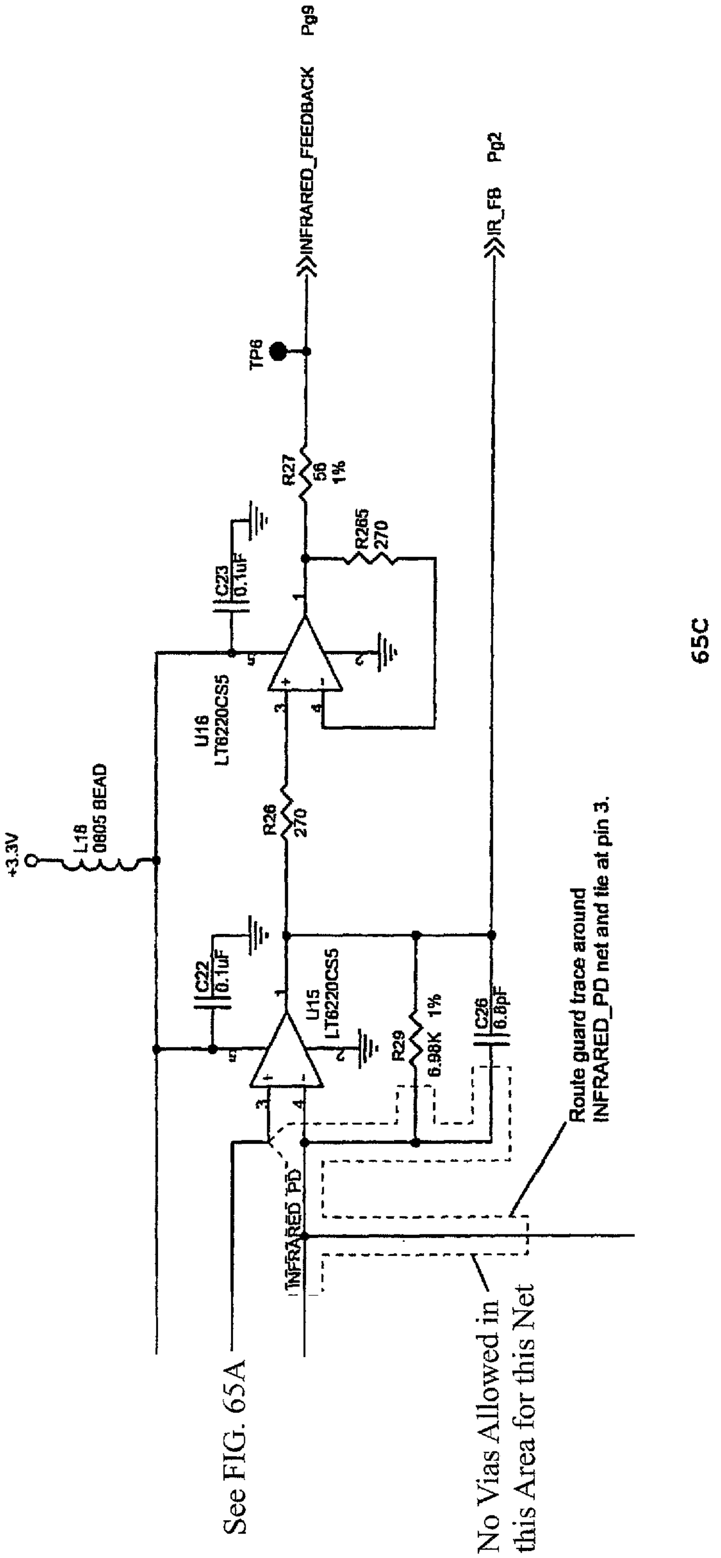
Figure 65D:
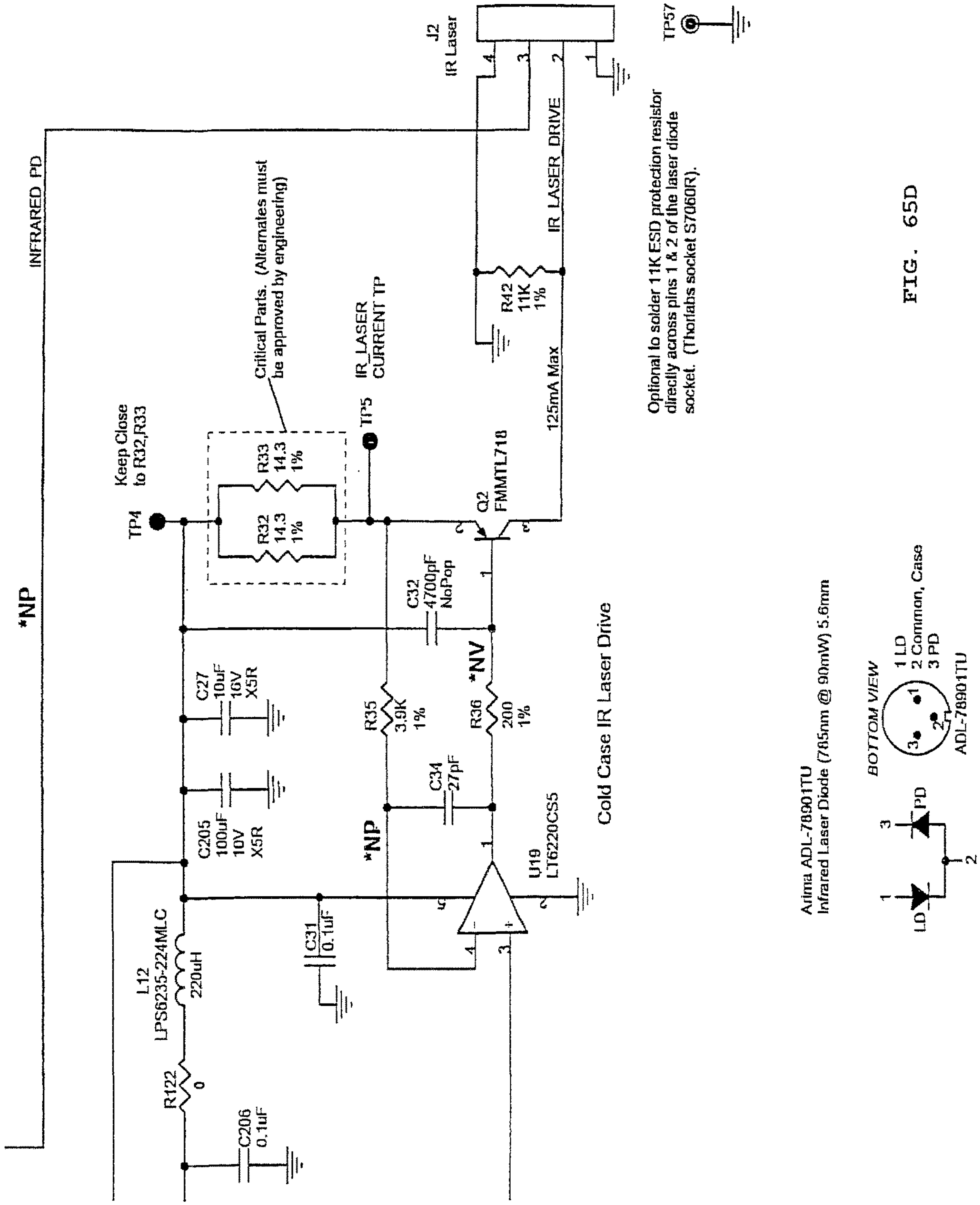
Figure 66A:
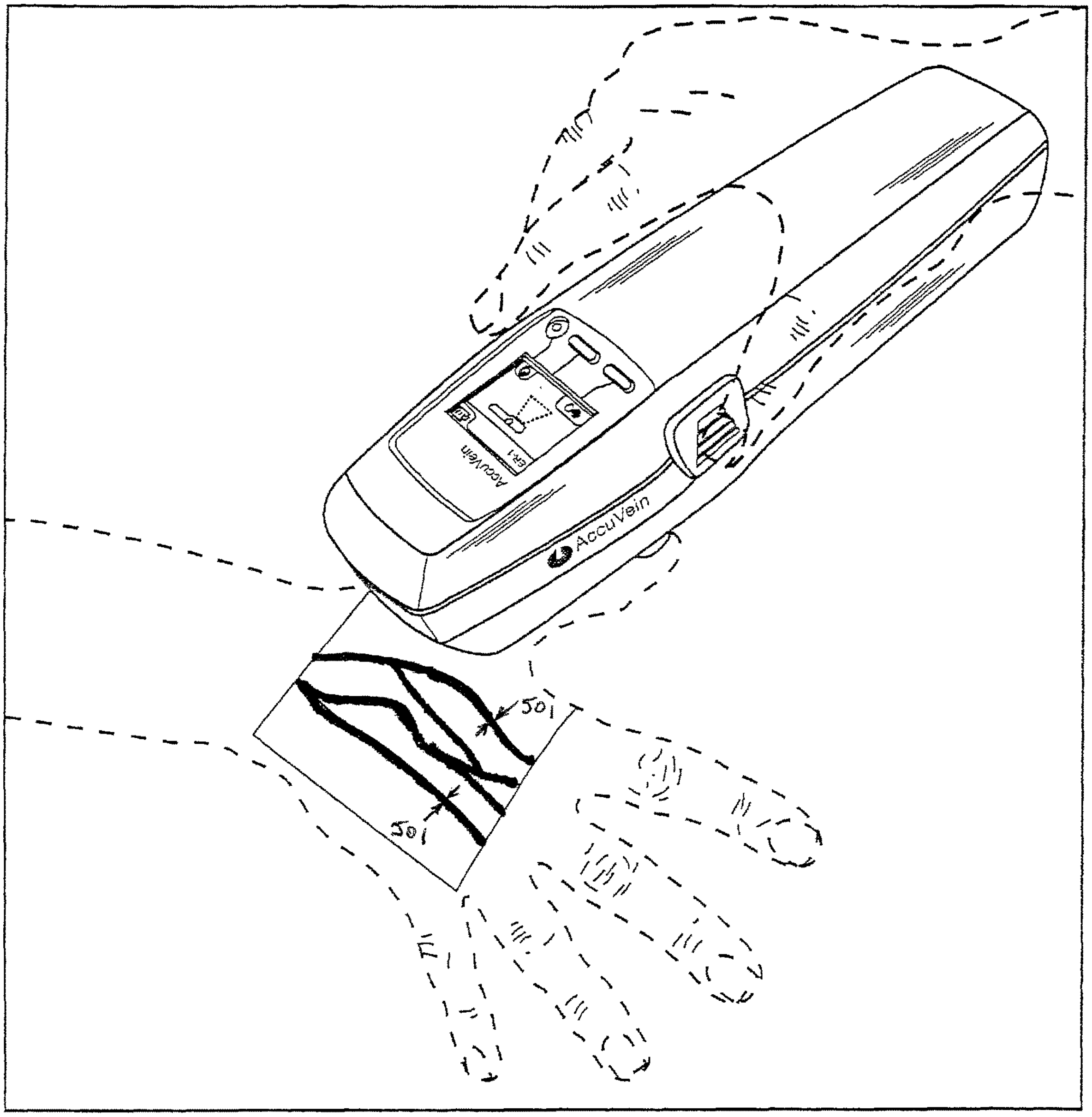
FIGS. 66A-E illustrates the graphical or symbolic information that may be projected onto a patient other than just vein imaging.
Figure 66B:
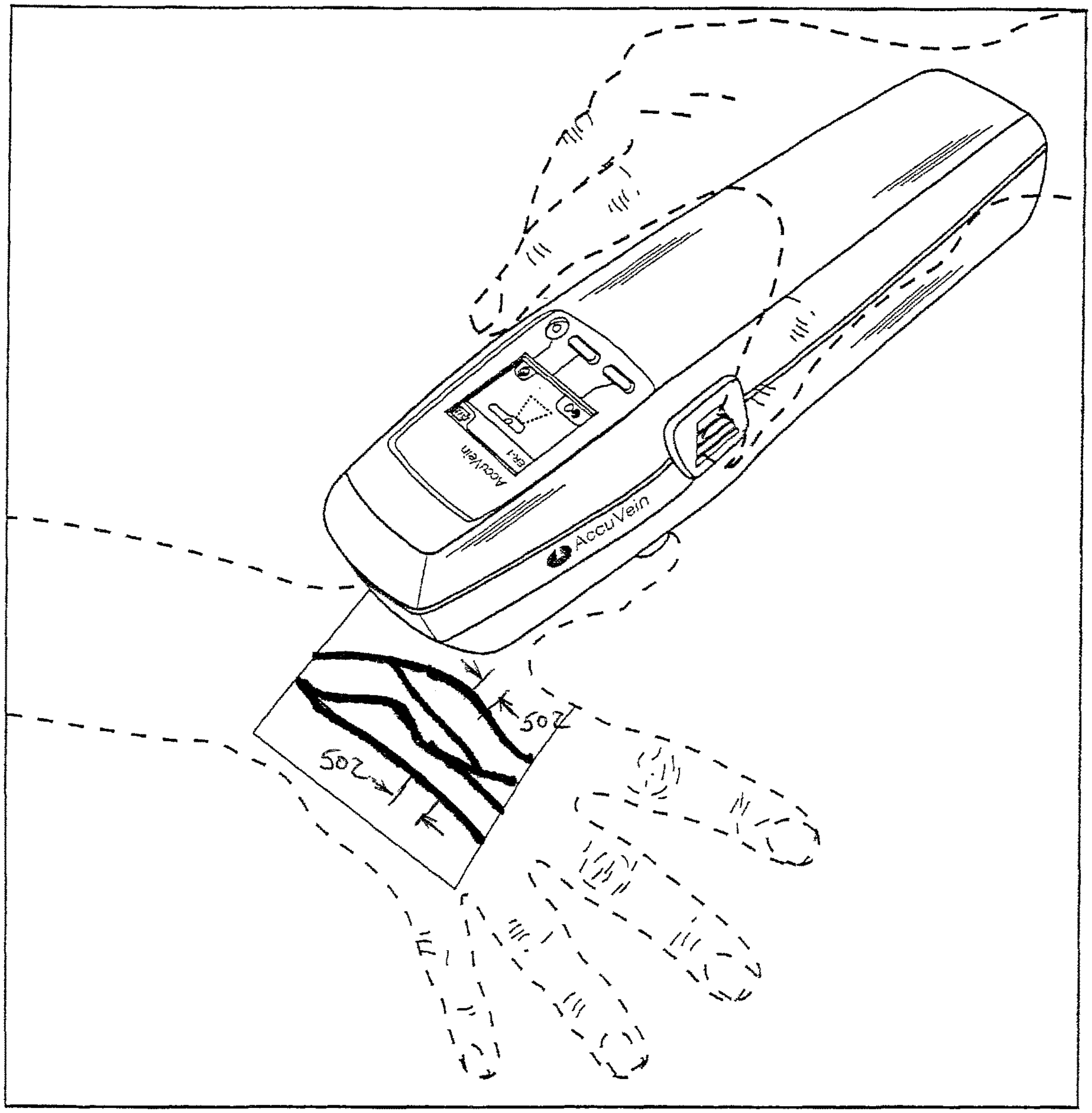
Figure 66C:
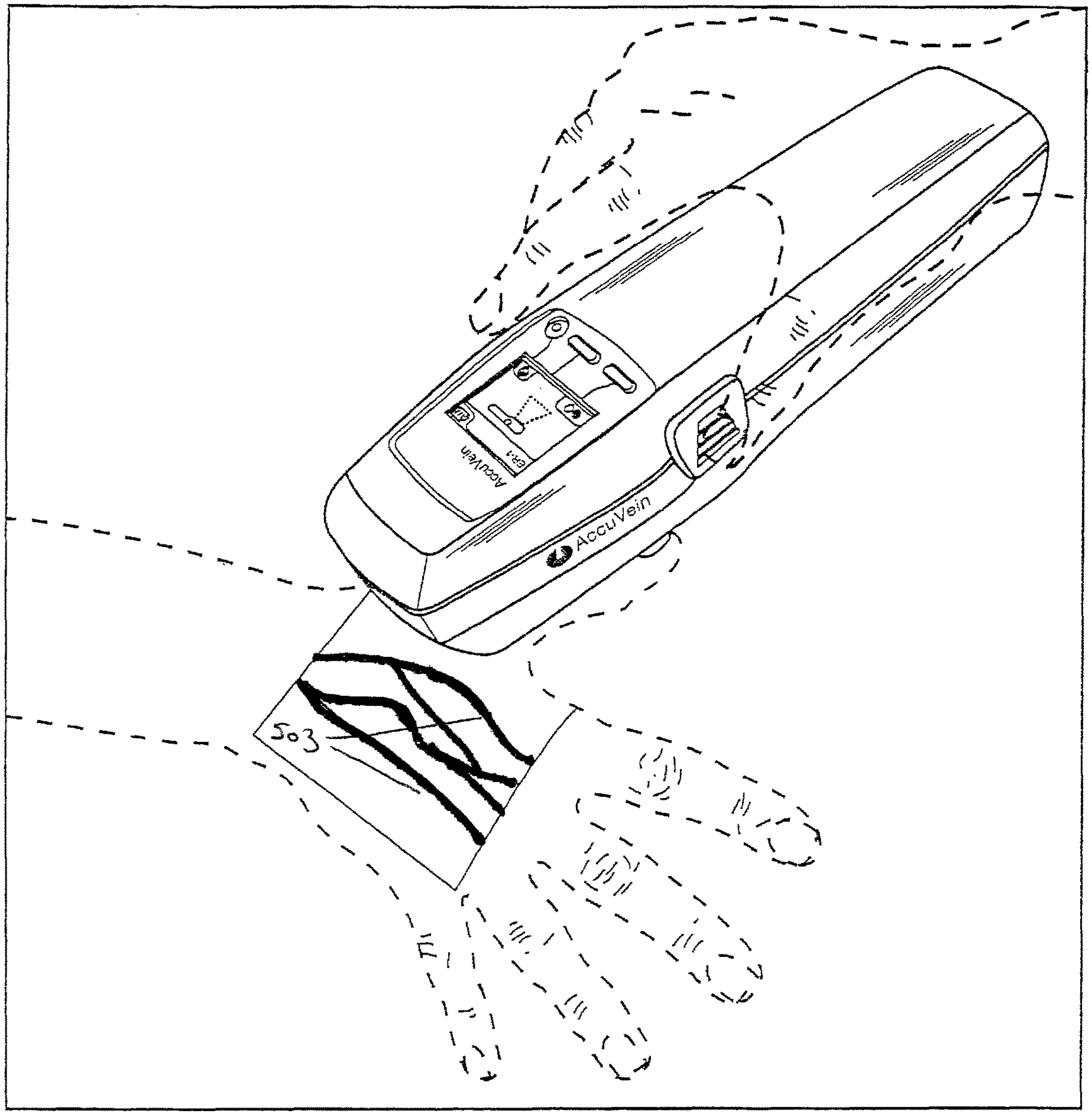
Figure 66D:
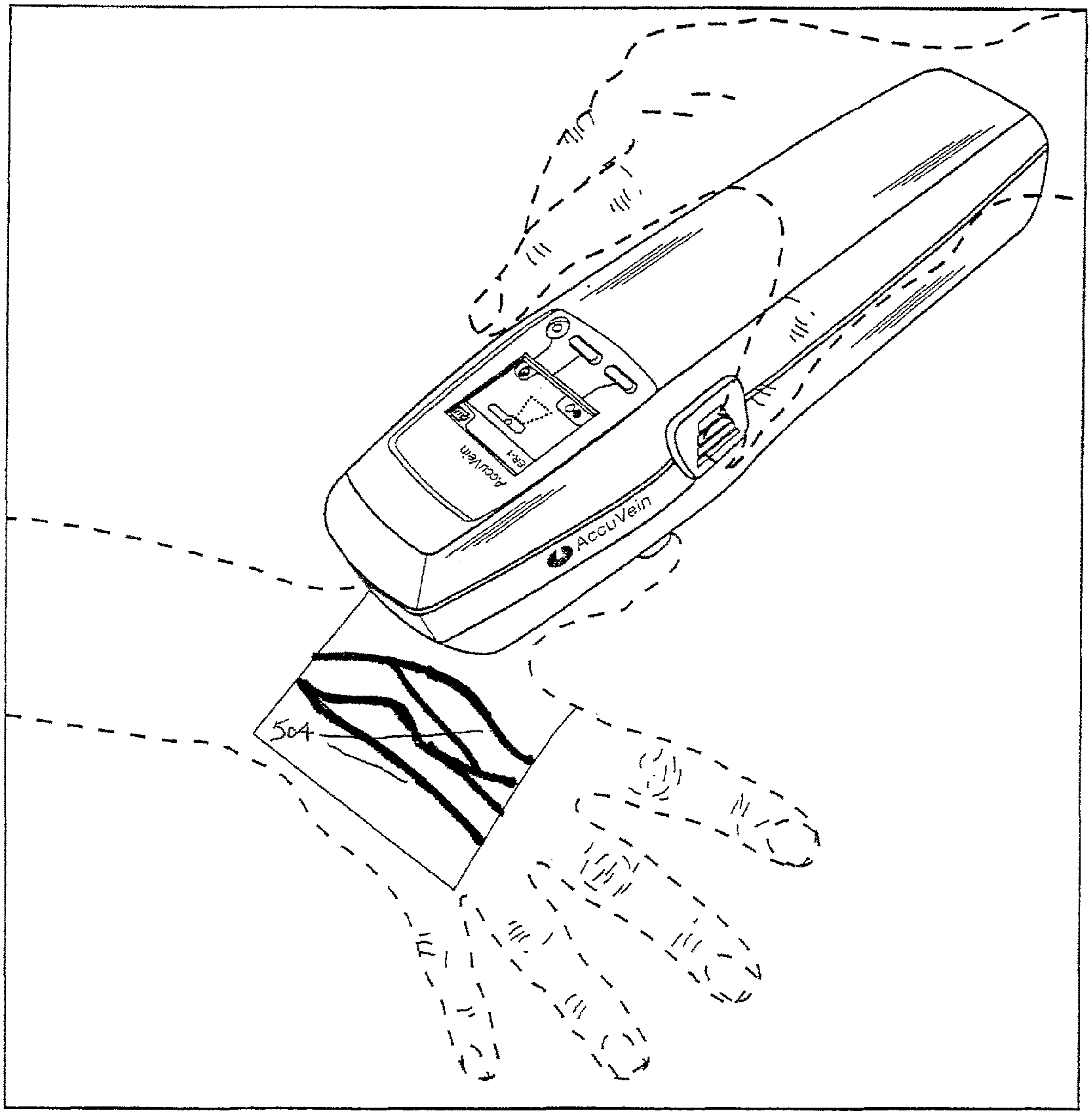
Figure 66E:
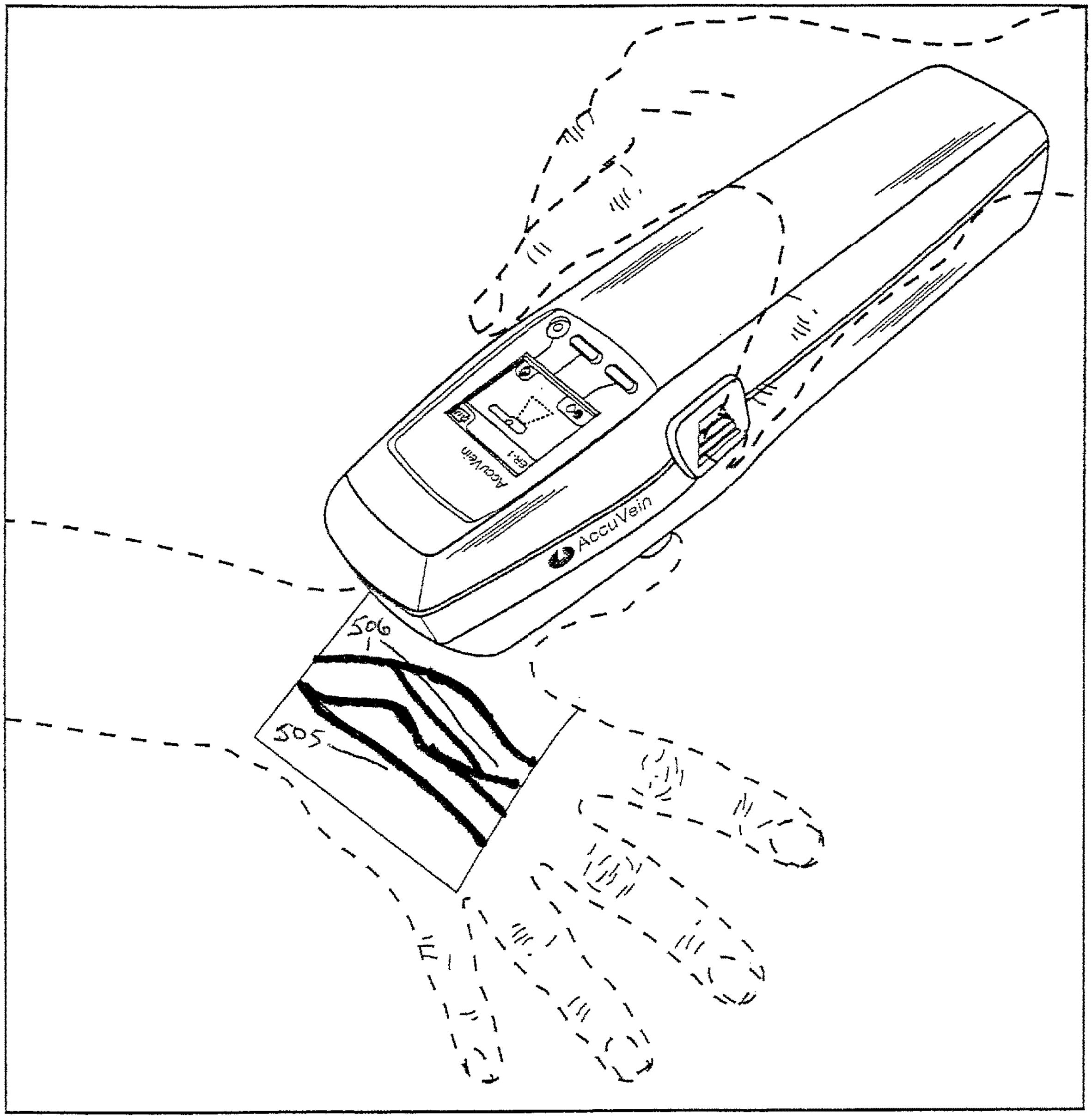

Mounted inside the battery compartment formed by walls 26A-26E may be the battery pack 16. The battery pack 16 (FIG. 13) can be any of a variety of models known in the art, but in a preferred embodiment, it may be rectangular to fit inside the compartment formed by walls 26A-26E. One end 16A of the battery pack 16 may be adapted to be received by the power connection 95 on the main circuit board (FIG. 30). The battery pack 16 may be secured in the battery compartment by a battery cover 96 which attaches to the bottom section 18 of housing 11. The battery cover 96 may attach to the bottom section of the housing 18 in a variety of ways, such as by clips or screws. As seen in FIG. 47, the battery cover 96 may be secured by having a pair of flanges 96A extending therefrom be received in a pair of slots 34 in the bottom section 18 of housing 11. FIGS. 62-64 are schematics of circuit diagrams which demonstrate how the battery pack is connected to the internal circuitry 12, the scanner assembly 15, and remaining electrical components of the invention.

Figure 37:
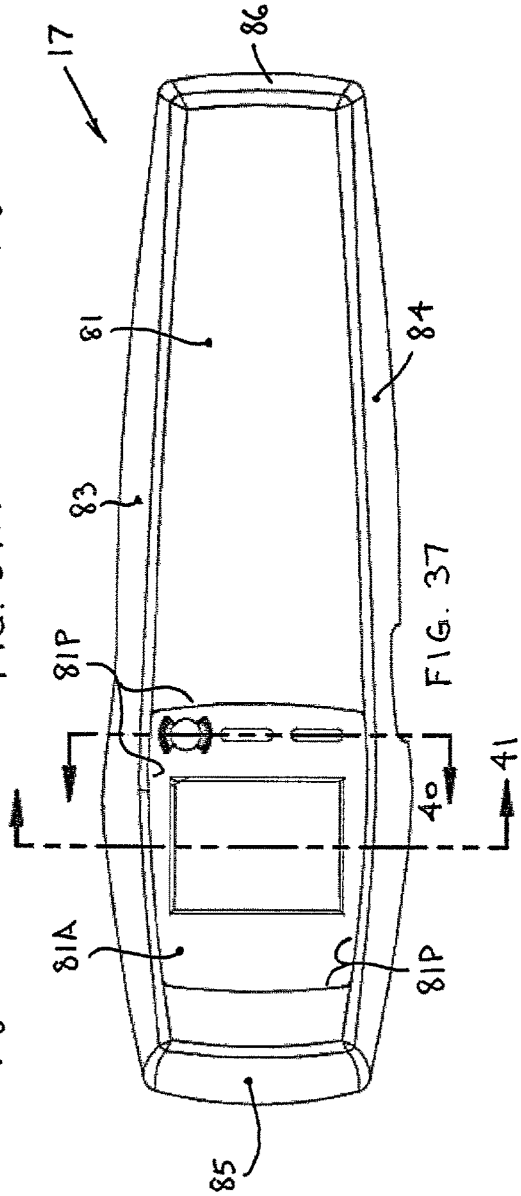
FIG. 37 is a top view of the top section of the housing.
Figure 38:
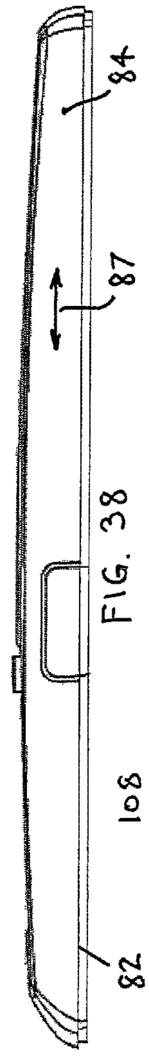
FIG. 38 is a side view of the top section of the housing.
Figure 39:
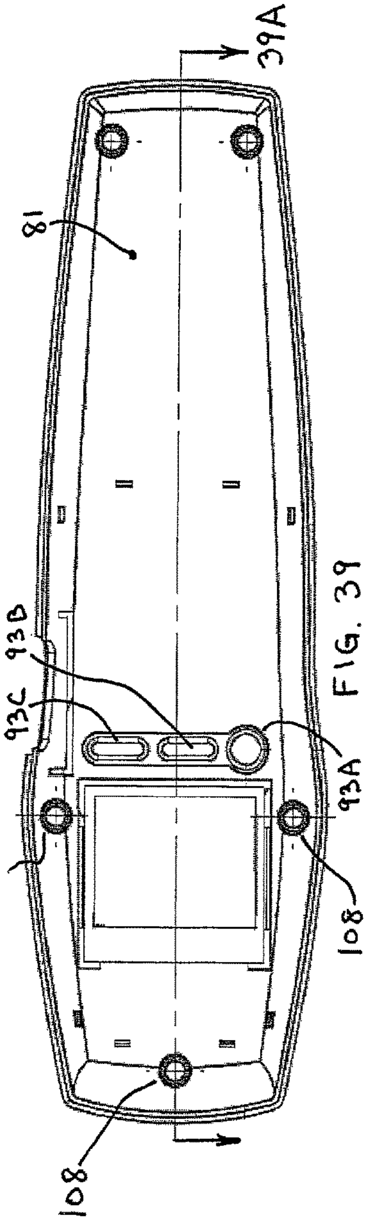
FIG. 39 is a bottom view of the top section of the housing.
Figure 41:
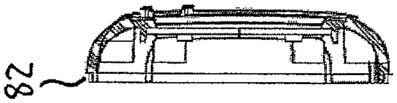
FIG. 41 is a second cross-section through the bottom section of the housing.

FIGS. 37-41 show a representation of one embodiment of the top section 17 of the housing 11. The housing top section 17 may be formed similar to the housing bottom section 18, and thus may have a top wall 81 from which extends, generally at an angle, a left sidewall 83 and right sidewall 84, and a front wall 85 and rear wall 86. The front wall 85 and rear wall 86 may extend from the left sidewall 83 and right sidewall 84, respectively, creating an internal cavity 87. FIG. 37 shows the outer surfaces of those walls, while FIG. 39 shows the inner surfaces of those walls. The walls 83-86 extend out to a generally planar edge 82, which may have a peripheral flange protruding therefrom to mate with the recess of the housing bottom section 18. In one embodiment, housing top section 17 may have extending down from top wall 81 and walls 83-86, towards the plane of the edge 82, one or more cylindrical members 108, which are adapted to receive mounting screws 106, and may include use of threaded inserts. The cylindrical members 108 of the housing top section 17 may be positioned to be in line with the corresponding members 107 of the housing bottom section 18 to be secured thereto during assembly of the scanner 10.

Figure 5:
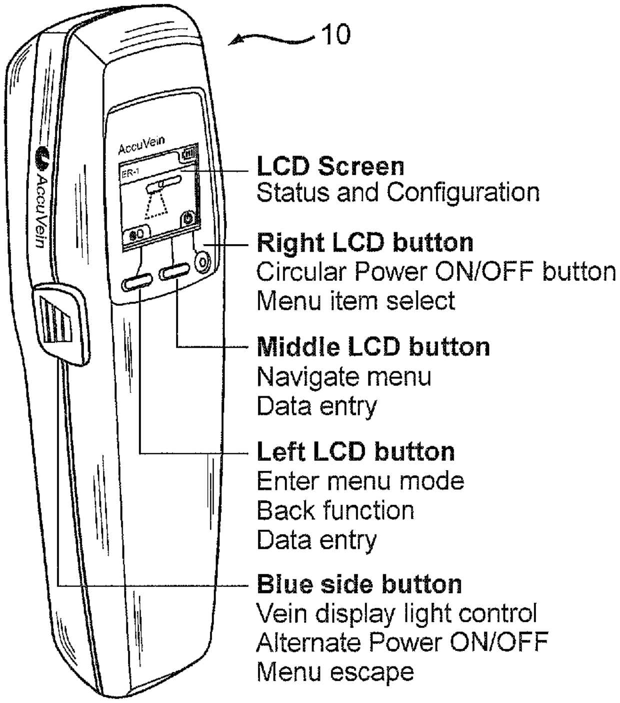
FIG. 5 is a side perspective view of the apparatus of FIG. 1, highlighting the buttons and LCD screen of the device of FIG. 1.

The outer surface of the top wall 81 of the housing top section 17 may have a step down into a flat recessed region 81A having an edge periphery 81P. That flat recessed region 81A may comprise of an opening 91 through to the inside surface, which may be a rectangular opening, and a plurality of shaped orifices 93A, 93B, and 93C. The rectangular-shaped opening 91 may be sized and otherwise adapted to receive the display 14, which is discussed in more detail hereinafter. The flat recessed region 81A of top wall 81 may receive a display guard 92 (FIG. 30), to provide a barrier between the display 14 and the outside environment. The plurality of shaped orifices 93, which may also be correspondingly found in the display guard 92, are adapted to receive a plurality of buttons 77 or other activating means which may be mounted directly under the top plate 81 of the housing top section 17. In a preferred embodiment, there are three buttons—a first display button 110, a second display button 111, and a power button 112. Buttons 110-112 may be any shape practicable, but in a preferred embodiment, display buttons 110 and 111 are elliptical, and button 112 is circular. (Note that a fourth button 113 protruding from the side of the housing, as seen in FIGS. 5 and 30, may also be used to power the apparatus up or down, as well as accomplish other functions as well).

Alternatively, other means of user input, such as touch screen, touch pad, track ball, joystick or voice commands may replace or augment the buttons.

Figure 43:
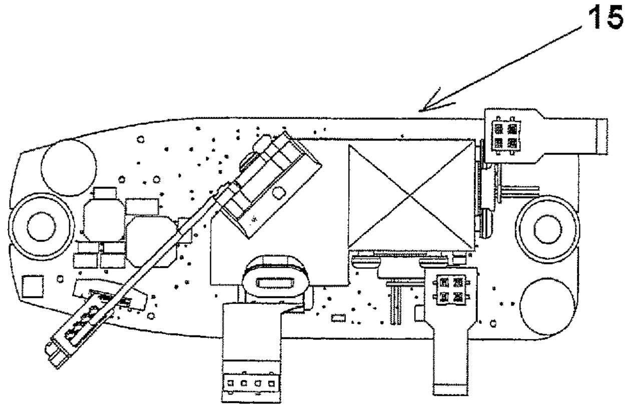
FIG. 43 is a top view of the photodiode assembly.

The internal circuitry 12 is illustrated in FIGS. 48-65, and can include a main circuit board 43, a user interface board 44, USB chip 46, and speaker 47. In one embodiment, the main circuit board 43 contains at least two orifices 48 and 49 which are adapted to receive mounting member 50 and mounting member 51. Mounting members 50 and 51 may be used to secure the main circuit board 43 to the heat sink 52. Mounting members 50 and 51 may be screws, or pins or any similar type of member used to secure internal circuitry known in the art. FIG. 43 is a schematic of a circuit diagram of the main circuit board 43 and how it connects to the remaining components of the present invention.

As seen in FIG. 30, heat sink 52 generally comprises a left sidewall 99, and right sidewall 100, and a front sidewall 104 extending between the left and right sidewall. In a preferred embodiment heat sink 52 may also contain a middle bridge 101 which connects the left sidewall 99 with the right sidewall 100. Extending from the middle bridge and curving downwards is a hook member 102. The hook member has an internal cavity 103, which is adapted to receive the USB chip 46. On the front sidewall 104, and left and right sidewalls 99 and 100, there may be cylindrical members 105 that are adapted to receive mounting screws 106, and may include the use of threaded inserts. Mounting members 40 may be used to mount the scanner assembly 15. In one embodiment, mounting members 40 may be screws. It will be appreciated that the photodiode assembly may be mounted by other means.

The heat sink capabilities might be enhanced by a fan or blower arranged in a way that would direct the air flow onto the heat sink and out of the housing. Additionally, a thermodynamic or thermoelectric heat pump may be employed between the heat-dissipating portions of the heat sink, to facilitate heat exchange. In a preferred embodiment, a heat shield 80 is mounted onto the top surface of the user interface board 44.

Preferably being directly connected the main circuit board 43, is the user interface board 44. FIG. 50 is a schematic of a circuit diagram of the user interface board. The user interface board 44 contains the firmware which sends a graphic user interface to the display 14, and stores the user's preferences. In one embodiment the interface board 44 is directly mounted to the top surface of the main circuit board. In one embodiment, the display 14 is directly mounted to the user interface board 44, and may be a Liquid Crystal Display (LCD). It will be appreciated to those skilled in the art that an Organic Light Emitting Diode display (OLED) could work equally well. Alternatively, other means of information delivery may be used, such as lamp or LED indicators and audible cues. Some of the information that may be delivered to the user, other than the projection of vein images onto a patient's arm, may be visual cues also being projected on the patient's arm alongside the vein images, visual cues regarding additional information concerning the veins.

Mounted to the user interface board may be a keypad 13. Keypad 13, as noted previously, may be comprised of a plurality of control means which may include, but is not limited to, a plurality of buttons 77. In a preferred embodiment, there may be three buttons used for controlling the apparatus—buttons 110-112. Each of these buttons may have a first end 78 and a second end 79. The first ends 78 of the plurality of buttons is adapted to be exposed through corresponding openings in the housing top section 17, where they may be toggled by the user. The second end 79 of the buttons is adapted to be received by the user interface board 44.

Also attached to the main circuit board is the USB chip 46. USB chip mounts to the main circuit board 43 at a pin connection, and provides a pin connection for speaker 65. The USB chip 46 is preferably mounted to the bottom surface of the main circuit board.

Figure 42:
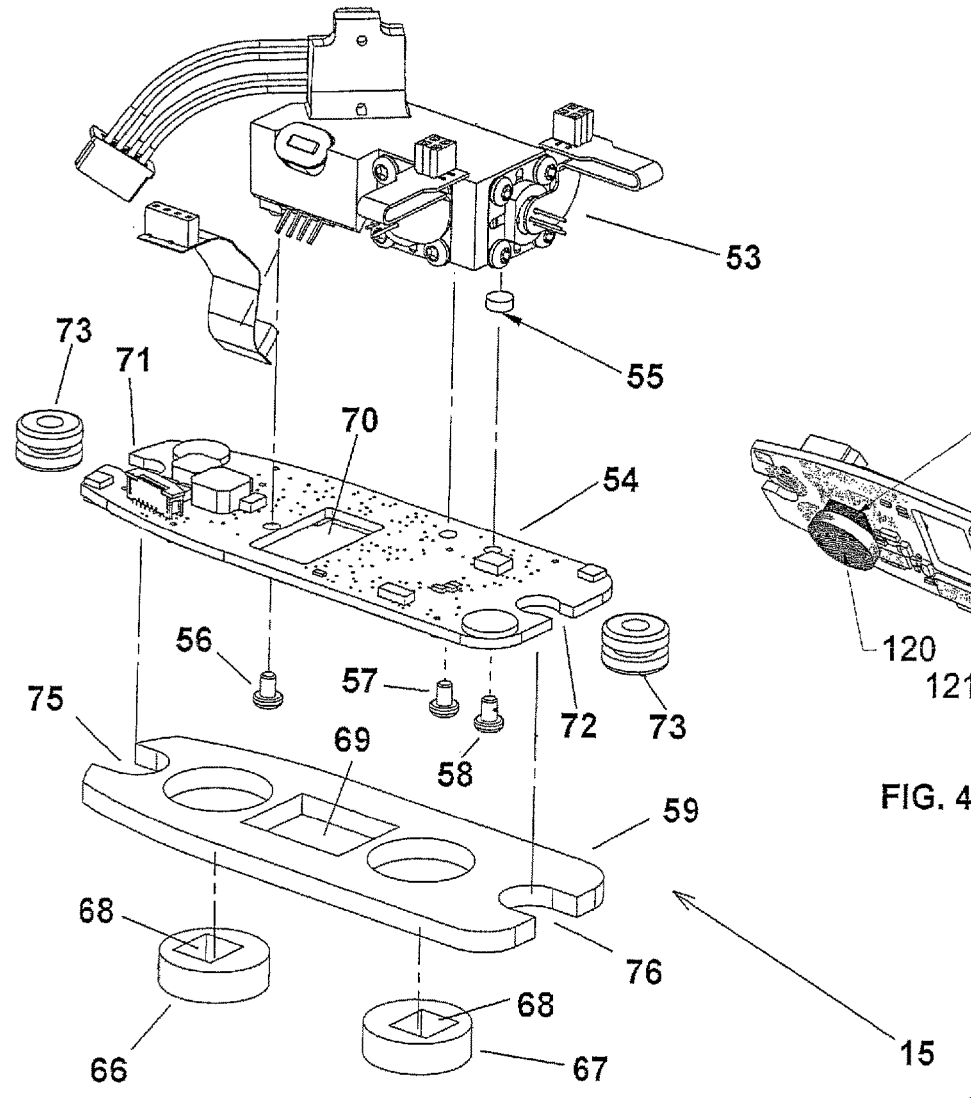
FIG. 42 is an exploded view of the photodiode assembly.

Also connected to the main circuit board is the scanner assembly 15 (FIG. 42). The scanner assembly 15 generally includes a photodiode engine 53, a photodiode board 54, and a heat pipe 55. In one embodiment, the photodiode engine 53 is directly mounted to the top surface of the photodiode board 54, by one or more screws 56, 57, and 58. In another embodiment, the bottom surface of the photodiode board is mounted to a foam fresen 59. In the same embodiment, the foam fresen 59 is mounted to the bottom plate of the bottom section. In a preferred embodiment the foam fresen 59 has an orifice 69 which is adapted to receive the portion of the photodiode engine which houses the display light 62. In a preferred embodiment the foam fresen 59 has a first arcuate cutout 75 at its front end and a second arcuate cutout 76 at its rear end. Arcuate cutouts 75 and 76 provide an arcuate surface for grommets 73 and 74 to be received.

Figure 44:
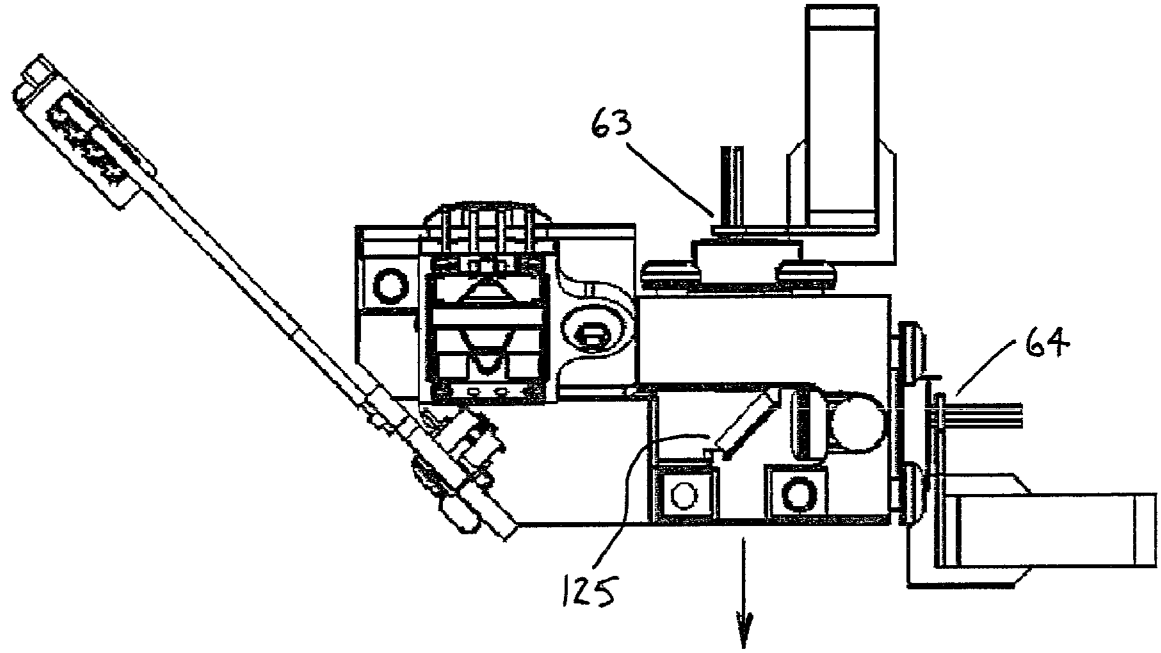
FIG. 44 is an bottom view of the photodiode engine.
Figure 45:
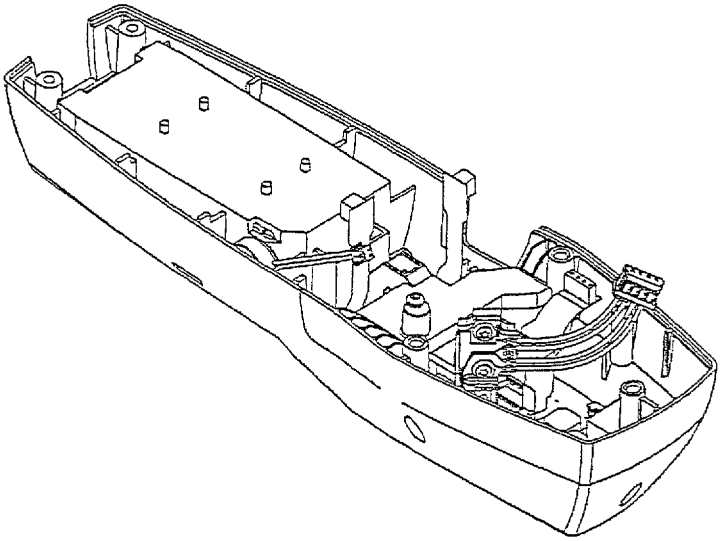
FIG. 45 shows a perspective view of the bottom section of the housing with a portion of the photodiode assembly mounted inside the cavity of the bottom section of the housing.
Figure 46:
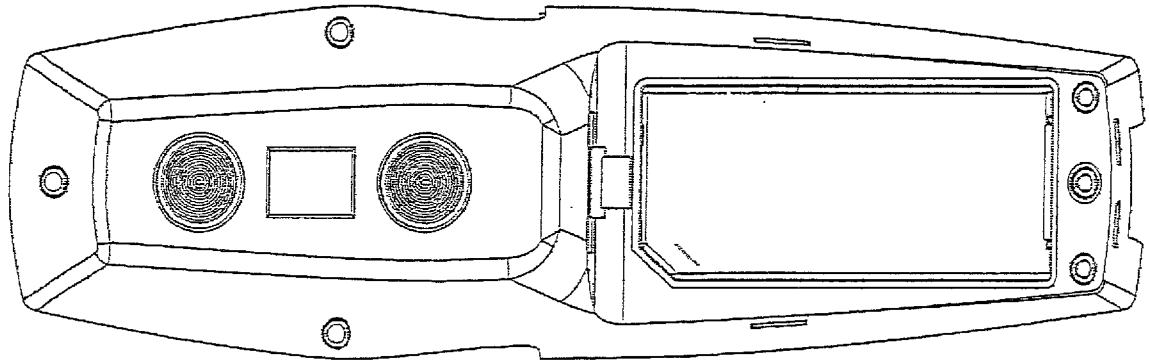
FIG. 46 is a bottom view of the portable apparatus of the present invention.

The photodiode engine comprises a display light 62 (FIG. 44). FIGS. 55, 61, and 65 are schematics of circuit diagrams relating to the photodiode engine and its peripheral connections. The display light 62 may be comprised of at least a red laser 63 and an infrared (IR) laser 64. In a preferred embodiment red laser 63 may be a laser diode emitting light at a wavelength of 642 nm, and an infrared (IR) laser 64 that may emit light at a wavelength in the near infrared to be at 785 nm. Other combinations of wavelengths of more than two lasers may be used to enhance both the collection of the vein pattern and the display of the collected information. Red laser 63 projects an image of the vein pattern on the patient's skin. The laser diode has a wavelength of 642 nm, which is in the visible red region, but falls outside the spectral response range of photodiodes 60 and 61. Red laser 63 illuminates areas with no veins, and does not illuminates areas with veins. This results in a negative image that shows the physical vein locations. Alternatively, the positive image may be used, where the red laser illuminates the vein locations and does not illuminate spaces between veins.

Figure 8:
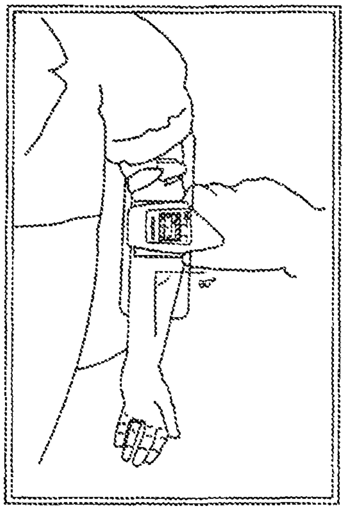
FIG. 8 is a Figure illustrating proper angling of the apparatus when being used to enhance the vein image of veins in a patient's arm.
Figure 9:
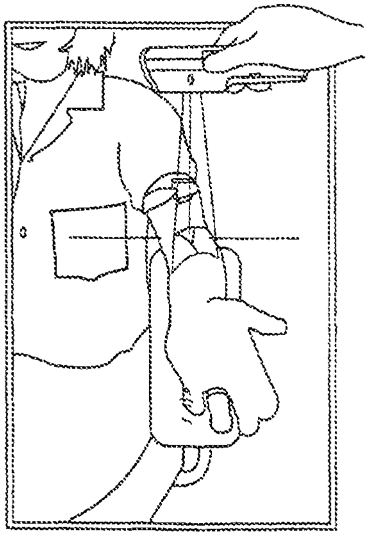
FIG. 9 is a Figure illustrating proper centering of the apparatus when being used to enhance the vein image of veins in a patient's arm.

The red laser may be employed to project information other than vein locations, by means of turning on the laser or increasing its brightness when the laser beam is passing over the brighter parts of graphical or symbolic information to be projected, and turning off the laser or increasing its brightness when the laser beam is passing over the darker parts of graphical or symbolic information to be projected. Such information may include the vein depth, vein diameter, or the degree of certainty with which the device is able to identify the vein location, expressed, for example, through the projected line width 501 (FIG. 66(*a*)), the length of the strokes in a dotted line 502 (FIG. 66(*b*)), as a bar graph 503 (FIG. 66(*c*)) or a numeric indication 504 (FIG. 66(*d*)). It may also include user's cues 505 and 506, respectively for optimizing the position of the device, such as choosing the correct tilt and distance to the target (FIG. 66(*e*)). Also, FIG. 8 shows that the device should be positioned at an approximate 90° right angle (perpendicular) to the direction of the vein flows, or is expected to flow, and the user can then often improve display quality by changing the angle slightly. Additionally, as shown in FIG. 9, the device's vein display light should be centered directly above the centerline of the vein to be located. To present the center of the vein accurately, the manufacturer recommends positioning the device directly over the vein. When the device is positioned properly, vein display is accurate and can be viewed from any angle. When held directly over the centerline of the vein the device locates the center of the vein extremely accurately. It is recommended that the device be held within ½" (1.25 cm) of either side of directly overhead. The device's vein display is always in focus, so the user can quickly move the device across a subject's skin to search for a vein. As a user evaluates and assesses a vein that has been located, it is important to center the device over the vein and not rotate the device to either side.

Vein location and other information may also be displayed by projection means other than scanning laser, through the use of, for example, a DLP (Digital Light Processing) projector, a LCoS (Liquid Crystal on Silicon) micro-projector, or a holographic projector.

Figure 70:
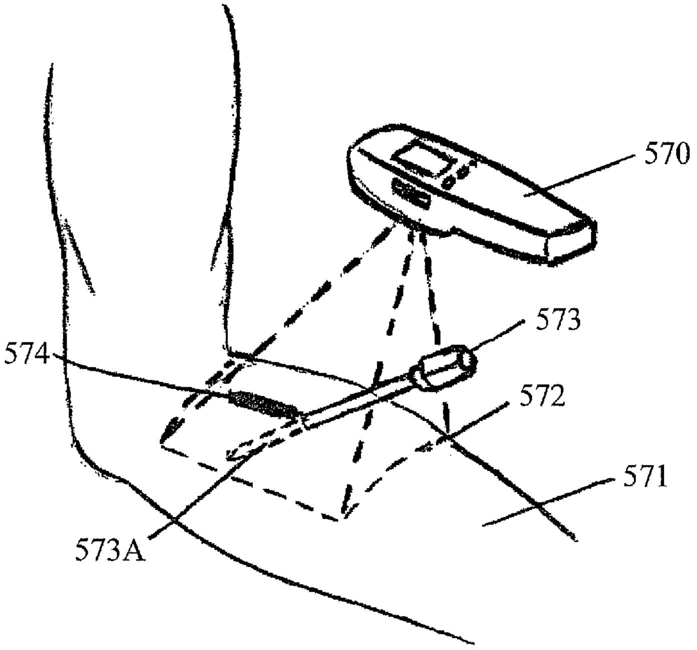
FIG. 70 illustrates the apparatus illuminating on the skin of a patient, a coated needle that has been inserted beneath the patient's skin.

Additionally, the firmware of the photodiode board 54 may be programmed to recognize and modify display 14, and projection by the display light 62 to represent a needle, catheter, or similar medical device 573 which has been inserted beneath a patient's skin and a part of it 573*a* is no longer visible to the naked eye (FIG. 70). The needle or medical apparatus may be made with, or coated with a material that absorbs or reflects a specified amount of the light from the IR laser 64. Glucose is one example of a biomedical material which could be used as a coating to absorb or reflects a specified amount of an IR laser. Photodiodes 60 and 61 will detect the difference in reflection and absorption, and the photodiode board 54 may modify display 14 to show the needle or medical device. The photodiode board 54 may also be programmed to modify projection by the display light 64 so that the needle or medical device which has been inserted into the patient's skin is displayed.

More detailed information on the use of the laser light to view the veins can be found in U.S. patent application Ser. No. 11/478,322 filed Jun. 29, 2006 entitled MicroVein Enhancer, and U.S. application Ser. No. 11/823,862 filed Jun. 28, 2007 entitled Three Dimensional Imagining of Veins, and U.S. application Ser. No. 11/807,359 filed May 25, 2007 entitled Laser Vein Contrast Enhancer, and U.S. application Ser. No. 12/215,713 filed Jun. 27, 2008 entitled Automatic Alignment of a Contrast Enhancement System the disclosures of which are incorporated herein by reference.

Figure 42A:
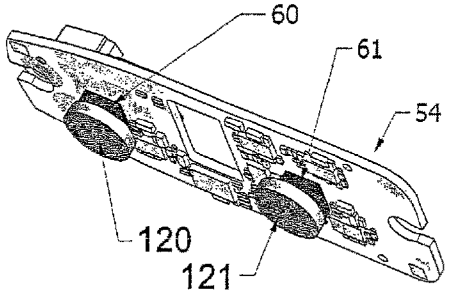
FIG. 42A is a reverse perspective view of the photodiode board in the exploded view of FIG. 42.

The photodiode board 54 comprises one or more silicon PIN photodiodes, which are used as optical detectors. In a preferred embodiment, photodiode board 54 comprises at least two silicon PIN photodiodes 60 and 61 (FIG. 42A). The field of view (FOV) of the optical detectors is preferably arranged to cover the entire area reachable by light from IR laser 64. FIGS. 8 and 10 are schematics of circuit diagrams which represent the photodiode board and its peripheral connections. In front of these photodiodes 60 and 61 are filters 120 and 121 (FIG. 42A) to serve as an optical filters that transmit infrared light, but absorb or reflect light in the visible spectrum. Mounted to photodiode 60 and 61 may be photodiode masks 66 and 67. Photodiode masks 66 and 67 comprise a shaped orifice 68 which is adapted to be received by photodiode 60 and 61 respectively. In a preferred embodiment photodiode masks 66 and 67 are circular and are adapted to be received by the cylindrical protrusions 31 and 32 of the housing bottom section 18. The photodiode board 54 is further comprised of an orifice 70. The opening 70 may be rectangular and adapted to receive the portion of the photodiode engine which houses display light 62. In a preferred embodiment the photodiode board 54 has a first arcuate cutout 71 at its front end, and a second arcuate cutout 72 at its rear end. Arcuate cutouts 71 and 72 provide an arcuate surface for grommets 73 to be received.

Other arrangements of optical detectors may be used too. In one possible arrangement, depicted on FIG. 67(*a*), the photodiode's field of view (FOV) 510 may be shaped by lenses-Fresnel lenses, curved mirrors or other optical elements 511—in such way that the FOV extent on the patient's arm becomes small and generally comparable with the size of the IR laser spot 512. This reduced FOV is forced to move synchronously with the laser spot by virtue of directing the optical path from the patient's arm to the photodiodes through the same scanning system 513 employed for the scanning of the laser beam, or through another scanning system, synchronous with the one employed for the scanning of the laser beam, so the FOV continuously overlaps the laser beam and follows its motion. Additional optical elements, such as a bounce mirror 514, might be used to align the laser bean with FOV. Such an arrangement is advantageous in that it enables the photodiodes to continuously collect the reflected light from the IR laser spot while the ambient light reflected from the rest of the target generally does not reach the photodiodes.

Figure 67A:
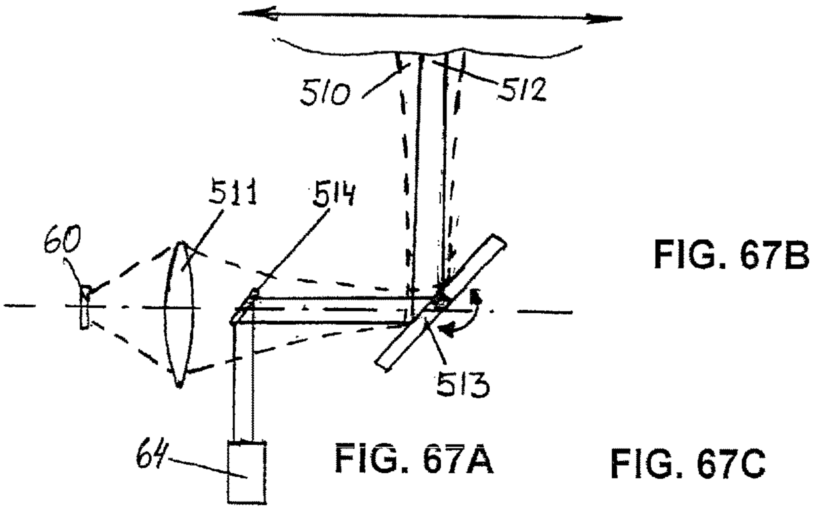
FIG. 67A illustrates a first arrangement of optical detectors that may be used for the apparatus.
Figure 67B:
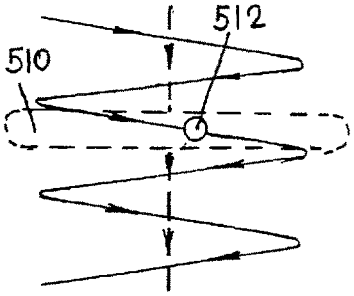
FIG. 67B schematically illustrates an alternative arrangement of optical detectors.
Figure 67C:
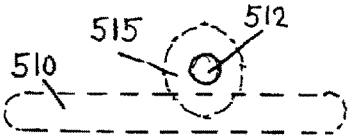
FIG. 67C illustrates a second alternative arrangement for the optical detectors.
Figure 68:
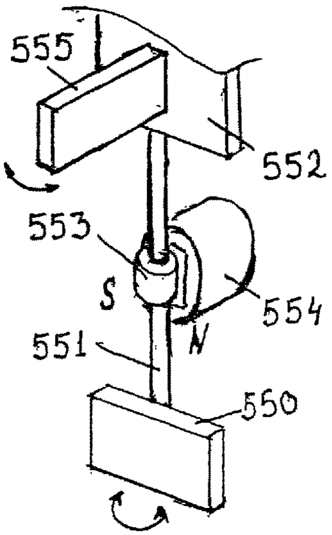
FIG. 68 illustrates one mechanical arrangement for the scanning mirrors.

Alternatively, the FOV of the photodiodes may be reduced in only one direction, and routed through the scanning system in such way that it follows the laser beam only in the direction where the FOV has been reduced, while in the other direction the FOV covers the entire extent of the laser scan (FIG. 67(*b*)). Such FOV may be shaped, for example, by a cylindrical lens in front of a photodiode. As the laser spot 512 is moving along a wavy path defined by superposition of the fast horizontal scan and slow vertical scan, the FOV moves only vertically, which the same speed as the slow vertical scan, thus covering the scan line the laser spot is currently on. Such arrangement may be implemented, for example, by routing the FOV of the photodiode only through the slow stage of the scanning system 513, but not its fast stage. Yet alternatively, the FOV may be shaped to follow the laser beam in close proximity without overlapping it (FIG. 67(*c*)). In this case, the FOV still moves in sync with the laser spot 512, but since it does not include the laser spot itself, the light reflected from the surface of the skin does not reach the photodiode. Instead, some portion of the light which penetrates the body, and, after scattering inside tissues, re-emerges from the skin surface some distance away from the laser spot, forming an afterglow area 515, which is partly overlapped with FOV. Collecting only the scattered light while reducing overall signal strength, has the advantage of avoiding variations caused by non-uniform reflections from random skin features and may be helpful in discerning deep veins.

Multiple photodiodes may also be arranged in an array in such way that their individual FOVs cover the entire area illuminated by the IR laser. At any given moment, only the signals from one or more photodiodes whose FOV overlap the laser beam or fall in proximity to it may be taken into the account.

Figure 71A:
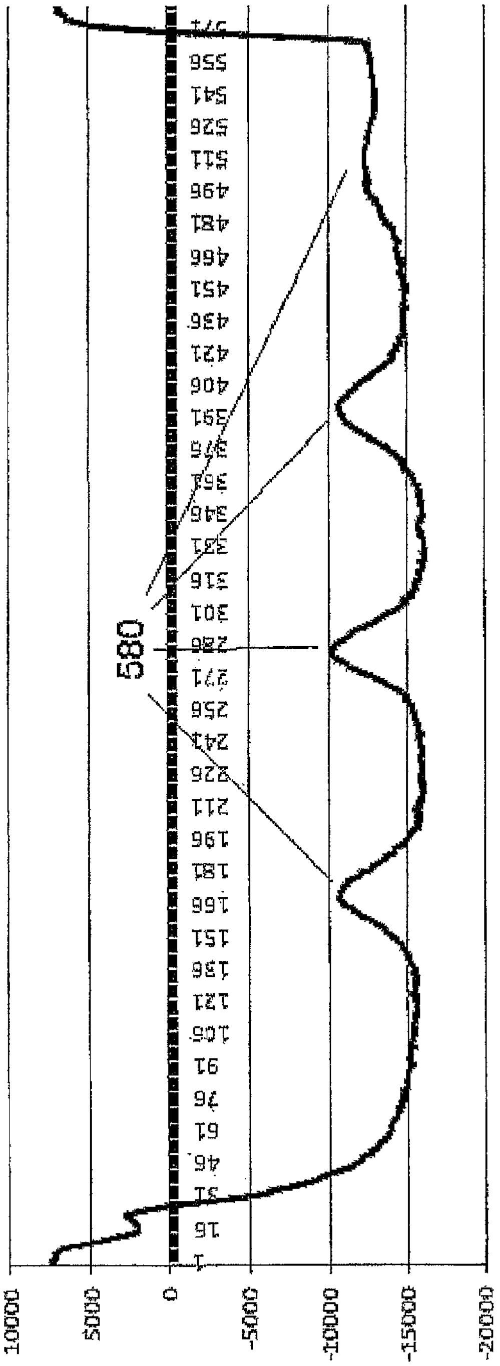
FIG. 71A illustrates a typical return signal collected from photodiodes of the current invention, with local peaks corresponding to vein locations.
Figure 71B:
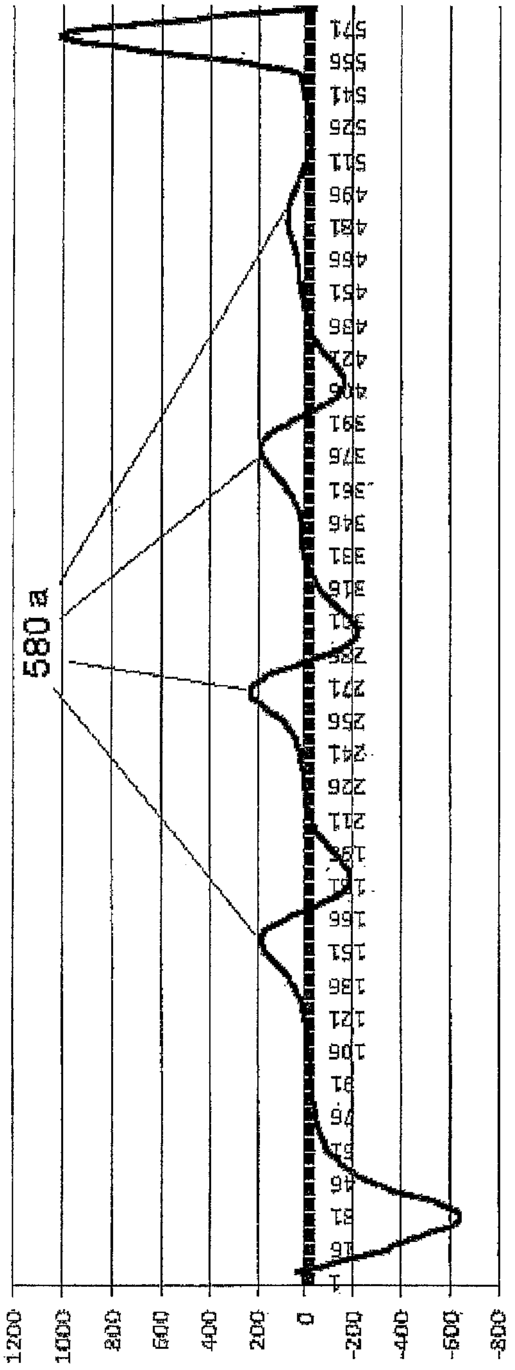
FIG. 71B represents the same signal of FIG. 71A after differentiation.

The photodiodes convert the contrasted infrared image returning from the patient into an electrical signal. The photodiode board 54 amplifies, sums, and filters the current it receives to minimize noise. The return signal of the photodiode engine 53 is differentiated to better facilitate discrimination of the contrast edges in the received signal received by photodiodes 60 and 61. FIG. 71 (*a*) represents a typical signal collected from photodiodes 60 and 61 and digitized. Local peaks 580 correspond to the locations of veins in the patient body. FIG. 71 (*b*) represents the same signal after the differentiation. Since differentiation is known to remove the constant parts of the signal and amplify its changing parts, peaks 580*a* can be easily found by comparison to ground reference (zero signal level of FIG. 71(*b*)). The photodiode board 54 also determines the locations where the infrared light has the lowest signal reflectivity using a scan system. These lower reflectivity locations indicate the vein locations.

Figure 72:
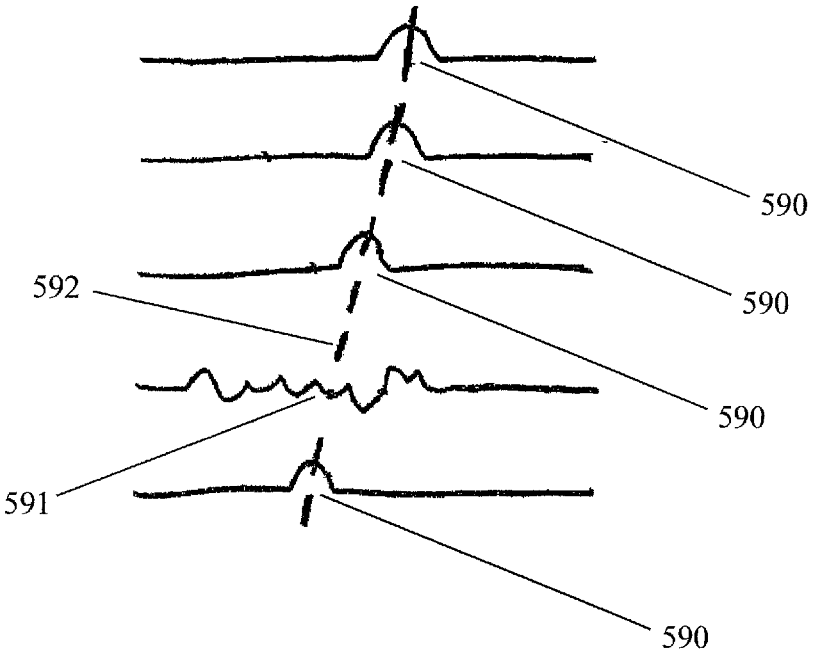
FIG. 72 illustrates a few consecutive scan lines crossing a single vein.

Signal processing methods other than differentiation, including Digital Signal Processing (DSP) may be employed as well, such as Fast Fourier Transform (FFT), Finite Impulse Response (FIR) and Infinite Impulse Response (IIR) filtration. Additionally, more complex image processing algorithms might be used, for example based on continuity analysis, as the veins generally form continuous patterns. For example, FIG. 72 shows a few consecutive scan lines crossing a single vein 592. While most lines produce distinctive signal peaks 590, indicating the vein location, in some lines those picks might by masked by noise 591. Still, connecting the vein location points derived from distinctive picks allows the algorithm to establish and display the true location of the vein.

To facilitate the use of DSP algorithms, the electronic circuitry to digitize the signal from the photodiodes and store it subsequently in some form of digital memory might be provided. Consequently, the display of the vein pattern by the red laser might be delayed with respect to the acquisition of said pattern with the IR laser. Such delay may vary from a small fraction of the time interval needed to scan the entire display area to several such intervals. If necessary, an intentional misalignment between the red and IR laser might be introduced, so the red laser can light up or leave dark the areas where the IR laser detected the lower or higher reflectivity, although the red laser beam would travel through those areas at different times than the IR laser.

The scan system employed by the apparatus 10 of the present invention uses a two dimensional optical scanning system to scan both the infrared and visible laser diodes. A dichroic optical filter element 125 in FIG. 44 allows laser diodes 63 and 64 to be aligned on the same optical axis and be scanned simultaneously. This allows for a minimal time delay in detecting the infrared reflected signal, and then re-projecting the visible signal.

The scan system employed by the apparatus 10 of the present invention has a horizontal and vertical cycle. Vertical scanning is driven in a sinusoidal fashion, and in one embodiment it occurs at 56.6 Hz, which is derived from 29 KHz sinusoidal horizontal scan. The Scan system is also interlaced. During a horizontal cycle the projection system is active only one half the horizontal scan system and blanked during the alternate half of the scan cycle. On the alternate vertical cycle the blanked and active portion of the horizontal scan is reversed. The top and bottom areas of the scan are blanked as well with a small area at the top of scan, located behind a mechanical shield for safety, reserved for execution of a laser calibration activity.

Alternative scan system might be used as well, such as those using a single scanning mirror deflectable in two orthogonal directions, or two uni-directional mirrors with smaller ratios of horizontal and vertical frequencies, such that the scan pattern forms a Lissajou figure (See http://www.diracdelta.co.uk/science/source/I/i/lissajous%20figures/source.html, and for animated figures, http://ibiblio.org/e-notes/Lis/Lissa.htm, which are incorporated herein by reference).

Various mechanical arrangements for scanning mirrors may be used. In one embodiment (FIG. 63) the mirror 550, made of glass, plastic or silicon, is attached to a free end of a cantilevered torsion fiber 551, made of glass or other linearly-deformable material, the other end of which is fixed to a base plate 552. A magnet 553, polarized in a direction perpendicular to the fiber, is attached to the fiber between the base plate and the mirror. A coil 554 may be positioned in close proximity to the magnet. The coil 554 may be used both for driving the mirror by virtue of energizing it with AC current, as well as for collecting the positional feedback by virtue of amplifying the voltage induced in the coil by magnet's oscillations. Both functions may be accomplished simultaneously, for example, by using one half of the mirror's oscillatory cycle for driving and the other half for collecting feedback. Alternatively, other means of driving the mirror, such as inducing torsional oscillation on the entire base plate by means of a piezo-electric element 555, might be used. The magnet 553 and the coil 554 are used exclusively for feedback in this case.

The torsion mode of the fiber 551 may be higher than fundamental, meaning that at least one torsional node, i.e. a cross-section of the fiber which remains still during oscillations, is formed. Such nodes allows for generally higher oscillation frequency at the expense of generally lower oscillation amplitude.

Figure 69:
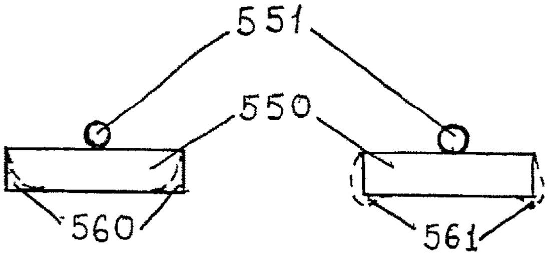
FIG. 69 illustrates smoothing of the edges of the scanning mirrors to improve the high resolution images at smooth video rates.

Since high oscillation frequency is desirable to obtain high-resolution images at smooth video rates, the linear speed of the mirror's outer edges becomes quite high as well, leading to excessive dust buildup along those edges. To alleviate this problem, the edges of the mirror may be smoothed by either removing some mirror material 560 (FIG. 69), or adding a layer of bevel-shaped coating 561 around the edges of the mirror.

Non-mechanical scanning systems, such as acousto-optic, electro-optic or holographic might be employed as well.

Figure 73:
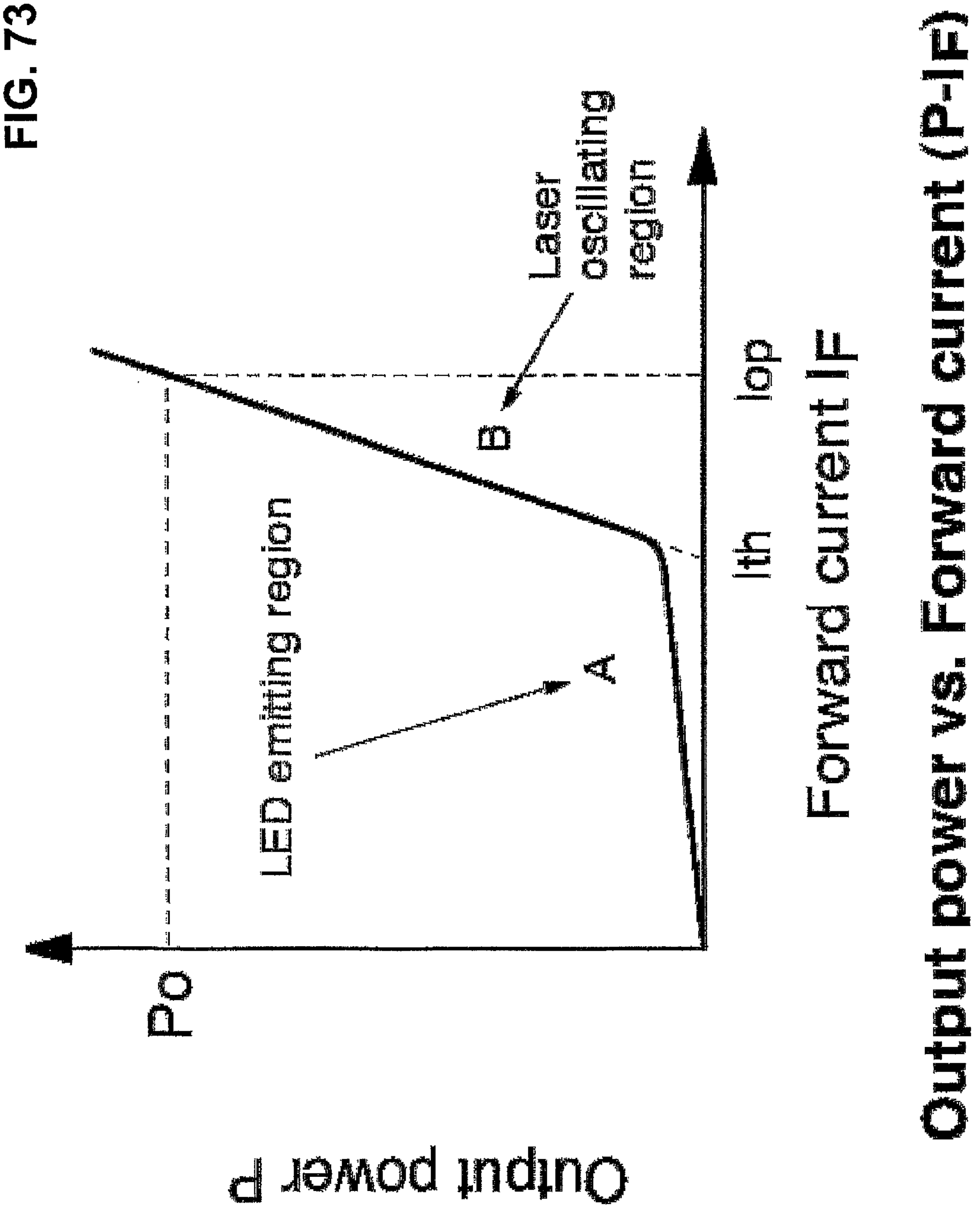
FIG. 73 is a graph showing the output power versus the forward current for a laser, to illustrate an inflection point.

In a preferred embodiment, each scan line is divided into 1024 pixels numbered 0-1023. In pixel range 0-106, red laser 63 is at its threshold, and IR laser 64 is off. The term "threshold", as applicable to lasers, means an inflection point on the laser Power-Current (P-I) curve, where the current becomes high enough for the stimulated emission (aka "lasing") to begin. This point is marked Ith of FIG. 73, which, while taken from the documentation of Sanyo Corp., is representative of the vast majority of laser diodes. In pixel range 107-146, red laser 63 is active, and IR laser 64 is at its threshold. In pixel range 182-885, red laser 63 is active, and IR laser 64 is on. In pixel range 886-915, red laser 63 is active, and IR laser 64 is off. In pixel range 916-1022, red laser 63 is at its threshold, and IR laser 64 is off. In pixel range 0-106, red laser 63 is at its threshold, and IR laser 64 is off.

Projection is accomplished by loading the appropriate compare registers in the complex programmable logic device, or CPLD. The content of the registers is then compared to the running pixel counter, generating a trigger signal when the content of a register matches the pixel count. The "left" register is loaded with the pixel count of when the laser should be turned off and the "right" register loaded with the pixel count of when the laser should be turned back on. The registers should be loaded on the scan line prior to the line when the projection is to occur. Projection is only allowed during the "Active" part of the red laser scan, i.e. between pixels 107 and 916, as explained above.

To improve vein visibility it is important to maintain the laser spot of a proper size on the surface of the patient's skin. This may be accomplished by fixed laser-focusing optics, or by an auto-focusing system which adjusts the beam focusing in response to changes in the distance to the target.

Certain patient's veins or a portion of their veins might not be displayed well or at all. Causes for veins not be displayed include vein depth skin conditions (e.g. eczema, tattoos), hair, highly contoured skin surface, and adipose (i.e. fatty) tissue. The apparatus is not intended to be used as the sole method for locating veins, but should be used either prior to palpation to help identify the location of a vein, or afterwards to confirm or refute the perceived location of a vein. When using the apparatus qualified medical personnel should always follow the appropriate protocols and practices.

In one embodiment, when the user wishes to operate the apparatus, the user may apply a perpendicular force to the top surface of the side button 113, or depress power button 112 to power the device. Once the device has been powered, the user can turn on the display light 62 by pressing and holding the top surface of the side button 113 for a set amount of time. In a preferred embodiment the photodiode board 54 has been programmed to activate the display light 62 after the user has held side button 113 for a half second.

Figure 20:
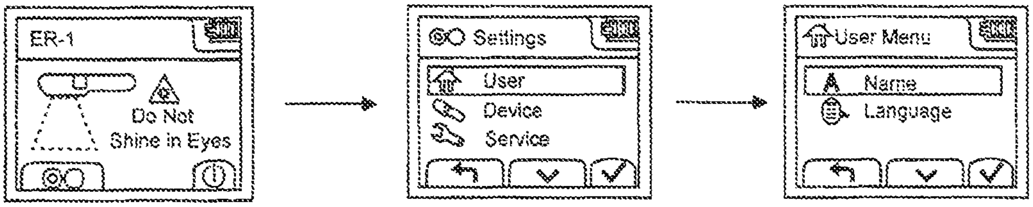
FIG. 20 is a series of screen shots showing the steps for labeling of the apparatus according to a user's preference.
Figure 20A:
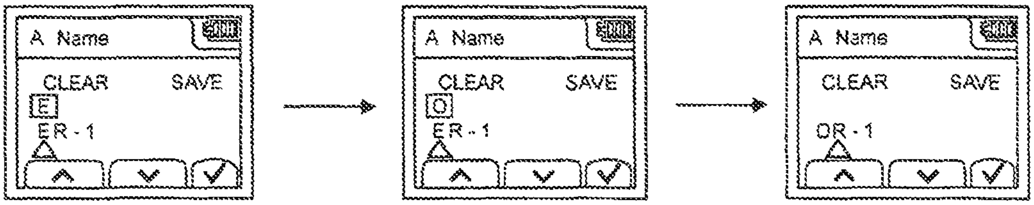
FIG. 20A is a series of screen shots showing use of up/down arrows for character selection.
Figure 21:
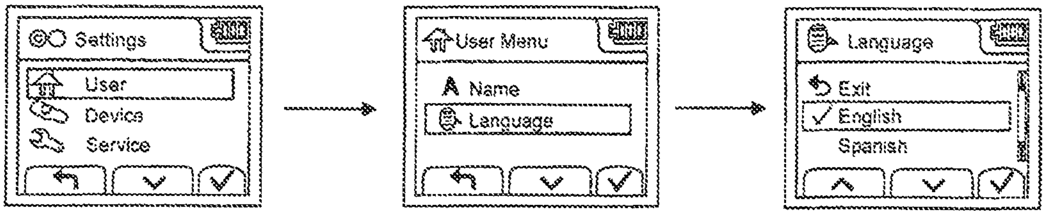
FIG. 21 is a screen shot illustrating how to change or review the language utilized on the apparatus.
Figure 22:
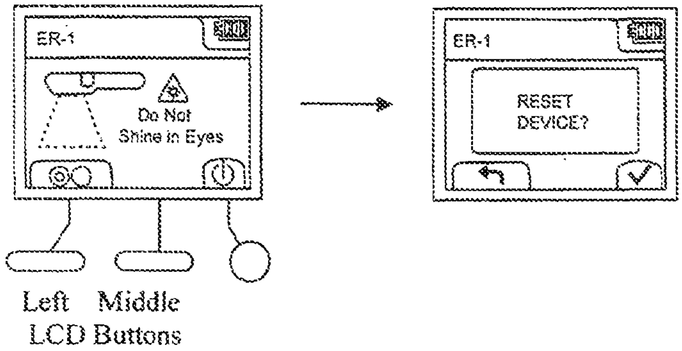
FIG. 22 is a screen shot illustrating how to reset all of the settings for the apparatus back to the factory default settings.
Figure 23:
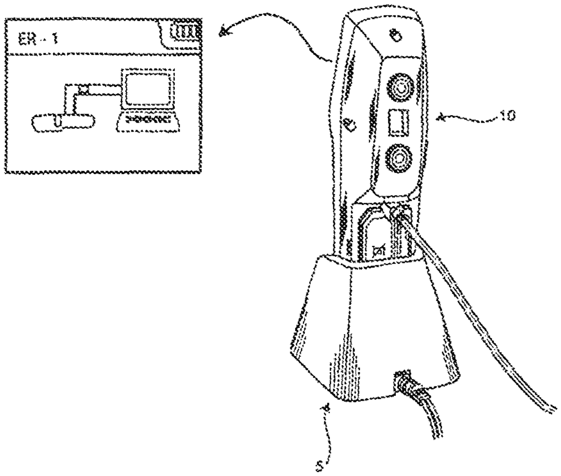
FIG. 23 is a perspective view illustrating plugging a USB cable into the back of the apparatus to communicate with a PC, and a screen shot illustrating the LCD screen of the device schematically illustrating the connection.
Figure 24:
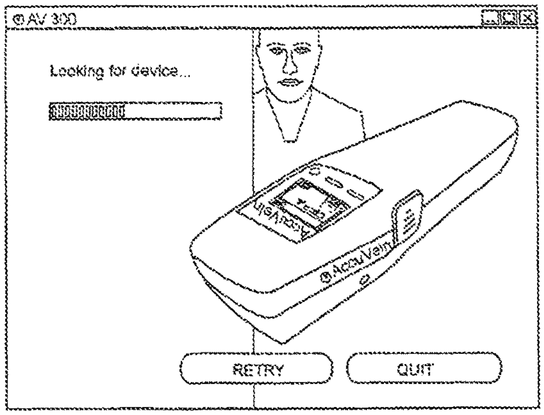
FIG. 24 is a screen shot as it would appear on the PC of FIG. 23 when looking for the apparatus.
Figure 25:
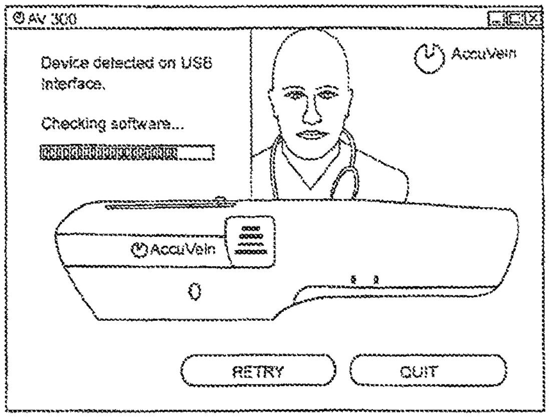
FIG. 25 is a screen shot as it would appear on the PC after the apparatus was detected, and the software running on the PC was checking to see if the apparatus software was current or needed to be updated.
Figure 26:
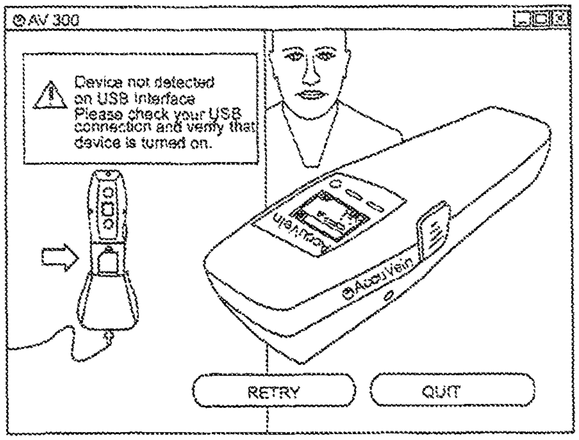
FIG. 26 is a screen shot as it would appear on the PC, when an apparatus is not detected by the PC.
Figure 27:
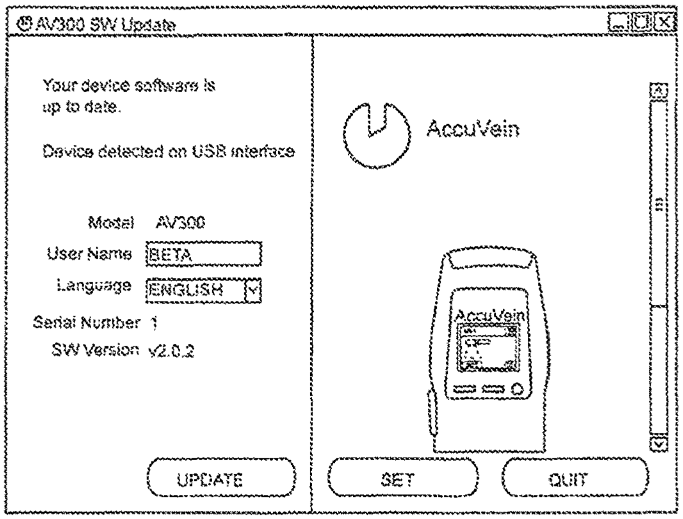
FIG. 27 is a screen shot illustrating the capability of naming the apparatus or changing the language, and doing so from the PC.
Figure 28:
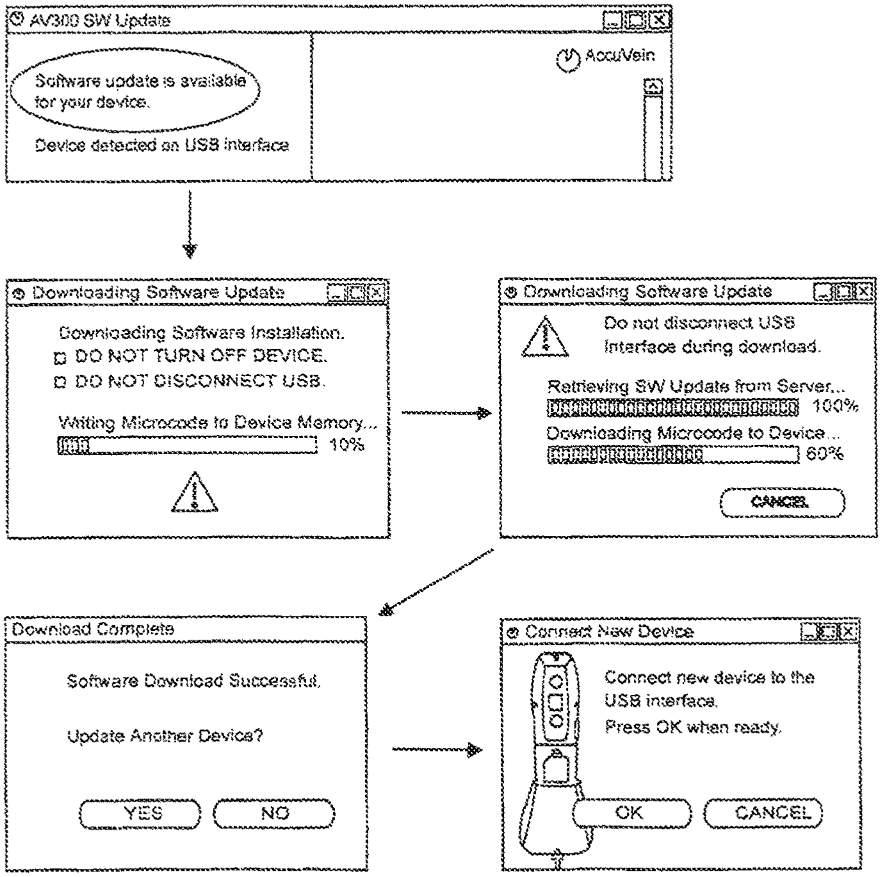
FIG. 28 is a series of screen shots of the PC illustrating the steps in which the software of an apparatus is updated.
Figure 29:
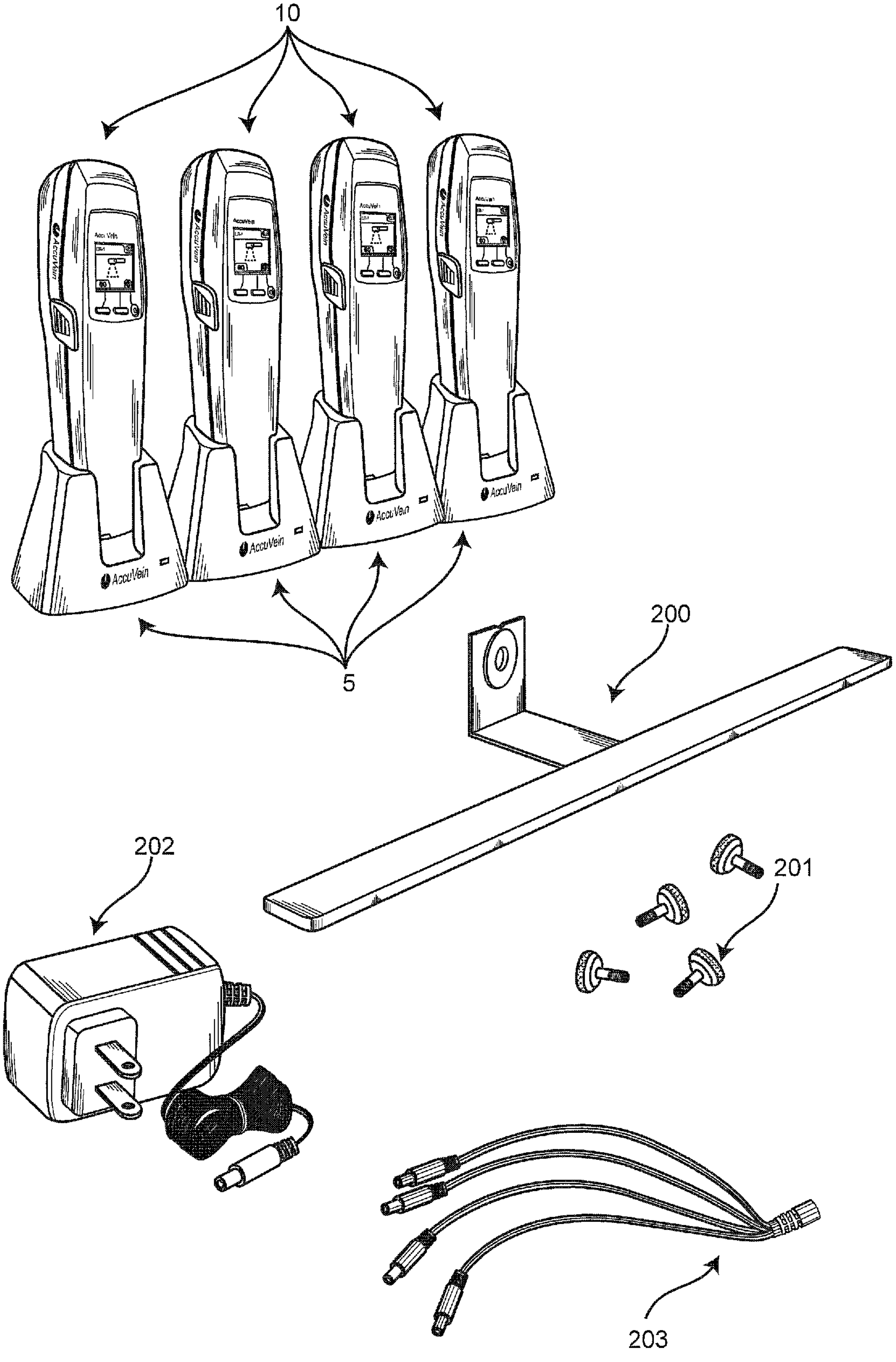
FIG. 29 illustrates a cradle pack and mounting hardware for use in a medical environment utilizing a series of vein enhancing apparatuses.

Embedded in the user interface board 44 may be firmware, which supports the displaying, upon LCD 14, of a menu system (see FIGS. 15-22). The menu system permits a user to access a plurality of features that the apparatus of the present invention can perform. The user can cycle through different display modes that the firmware has been programmed to transmit to the display by tapping the top surface of the side button 98. The features embedded in the firmware can include a menu system, menu settings, display status. In one embodiment, the first LCD button 110 is programmed to access the menu mode (FIG. 15). One of those features of the firmware permits labeling or naming of a particular apparatus, as seen in FIG. 20. Such labeling may become advantageous in an environment where a medical service provider utilizes a plurality of the apparatus 10, such as in an emergency room. The plurality of apparatus 10 may be maintained in a corresponding plurality of rechargeable cradles 5, which may be mounted to a bracket 200, and secured thereto using fastening means 201, as seen in FIG. 29. Power to the cradles 5 may be supplied from an adapter 202 plugged into a wall outlet, with a power splitter 203 supplying power to each cradle 5. Each of the plurality of apparatus 10 in this example may be appropriately labeled, "ER1," "ER2," . . .

When the apparatus's 10 display light 62 is activated, the apparatus 10 can be used to locate veins. The user can access the scan function by navigating to it using the keypad 13. The firmware will contain a feature which will allow the user to cycle through display settings using a menu system to optimize vein display for the current subject. When the display light 62 is deactivated, the display 14 remains available for viewing status and making configuration settings using the menu system.

What is claimed is:

1. A method for optimizing a projected vein image on a target skin surface of a patient using a vein imager, said method comprising:

forming the vein imager using: a housing for single-handed lifting and portable use of the vein imager; a first laser for emitting a first wavelength of light; a second laser for emitting a second wavelength of light; a scanner for scanning said emitted first wavelength of light and second wavelength of light from the first and second lasers in a pattern onto the target skin surface; one or more optical detectors for receiving a vein image formed by differential amounts of absorption and reflection of said emitted light at said first wavelength, and for converting the vein image into a signal; and using the second wavelength of light for projecting the received vein image onto the target skin surface of the patient using the signal;

positioning the vein imager above the target skin surface of the patient;

activating the vein imager and directing said scanned light from the vein imager toward the target skin surface;

centering said scanned light upon a selected vein of the target skin surface within one-half of an inch of either side of the selected vein; and rotating the vein imager until orienting an axial direction of the vein imager perpendicularly to a direction of the selected vein of the target skin surface.

2. The method according to claim 1, further comprising: providing user's cues for optimizing the positioning of the vein imager over the selected vein of the target skin surface.

3. The method according to claim 2, further comprising: providing user's cues for optimizing a tilt of the vein imager over the selected vein of the target skin surface.

4. The method according to claim 3, further comprising: providing user's cues for optimizing a distance of the vein imager to the selected vein of the target skin surface.

5. A vein imager, for use in identifying vein locations of a target skin surface of a patient and a tip of a venipuncture needle to aid in a venipuncture process, said vein imager comprising:

a housing, said housing configured for single-handed lifting and portable use of said vein imager during the venipuncture procedure;

a microcontroller;

a user interface board comprising:

a display screen;

at least one button; and firmware, said firmware configured to supply a graphic user interface to said display screen;

a first laser, said first laser configured to emit a first wavelength of light;

a second laser, said second laser configured to emit at least a second wavelength of light; said at least a second wavelength being different than said a first wavelength of light;

one or more optical detectors, said one or more optical detectors each configured to be responsive to said first wavelength of light; said one or more optical detectors being further configured to receive a contrasted image from the target skin surface formed by reflected light at said first wavelength being amplitude modulated according to differential amounts of absorption and reflection between subcutaneous veins and surrounding tissue therein, and said one or more optical detectors being configured to convert said received contrasted image into an electrical signal;

electronic circuitry, said electronic circuitry configured to receive said electrical signal from said one or more optical detectors and to output said electrical signal to said second laser for projection of said contrasted image and the vein locations therein upon the target skin surface using said at least a second wavelength of light;

a venipuncture needle, said venipuncture needle comprising: a biomedical material coating on at least at a tip of said venipuncture needle, said biomedical material coating being configured to absorb a specified amount of said first wavelength of light, being detectable in said contrasted image by said one or more optical detectors;

wherein said firmware is configured to recognize said biomedical material coating on said tip of said venipuncture needle beneath the target surface in said received contrasted image; and wherein said at last one button is configured to be toggled, to cause said vein imager to project an outline of said venipuncture needle onto the target skin surface within said projected vein image.

6. The vein imager according to claim 5, wherein said firmware is configured to modify projection of said contrasted image as a position of said venipuncture needle is progressively inserted beneath the target skin surface of the patient.

7. The vein imager according to claim 6, wherein said biomedical material coating comprises: glucose.

8. A vein imager, for use in identifying vein locations of a target skin surface of a patient to aid in a venipuncture process, said vein imager comprising:

a housing, said housing configured for single-handed lifting and portable use of said vein imager during a venipuncture procedure;

a first laser, said first laser configured to emit a first wavelength of light;

a second laser; said second laser configured to emit at least a second wavelength of light; said at least a second wavelength being different than said a first wavelength of light;

one or more optical detectors; said one or more optical detectors each configured to be responsive to said first wavelength of light; said one or more optical detectors being configured to receive a contrasted image from the target skin surface formed by reflected light at said first wavelength being amplitude modulated according to differential amounts of absorption and reflection between subcutaneous veins and surrounding tissue therein, and said one or more optical detectors being configured to convert said received contrasted image into an electrical signal;

electronic circuitry; said electronic circuitry configured to receive said electrical signal from said one or more optical detectors and to output said electrical signal to said second laser;

a scanner, said scanner configured to scan said first and second wavelengths of light in a pattern onto the target skin surface to create the contrasted image using said first wavelength of light and to cause projection of said contrasted image upon the target skin surface using said second wavelength of light; said scanner comprising:

a base plate;

a torsion fiber, said torsion fiber configured to cantilever away from said base plate;

said torsion fiber formed of a linearly deformable material;

a mirror, said mirror being secured to said torsion fiber at a position being distal with respect to said base plate;

a magnet, said magnet being polarized in a direction perpendicular to a direction of said cantilever of said torsion fiber, said magnet being secured to said torsion fiber between said base plate and said mirror; and a mechanism configured to drive said mirror to oscillate to produce said scanned pattern.

9. The vein imager according to claim 8, wherein said mirror is configured to prevent dust buildup at each of a first end and a second end of said mirror.

10. The vein imager according to claim 9, wherein said mirror being configured to prevent dust buildup at said first and second ends comprises: a bevel-shaped coating applied to each of said first and second ends of said mirror, said bevel-shaped coating being configured to resist dust buildup.

11. The vein imager according to claim 9, wherein said mirror being configured to prevent dust buildup at said first and second ends comprises: each of said first and second ends being smoothed by removing some material.

12. The vein imager according to claim 8, wherein said mechanism configured to drive said mirror to oscillate is a coil, said coil being positioned adjacent to said magnet.

13. The vein imager according to claim 12, wherein said coil is configured to be energized by AC current.

14. The vein imager according to claim 13, wherein said coil is configured to collect positional feedback for said mirror by amplifying a voltage induced in said coil by oscillation of said magnet.

15. The vein imager according to claim 8, further comprising: a coil, said coil being positioned adjacent to said magnet, and being configured for use in combination with said magnet to provide positional feedback for said mirror;

wherein said mechanism configured to drive said mirror to oscillate is a piezo-electric element.

16. The vein imager according to claim 8, wherein said torsion fiber is formed of a material from the group consisting of: glass, plastic, and silicon.

17. The vein imager according to claim 8, wherein said scan pattern of said scanner comprises: a scan cycle consisting of a horizontal scan cycle and a vertical scan cycle;

wherein said scan pattern in said vertical scan cycle is driven to be sinusoidal; and wherein said scan pattern is interlaced, whereby said horizontal scan cycle is active only during one half of said scan cycle and blanked during a second half of said scan cycle, and wherein on an alternate said vertical scan cycle said blanked and active portions of the horizontal scan are reversed.

18. The vein imager according to claim 17, wherein said sinusoidal scan pattern in said vertical scan cycle is driven to be at 56.6 hertz.

19. The vein imager according to claim 8, further comprising: an autofocus system configured to adjust said scan of said first and second wavelengths of light in said pattern onto the target skin surface based on changes in a distance to the target skin surface.

* * * * *